United States Patent
Konowalchuk et al.

(10) Patent No.: US 10,232,007 B2
(45) Date of Patent: *Mar. 19, 2019

(54) HIGH MOLECULAR WEIGHT POLYSACCHARIDE THAT BINDS AND INHIBITS VIRUS

(71) Applicant: World Force Technologies, LLC, Newport, OR (US)

(72) Inventors: Thomas W. Konowalchuk, Newport, OR (US); Jack Konowalchuk, Newport, OR (US)

(73) Assignee: WORLD FORCE TECHNOLOGIES, LLC, Newport, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/623,331

(22) Filed: Jun. 14, 2017

(65) Prior Publication Data
US 2018/0000882 A1  Jan. 4, 2018

Related U.S. Application Data

(63) Continuation of application No. 14/107,553, filed on Feb. 16, 2013, now Pat. No. 9,707,263, which is a
(Continued)

(51) Int. Cl.
*A61K 36/87* (2006.01)
*A61K 9/00* (2006.01)
(Continued)

(52) U.S. Cl.
CPC ............ *A61K 36/87* (2013.01); *A61K 9/0014* (2013.01); *A61K 9/0095* (2013.01);
(Continued)

(58) Field of Classification Search
CPC .............................. A61K 31/353; A61K 31/70
See application file for complete search history.

(56) References Cited

U.S. PATENT DOCUMENTS

| 4,533,548 A | 8/1985 | Umezawa et al. |
| 4,698,360 A | 10/1987 | Masquelier |

(Continued)

FOREIGN PATENT DOCUMENTS

WO   WO 2010/088222   8/2010

OTHER PUBLICATIONS

Canadian Office Action dated Dec. 8, 2017 issued in CA 2,787,429.
(Continued)

*Primary Examiner* — San Ming R Hui
(74) *Attorney, Agent, or Firm* — Emily M. Haliday; Weaver Austin Villeneuve & Sampson LLP

(57) ABSTRACT

This invention provides a high molecular weight polysaccharide capable of binding to and inhibiting virus and related pharmaceutical formulations and methods of inhibiting viral infectivity and/or pathogenicity, as well as immunogenic compositions. The invention further includes methods of inhibiting the growth of cancer cells and of ameliorating a symptom of aging. Additionally, the invention provides methods of detecting and/or quantifying and/or isolating viruses.

24 Claims, 46 Drawing Sheets

Related U.S. Application Data continuation of application No. 12/694,226, filed on Jan. 26, 2010, now Pat. No. 8,629,121.

(60) Provisional application No. 61/206,197, filed on Jan. 27, 2009.

(51) Int. Cl.
*A61K 31/353* (2006.01)
*A61K 31/715* (2006.01)
*C12N 7/00* (2006.01)
*G01N 33/569* (2006.01)

(52) U.S. Cl.
CPC .......... *A61K 31/353* (2013.01); *A61K 31/715* (2013.01); *C12N 7/00* (2013.01); *G01N 33/56983* (2013.01)

(56) References Cited

U.S. PATENT DOCUMENTS

| | | | |
|---|---|---|---|
| 5,211,944 A | 5/1993 | Tempesta | |
| 5,484,594 A | 1/1996 | Frangi et al. | |
| 5,585,365 A | 12/1996 | Hayashi et al. | |
| 6,528,061 B1 | 3/2003 | Phalipon et al. | |
| 6,573,245 B1 | 6/2003 | Marciani | |
| 8,629,121 B2 * | 1/2014 | Konowalchuk ...... | A61K 9/0014 514/54 |
| 9,707,263 B2 * | 7/2017 | Konowalchuk ...... | A61K 9/0014 |
| 2004/0038931 A1 | 2/2004 | Elsobly et al. | |
| 2005/0276872 A1 | 12/2005 | Chan et al. | |
| 2006/0276432 A1 | 12/2006 | Oku et al. | |

OTHER PUBLICATIONS

International Search Report and Written Opinion dated Oct. 27, 2010 issued in PCT/US2010/022148 (WO 2010/088222).
International Preliminary Report on Patentability dated Aug. 2, 2011 issued in PCT/US2010/022148 (WO 2010/088222).
EP Supplementary Search Report dated May 31, 2013 issued in EP 10736306.1.
Australian Office Action dated Jul. 8, 2014 issued in AU 2010208429.
Australian Notice of Acceptance dated Aug. 11, 2015 issued in AU2010208429.
Canadian Office Action dated Feb. 1, 2016 issued in CA 2,787,429.
Canadian Office Action dated Sep. 29, 2016 issued in CA 2,787,429.
Canadian Office Action dated May 5, 2017 issued in CA 2,787,429.
U.S. Office Action dated Feb. 15, 2013 issued in U.S. Appl. No. 12/694,226.
U.S. Notice of Allowance dated Sep. 9, 2013 issued in U.S. Appl. No. 12/694,226.
U.S. Office Action dated Dec. 3, 2015 issued in U.S. Appl. No. 14/107,553.
U.S. Final Office Action dated Jun. 22, 2016 issued in U.S. Appl. No. 14/107,553.
U.S. Notice of Allowance dated Mar. 15, 2017 issued in U.S. Appl. No. 14/107,553.
Cataldi et al. (2000) "Carbohydrate analysis by high-performance anion-exchange chromatography with pulsed amperometric detection: The potential is still growing." *Fresenius J. Anal. Chem.* 368: 739-758.
Nair et al. (2002) "Grape Seed Extract Activates Th1 Cells in Vitro" *Clin Diagn Lab Immunol.* 9(2):470-476.
Zhu et al. (2006) "Antiviral property and mechanisms of a sulphated polysaccharide from the brown alga Sargassum patens against Herpes simplex virus type 1." *Phytomedicine* 13: 695-701.

* cited by examiner

A
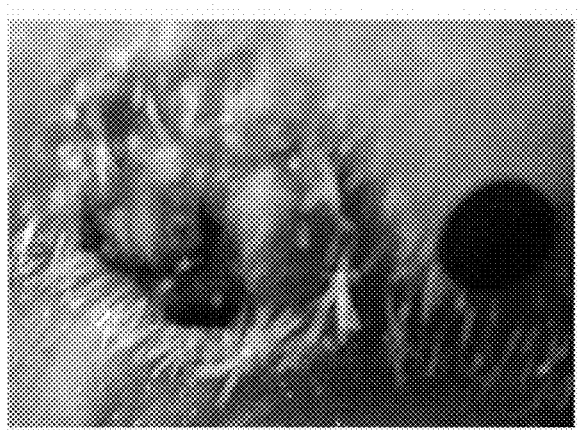
B
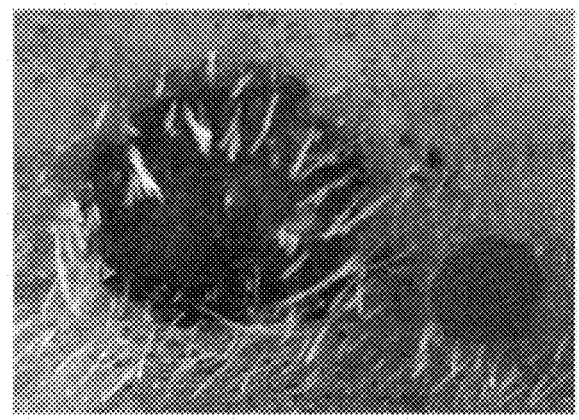
C
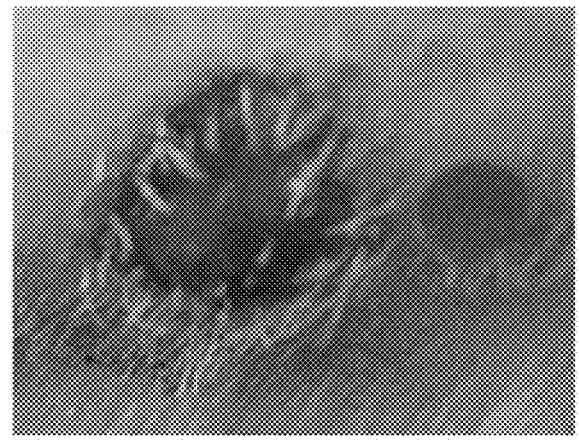
*Fig. 4A-C*

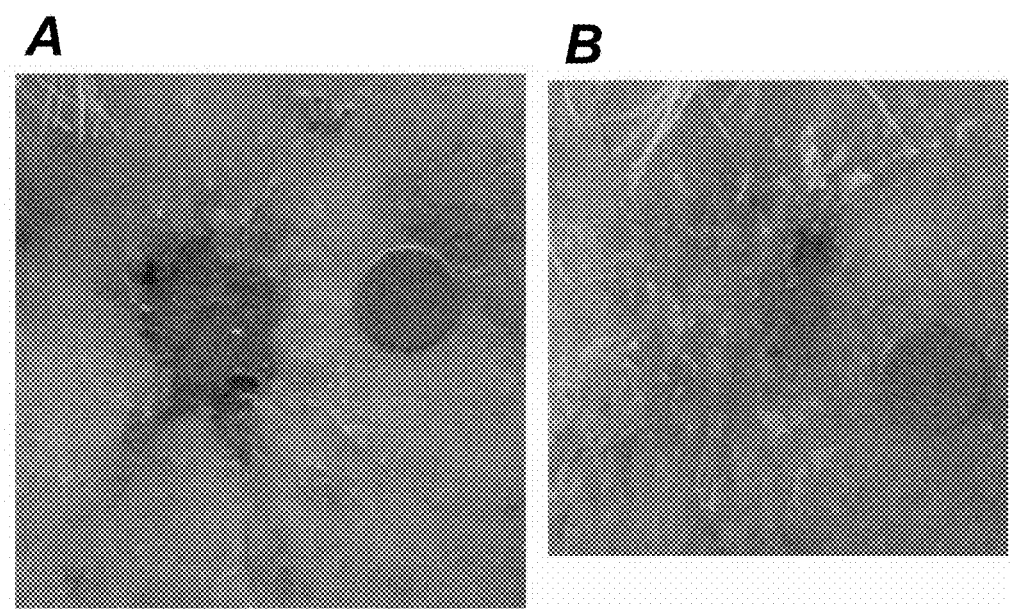
Fig. 5A-B

A
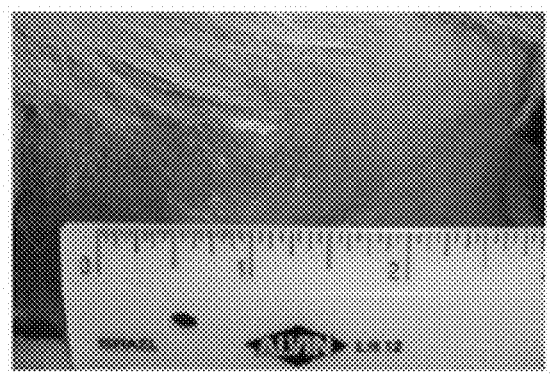
B
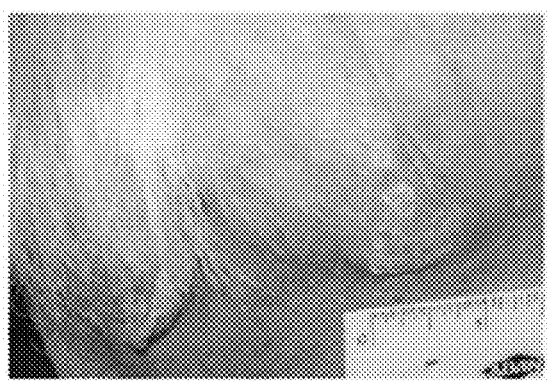
C
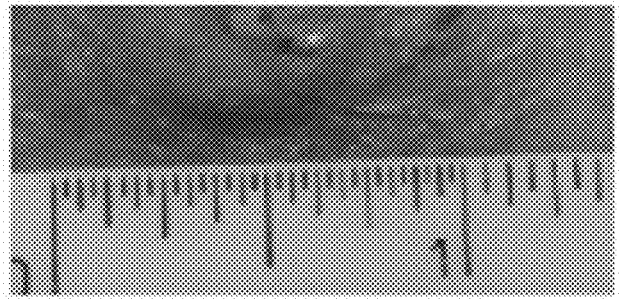
*Fig. 6A-C*

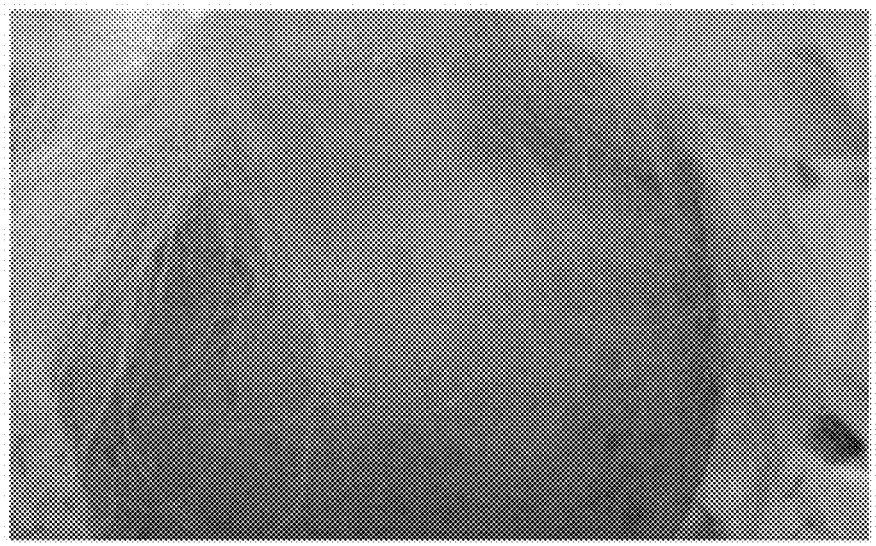
Fig. 7A-B

The general structure of a homologous procyanidin is 4→8 bonded, though there can be 4→6 branch points, and a gallic acid esterified at the 3 position.

US 10,232,007 B2

HIGH MOLECULAR WEIGHT POLYSACCHARIDE THAT BINDS AND INHIBITS VIRUS

CROSS-REFERENCE TO RELATED APPLICATIONS

This application is a continuation of U.S. non-provisional application Ser. No. 14/107,553, filed on Dec. 16, 2013, which is a continuation of U.S. non-provisional application Ser. No. 12/694,226, filed on Jan. 26, 2010, U.S. Pat. No. 8,629,121, issued Jan. 14, 2014, which claims the benefit of U.S. provisional application No. 61/206,197, filed Jan. 27, 2009, all of which are hereby incorporated by reference in their entirety (including the provisional application's appendix).

STATEMENT AS TO RIGHTS TO INVENTIONS MADE UNDER FEDERALLY SPONSORED RESEARCH AND DEVELOPMENT

This invention was made with government support under grant no. DE-FG09-93 ER-20097 awarded by the Department of Energy-funded Center for Plant and Microbial Complex Carbohydrates. The Government has certain rights in the invention.

FIELD OF THE INVENTION

The invention relates to a high molecular weight polysaccharide capable of binding to and inhibiting virus and related immunogenic compositions and methods.

BACKGROUND OF THE INVENTION

Extracts prepared from grape seed have been touted as having numerous health benefits, including antioxidant, anti-inflammatory, anti-bacterial, anti-viral, and anti-tumor activities. At least some of these effects have been attributed to flavonoid constituents of a hot water extract of grape seed. Nair et al., Clin Diagn Lab Immunol. (March 2002) 9(2): 470-476.

SUMMARY OF THE INVENTION

In certain embodiments, the invention provides a composition that binds to a virus and inhibits the virus, the composition including:
  an isolated polysaccharide comprising an arabinofuranosyl residue, a galactopyranosyl residue, and a galacturonic acid; and
  a catechin polymer;
wherein said composition is soluble in water; and
wherein said composition binds to a virus and reduces the infectivity or pathogenecity of said virus.

In certain embodiments, the invention provides a composition that binds to a virus and inhibits the virus, the composition including:
  an isolated polysaccharide including a arabinofuranosyl residue, a rhamnopyranosyl residue, a galactopyranosyl residue, a glucopyranosyl residue, a mannopyranosyl residue, and a galacturonic acid; and
  a non-carbohydrate aromatic polymer;
  wherein the composition includes about 40 to about 44 percent oxygen, about 44 to about 48 percent carbon, about 3 to about 6 percent hydrogen; and about 0.1 to about 1 percent nitrogen;
  wherein the composition is soluble in water; and
  wherein the composition binds to a virus and reduces the infectivity or pathogenecity of the virus.

The composition can include about 10 to about 30 weight percent polysaccharide and about 70 to about 90 weight percent catechin polymer. Although such a composition is less than 50 weight percent polysaccharide, this composition is still referred to herein as a "polysaccharide composition" or "polysaccharide" for ease of description.

In certain embodiments, the composition includes a component having a molecular weight greater than about 1 million Daltons. In certain embodiments, the composition includes a component having a molecular weight in the range of about 60,000 to about 100,000 Daltons. In some embodiments, the composition includes both components. In variations of these embodiments, the ratio of the amount of the component having a molecular weight greater than about 1 million Daltons to the amount of the component having a molecular weight in the range of about 60,000 to about 100,000 Daltons is about 95:5.

In particular embodiments, the composition does not include protein.

In exemplary compositions, the polysaccharide can include:
  about 30 to about 75 mole percent arabinose;
  about 0 to about 10 mole percent rhamnose;
  about 0 to about 5 mole percent xylose;
  about 0 to about 8 mole percent glucuronic acid;
  about 3 to about 36 mole percent galactouronic acid;
  about 0 to about 6 mole percent mannose;
  about 1 to about 20 mole percent galactose; and
  about 0 to about 13 mole percent glucose.

In other exemplary compositions, the polysaccharide can include:
  about 60 to about 66 mole percent arabinose;
  about 4.1 to about 4.5 mole percent rhamnose;
  about 2.2 to about 2.4 mole percent xylose;
  about 8.7 to about 9.7 mole percent galactouronic acid;
  about 2.3 to about 2.5 mole percent mannose;
  about 13.7 to about 15.1 mole percent galactose; and
  about 4.2 to about 4.6 mole percent glucose.

In certain embodiments, the compositions include:
  a terminally linked arabinofuranosyl residue (t-Araf);
  a 2-linked arabinofuranosyl residue (2-Araf);
  a 2-linked rhamnopyranosyl residue (2-Rhap);
  a 3-linked arabinofuranosyl residue (3-Araf);
  a terminally linked galactopyranosyl residue (t-Gal);
  a 5-linked arabinofuranosyl residue (5-Araf);
  a 3-linked glucopyranosyl residue (3-Glc) and/or a 2,4-linked rhamnopyranosyl residue (2,4-Rhap);
  a 2-linked glucopyranosyl residue (2-Glc);
  a 4-linked mannopyranosyl residue (4-Man);
  a 3,5-linked arabinofuranosyl residue (3,5-Araf);
  a 2,5-linked arabinofuranosyl residue (2,5-Araf);
  a 4-linked glucopyranosyl residue (4-Glc);
  a 2,3,5-linked arabinofuranosyl residue (3,5-Araf) and/or a 2,3,4-linked arabinopyranosyl residue (2,3,4-Arap);
  a 4-linked galactouronic acid (4-gal A);
  a 3,6-linked galactopyranosyl residue (3,6-Gal);
  a 2,3,4,6-linked mannopyranosyl residue (2,3,4,6-Man);
  a 2,3,4,6-linked galactopyranosyl residue (2,3,4,6-Gal) &2,3,4-linked galactouronic acid; and
  a 2,3,4,6-linked glucopyranosyl residue (2,3,4,6-Glc).

In specific examples of such embodiments, the polysaccharide includes:

the terminally linked arabinofuranosyl residue (t-Araf) includes about 14.2 to about 15.7 wt percent of the polysaccharide;

the 2-linked arabinofuranosyl residue (2-Araf) includes about 9.1 to about 10.08 wt percent of the polysaccharide;

the 2-linked rhamnopyranosyl residue (2-Rhap) includes about 0.3 wt percent of the polysaccharide;

the 3-linked arabinofuranosyl residue (3-Araf) includes about 3.0 to about 3.4 wt percent of the polysaccharide;

the terminally linked galactopyranosyl residue (t-Gal) includes about 2.0 to about 2.2 wt percent of the polysaccharide;

the 5-linked arabinofuranosyl residue (5-Araf) includes about 15.0 to about 16.6 wt percent of the polysaccharide;

the 3-linked glucopyranosyl residue (3-Glc) and/or 2,4-linked rhamnopyranosyl residue (2,4-Rhap) includes about 0.7 wt percent of the polysaccharide;

the 2-linked glucopyranosyl residue (2-Glc) includes about 1.1 to about 1.3 wt percent of the polysaccharide;

the 4-linked mannopyranosyl residue (4-Man) includes about 1.3 to about 1.5 wt percent of the polysaccharide;

the 3,5-linked arabinofuranosyl residue (3,5-Araf) includes about 6.6 to about 7.3 wt percent of the polysaccharide;

the 2,5-linked arabinofuranosyl residue (2,5-Araf) includes about 5.0 to about 5.6 wt percent of the polysaccharide;

the 4-linked glucopyranosyl residue (4-Glc) includes about 4.6 to about 5.0 wt percent of the polysaccharide;

the 2,3,5-linked arabinofuranosyl residue (3,5-Araf) and/or 2,3,4-linked arabinopyranosyl residue (2,3,4-Arap) includes about 25.7 to about 28.4 wt percent of the polysaccharide;

the 4-linked galactouronic acid (4-gal A) includes about 1.4 to about 1.6 wt percent of the polysaccharide;

the 3,6-linked galactopyranosyl residue (3,6-Gal) includes about 0.4 wt percent of the polysaccharide;

the 2,3,4,6-linked mannopyranosyl residue (2,3,4,6-Man) includes about 0.7 wt percent of the polysaccharide;

the 2,3,4,6-linked galactopyranosyl residue (2,3,4,6-Gal) &2,3,4-linked galactouronic acid includes about 2.0 to about 2.2 wt percent of the polysaccharide; and the 2,3,4,6-linked glucopyranosyl residue (2,3,4,6-Glc) includes about 2.1 to about 2.3 wt percent of the polysaccharide.

Polysaccharide compositions according to the invention can bind any virus, including, but not limited to a virus from a family selected from the group consisting of Adenoviridae, Picornaviridae, Reoviridae, Arenaviridae, Bunyaviridae, Coroanviridae, Herpesviridae, Orthomyxoviridae, Paramyxoviridae, Poxviridae Rhabdoviridae, Flaviviridae, and/or Retroviridae. In certain embodiments, the composition provides a NMR spectrum as shown in FIG. 3A.

Polysaccharide compositions can be formulated in a pharmaceutically acceptable excipient for administration to a subject. In particular embodiments, the composition is formulated as a unit dosage formulation. For example, the composition can be formulated in a delivery form selected from the group consisting of a tablet, a capsule, a lozenge, an ointment, a cream, a transdermal formulation (e.g., a patch), a gel, a nasal spray, a suppository, an injectable, and an implantable sustained-release formulation.

The invention also provides a method of preparing a composition that binds a virus. The method entails preparing a substantially homogeneous aqueous mixture or solution of plant material from one or more plants of the Vitaceae family; contacting the mixture with an ion exchange resin and recovering the colored product; and further purifying the colored product by removing low molecular weight components that can pass through a dialysis filter that generally passes molecules having a molecular weight of a $5 \times 10^5$ Daltons or less to produce a composition that binds a virus. The plant material can be from a grape plant, e.g., the plant material can include seed from a grape plant. In certain embodiments, the ion exchange resin includes an anion exchange resin. In variations of such embodiments, the method entails running the mixture through two sequential anion exchange columns. Further purification of the colored product can entail dialyzing or ultrafiltering the colored product. In certain embodiments, the further purification increases the concentration of the colored product by at least 10 fold. Thus, in an exemplary method, the ion exchange resin includes an anion exchange resin; and the further purification includes ultrafiltering or dialyzing the colored product to increase the concentration of the colored product by at least 10 fold. The invention also provides a composition that binds virus, wherein the composition is obtainable, or obtained, by any of the above-described preparation methods of the invention.

Another aspect of the invention is a method of inhibiting the infectivity and/or pathogenicity of a virus, the method including contacting the virus with a polysaccharide composition according to the invention. The virus can be any of those described above with respect to the binding characteristics of the polysaccharide compositions according to the invention. In particular embodiments, the composition is conveniently provided in a unit dosage form. In exemplary embodiments, the composition is administered to a mammal, such as, e.g., a human in need thereof. Administration can be by any route, such as oral administration, sub-lingual administration, topical administration, transdermal administration, nasal administration, rectal administration, injectable administration, and administration via an implant.

The invention additionally provides a method inhibiting the growth and/or proliferation of a cancer cell, by contacting the cancer cell with a polysaccharide composition of the invention. The cancer cell can be, for example, a solid tumor cell or a non-solid tumor cell. In certain embodiments, the cancer cell is a metastatic cancer cell. In particular embodiments, the cancer is bladder cancer, breast cancer, colon and/or rectal cancer, endometrial cancer, kidney cancer, leukemia, liver cancer, lung cancer, melanoma, non-Hodgkin lymphoma, ovarian cancer, pancreatic cancer, prostate cancer, skin cancer (non-melanoma), stomach cancer, or thyroid cancer. In certain embodiments, the composition is conveniently provided in a unit dosage form. In exemplary embodiments, the composition is administered to a mammal, such as, e.g., a human in need thereof. Administration can be by any route, such as oral administration, sub-lingual administration, topical administration, transdermal administration, nasal administration, rectal administration, injectable administration, and administration via an implant.

Another aspect of the invention is an immunogenic composition, wherein the composition includes a polysaccharide composition of the invention bound to a virus, such as one from a family selected from: Adenoviridae, Picornaviridae, Reoviridae, Arenaviridae, Bunyaviridae, Coroanviridae, Herpesviridae, Orthomyxoviridae, Paramyxoviridae, Poxviridae Rhabdoviridae, Flaviviridae, and Retroviridae. In particular embodiments, the immunogenic composition includes an adjuvant, such as, e.g., alum.

The invention also provides a method of inducing an immune response in a mammal. The method entails administering to the mammal an immunogenic composition according to the invention in an amount sufficient to induce an immune response. The immune response can, for example, be directed against one or more viruses from any of the families noted above. In specific embodiments, the method can include preparing monoclonal antibodies that bind to any of these viruses.

Another aspect of the invention is a method of ameliorating a symptom of aging in a subject in need thereof. The method entails administering to the subject an effective amount of a polysaccharide composition according to the invention, wherein said effective amount is sufficient to ameliorate a least one symptom of aging. Illustrative symptoms of aging that can be ameliorated by this method include hair loss, near vision loss due to aging, age spots, skin thinning and/or loss of elasticity, reduced hormone levels due to aging, loss of stamina due to aging, increased fat deposits, chronic joint and back pains, and/or age-related impairments in cognition. In particular embodiments, the composition is conveniently provided in a unit dosage form. In exemplary embodiments, the composition is administered to a mammal, such as, e.g., a human in need thereof. Administration can be by any route, such as oral administration, sub-lingual administration, topical administration, transdermal administration, nasal administration, rectal administration, injectable administration, and administration via an implant.

Another aspect of the invention is a method of detecting and/or quantifying a virus. This method entails contacting a sample with a polysaccharide composition of the invention under conditions suitable for the polysaccharide composition to bind any virus present in the sample; and detecting and/or quantifying binding to the polysaccharide composition.

The invention also provides a device that can be used in the detection method of the invention. The device includes a solid support having attached thereto a polysaccharide composition of the invention. Exemplary solid supports include a planar substrate, a bead, a capillary, a microchannel, and a syringe. In particular embodiments, the solid support can include a material selected from the group consisting of quartz, glass, plastic, metal, gel, and an aerogel.

Another aspect of the invention is a method of isolating one or more viruses from a sample. The method entails contacting the sample with the polysaccharide composition of the invention that is affixed to a substrate under conditions suitable for the polysaccharide composition to bind any virus present in the sample. The substrate is then washed to remove any unbound sample material.

In other embodiments, a polysaccharide composition described herein can be administered to a subject to ameliorate and/or reverse a symptom of aging. Symptoms of aging that can be ameliorated and/or reversed by this method include, but are not limited to, hair loss, near vision loss due to aging, age ("liver") spots, reduced hormone (e.g. estrogen or testosterone) levels due to aging, loss of stamina due to aging, increased fat deposits, chronic joint and back pains, age-related impairments in cognition and focus of thinking.

BRIEF DESCRIPTION OF THE DRAWINGS

FIG. 4A-C are photographs showing the effect of treating a human squamous cell carcinoma with a polysaccharide composition of the invention as described in Example 10. A shows the lesion as it appeared before treatment; B shows the lesion on treatment day 5; and C shows the lesion on treatment day 9. The blue dot in each photograph is ¼ inch in diameter.

FIG. 5A-B are photographs showing the effect of treating a human skin cancer in a male subject by oral administration of a polysaccharide composition of the invention as described in Example 11. A shows the lesion as it appeared before treatment; B shows the lesion after 20 oral treatments. The blue dot in each photograph is ¼ inch in diameter.

FIG. 6A-C are photographs showing the effect of treating a human squamous cell carcinoma in a female subject by oral administration of a polysaccharide composition of the invention as described in Example 11. A shows the lesion as it appeared on the morning of 7-27-08 (12 hours post-treatment); B shows the lesion in the evening of 7-28-08 (36 hours post-treatment); C shows the lesion on 8-1-08 (day 7 post-treatment).

FIGS. 7A-B are photographs showing hair restoration by oral administration of a polysaccharide composition of the invention to an 89-year-old male subject as described in Example 13. The picture in A was taken 2 weeks before the picture in B.

DETAILED DESCRIPTION

Figure 1:
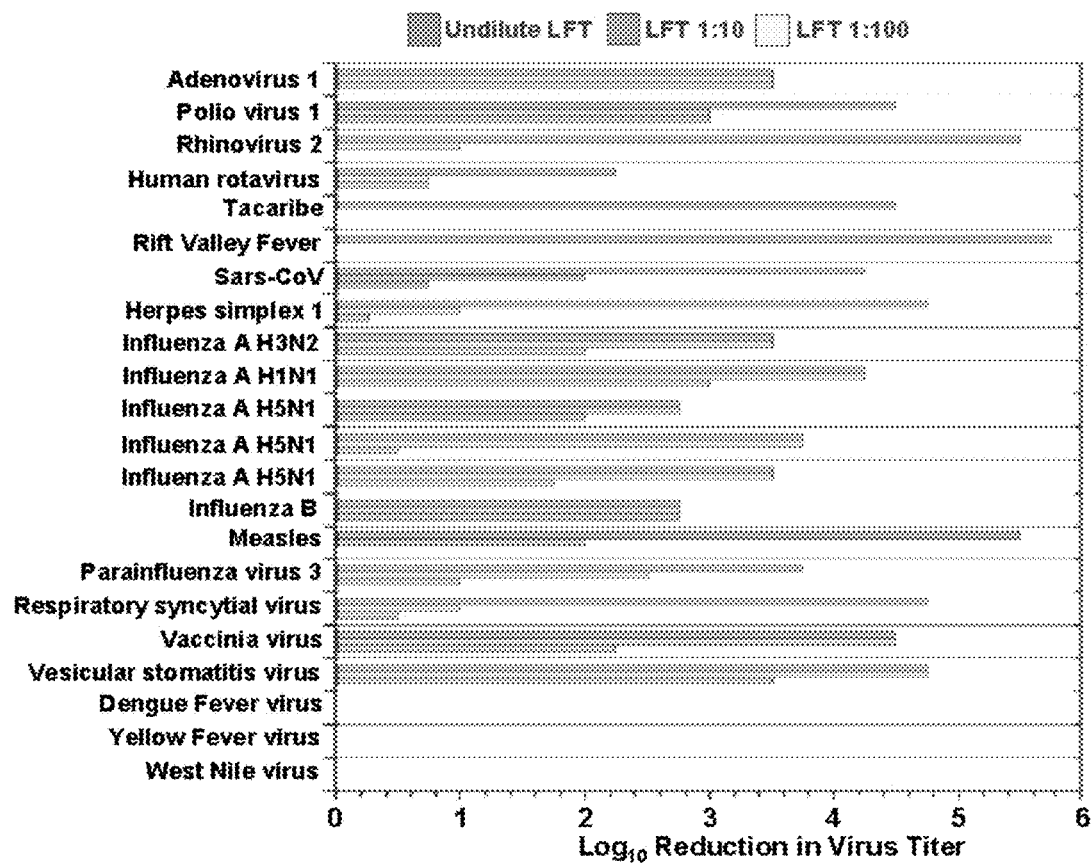
FIG. 1 shows a summary of the effects of three different concentrations of polysaccharide composition on virus infectivity. See Example 6. "LFT" refers to the polysaccharide composition of the invention prepared as described in Example 1. In each triplet of bars for each virus, the top bar is undiluted LFT, the middle bar is LFT 1:10, and the bottom bar is LFT 1:100.
Figure 2A:
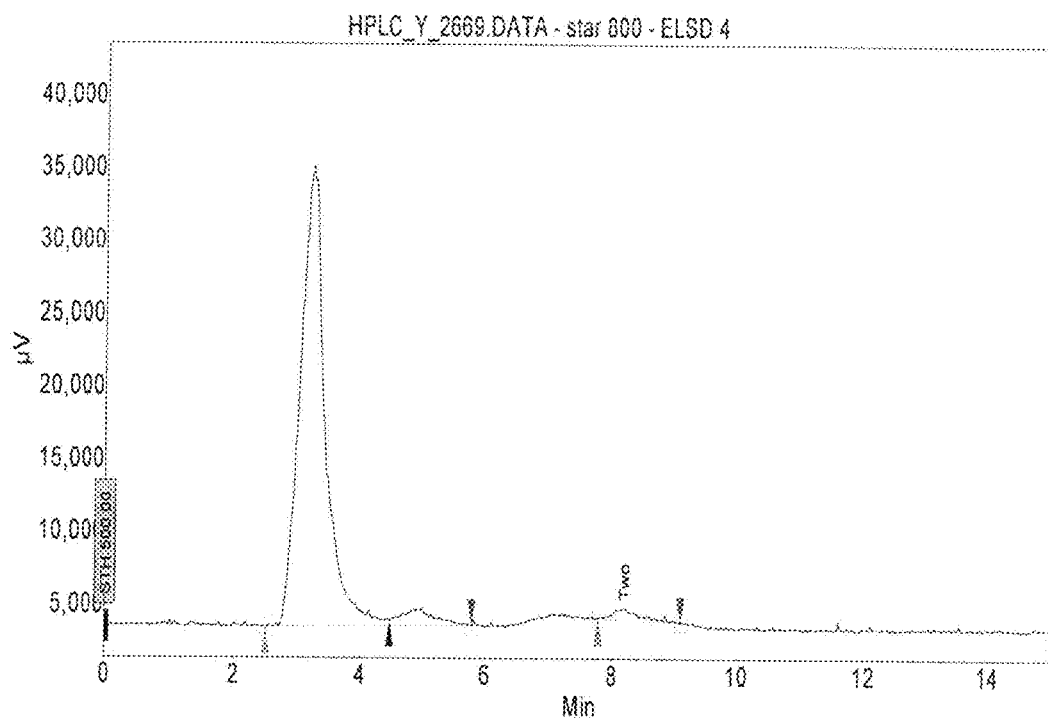
FIG. 2A-C shows three HPLC chromatograms that indicate that, when the polysaccharide composition binds virus, a component of the composition is released that is approximately 180,000 Daltons, and a larger molecular weight component remains bound to the virus.
Figure 2B:
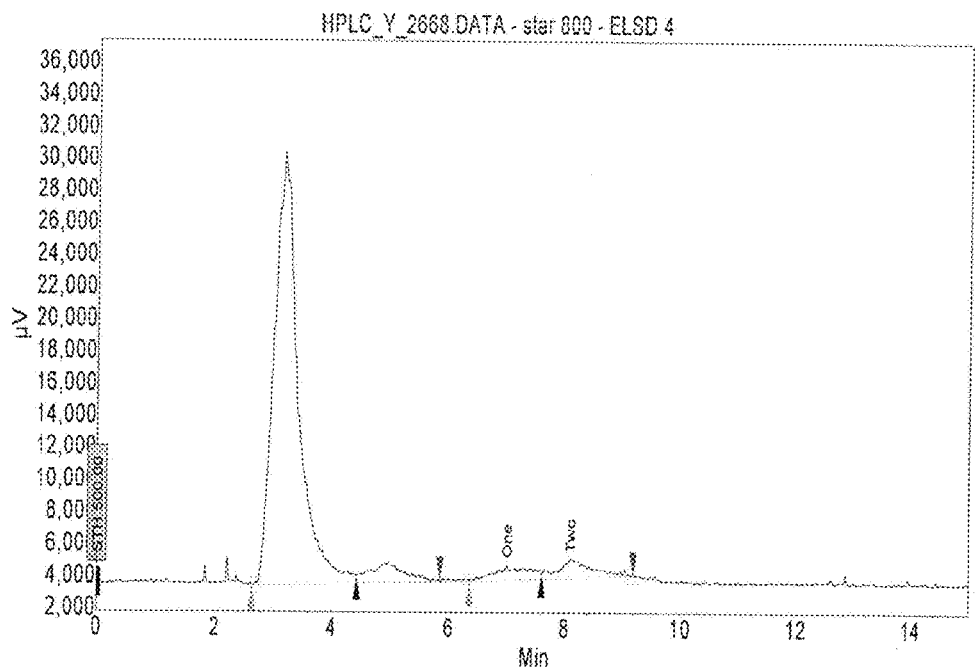
Figure 2C:
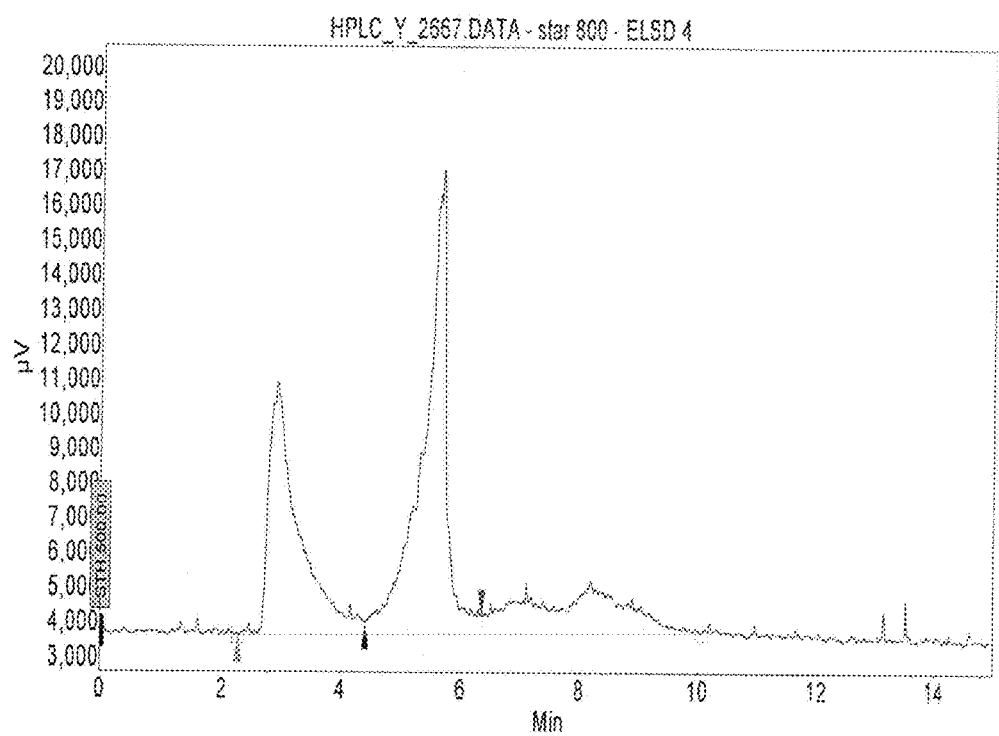

The invention relates to the discovery of a complex composition that consists of sugars and an aromatic polymer that can be obtained from plants, such as those in the genus *Vitis*, particularly the family Vitaceae, which are a family of dicotyledonous flowering plants including the grape and Virginia creeper. This composition has anti-viral and anti-cancer activities. The composition binds to viruses and virus-like structure, e.g., structure containing nucleic acid surrounded by a protein coat that protects the nucleic acid;

and may have an envelope (e.g., a lipid envelope) that surrounds the protein coat. Virus-like structures can include non-replicating and/or artificial viruses. The properties and use of the composition are discussed herein with respect to viruses for convenience, but those of skill in the art understand that these properties and many uses also apply to virus-like particles. The composition can be contacted with a virus to produce an immunogenic composition that induces an immune response against the virus. Viral binding can also be exploited to detect, isolate, filter, label, bind, inactivate, identify or quantify viruses.

I. High Molecular Weight Polysaccharide Composition

A. Characteristics

The composition of the invention ("polysaccharide composition") is characterized by a high molecular weight polysaccharide that is isolated by separating the composition from at least one other component(s) that is/are naturally present with the polysaccharide. One way of carrying out this separation is by passing aqueous mixture or solution of plant material from one or more plants of the Vitaceae family over an ion exchange resin and recovering the colored product. See Example 1.

In particular embodiments, isolated polysaccharide composition includes an arabinofuranosyl residue, a galactopyranosyl residue, and a galacturonic acid. The polysaccharide composition also includes a catechin polymer. In variations of these embodiments, the catechin polymer accounts for about 70 to about 90 weight percent of the composition, with about 10 to about 30 weight percent being polysaccharide.

In certain embodiments, the isolated polysaccharide composition includes an arabinofuranosyl residue, a rhamnopyranosyl residue, a galactopyranosyl residue, a glucopyranosyl residue, a mannopyranosyl residue, and a galacturonic acid. See Example 3. The polysaccharide composition also includes a non-carbohydrate aromatic polymer. See Example 2. Elemental analysis indicates that the composition comprises about 40 to about 44 percent oxygen, about 44 to about 48 percent carbon, about 3 to about 6 percent hydrogen, and about 0.1 to about 1 percent nitrogen. In one embodiment, the approximate elemental composition is 41.73 percent oxygen, 45.55 percent carbon, 4.48 percent hydrogen, and 0.37 percent nitrogen.

In particular embodiments, the polysaccharide composition comprises a component having a molecular weight greater than about 0.05 million Daltons and typically less than about 5 million Daltons. In certain embodiments, the composition includes a component having a molecular weight greater than about 1 million Daltons. In certain embodiments, the composition includes a component having a molecular weight in the range of about 60,000 to about 100,000 Daltons. In some embodiments, the composition includes both components. In variations of these embodiments, the ratio of the amount of the component having a molecular weight greater than about 1 million Daltons to the amount of the component having a molecular weight in the range of about 60,000 to about 100,000 Daltons is about 95:5. The polysaccharide composition generally does not contain protein, as determined by Bradford assay.

In exemplary compositions, the polysaccharide can include:
about 30 to about 75 mole percent arabinose;
about 0 to about 10 mole percent rhamnose;
about 0 to about 5 mole percent xylose;
about 0 to about 8 mole percent glucuronic acid;
about 3 to about 36 mole percent galacturonic acid;
about 0 to about 6 mole percent mannose;
about 1 to about 20 mole percent galactose; and
about 0 to about 13 mole percent glucose.

In particular embodiments, the polysaccharide composition is typically between about 7.5 and about 9.0 weight percent total carbohydrate, more specifically about 8 percent total carbohydrate. In certain embodiments, the glycosyl composition of the polysaccharide composition of the invention is:
about 60 to about 66 mole percent arabinose;
about 4.1 to about 4.5 mole percent rhamnose;
about 2.2 to about 2.4 mole percent xylose;
about 8.7 to about 9.7 mole percent galacturonic acid;
about 2.3 to about 2.5 mole percent mannose;
about 13.7 to about 15.1 mole percent galactose; and
about 4.2 to about 4.6 mole percent glucose,
as determined by combined gas chromatography/mass spectrometry (GC/MS) of the per-O-trimethylsilyl (TMS) derivatives of the monosaccharide methyl glycosides produced from the sample by acidic methanolysis. See Example 3.

Glycosyl linkage analysis was carried out by a modification of the method of Hakomori, in which the polysaccharide composition was depolymerized, reduced, and acetylated, and the resultant partially methylated alditol acetates (PMAAs) analyzed by gas chromatography-mass spectrometry (GC-MS) as described by York et al (1985) Methods Enzymol. 118:3-40. This analysis revealed that, in particular embodiments, the polysaccharide composition includes:
a terminally linked arabinofuranosyl residue (t-Araf);
a 2-linked arabinofuranosyl residue (2-Araf);
a 2-linked rhamnopyranosyl residue (2-Rhap);
a 3-linked arabinofuranosyl residue (3-Araf);
a terminally linked galactopyranosyl residue (t-Gal);
a 5-linked arabinofuranosyl residue (5-Araf);
a 3-linked glucopyranosyl residue (3-Glc) and/or a 2,4-linked rhamnopyranosyl residue (2,4-Rhap);
a 2-linked glucopyranosyl residue (2-Glc);
a 4-linked mannopyranosyl residue (4-Man);
a 3,5-linked arabinofuranosyl residue (3,5-Araf);
a 2,5-linked arabinofuranosyl residue (2,5-Araf);
a 4-linked glucopyranosyl residue (4-Glc);
a 2,3,5-linked arabinofuranosyl residue (3,5-Araf) and/or a 2,3,4-linked arabinopyranosyl residue (2,3,4-Arap);
a 4-linked galacturonic acid (4-gal A);
a 3,6-linked galactopyranosyl residue (3,6-Gal);
a 2,3,4,6-linked mannopyranosyl residue (2,3,4,6-Man);
a 2,3,4,6-linked galactopyranosyl residue (2,3,4,6-Gal) &2,3,4-linked galacturonic acid; and
a 2,3,4,6-linked glucopyranosyl residue (2,3,4,6-Glc).

In exemplary embodiments of the polysaccharide composition:
the terminally linked arabinofuranosyl residue (t-Araf) comprises about 14.2 to about 15.7 wt percent of the polysaccharide;
the 2-linked arabinofuranosyl residue (2-Araf) comprises about 9.1 to about 10.08 wt percent of the polysaccharide;
the 2-linked rhamnopyranosyl residue (2-Rhap) comprises about 0.3 wt percent of the polysaccharide;
the 3-linked arabinofuranosyl residue (3-Araf) comprises about 3.0 to about 3.4 wt percent of the polysaccharide;
the terminally linked galactopyranosyl residue (t-Gal) comprises about 2.0 to about 2.2 wt percent of the polysaccharide;
the 5-linked arabinofuranosyl residue (5-Araf) comprises about 15.0 to about 16.6 wt percent of the polysaccharide;

the 3-linked glucopyranosyl residue (3-Glc) and/or 2,4-linked rhamnopyranosyl residue (2,4-Rhap) comprises about 0.7 wt percent of the polysaccharide;

the 2-linked glucopyranosyl residue (2-Glc) comprises about 1.1 to about 1.3 wt percent of the polysaccharide;

the 4-linked mannopyranosyl residue (4-Man) comprises about 1.3 to about 1.5 wt percent of the polysaccharide;

the 3,5-linked arabinofuranosyl residue (3,5-Araf) comprises about 6.6 to about 7.3 wt percent of the polysaccharide;

the 2,5-linked arabinofuranosyl residue (2,5-Araf) comprises about 5.0 to about 5.6 wt percent of the polysaccharide;

the 4-linked glucopyranosyl residue (4-Glc) comprises about 4.6 to about 5.0 wt percent of the polysaccharide;

the 2,3,5-linked arabinofuranosyl residue (3,5-Araf) and/or 2,3,4-linked arabinopyranosyl residue (2,3,4-Arap) comprises about 25.7 to about 28.4 wt percent of the polysaccharide;

the 4-linked galacturonic acid (4-gal A) comprises about 1.4 to about 1.6 wt percent of the polysaccharide;

the 3,6-linked galactopyranosyl residue (3,6-Gal) comprises about 0.4 wt percent of the polysaccharide;

the 2,3,4-linked mannopyranosyl residue (2,3,4,6-Man) comprises about 0.7 wt percent of the polysaccharide;

the 2,3,4,6-linked galactopyranosyl residue (2,3,4,6-Gal) &2,3,4-linked galacturonic acid comprises about 2.0 to about 2.2 wt percent of the polysaccharide; and the 2,3,4,6-linked glucopyranosyl residue (2,3,4,6-Glc) comprises about 2.1 to about 2.3 wt percent of the polysaccharide. See Example 4.

In certain embodiments, the polysaccharide composition is soluble in water. In particular embodiments, the polysaccharide composition is very drying on the tongue and tastes like chalk.

The polysaccharide composition of the invention binds to viruses and reduces the infectivity or pathogenicity of the virus. Without being bound by any particular theory, the polysaccharide composition is believed to bind to a site that is conserved among viruses. Upon binding to virus, a high-molecular weight component of the polysaccharide composition attaches to the virus, and a 150,000-180,000 molecular weight component ("150,000 molecular weight spin off component") is released. In particular embodiments, the composition remains bound to virus for at least 10 days, indicating that the binding may be irreversible. Compositions according to the invention can bind enveloped, non-enveloped, RNA, and DNA viruses, including, for example, Adenoviridae, Picornaviridae, Reoviridae, Arenaviridae, Bunyaviridae, Coronaviridae, Herpesviridae, Orthomyxoviridae, Paramyxoviridae, Poxviridae Rhabdoviridae, Flaviviridae, and Retroviridae. See Example 6.

B. Preparation

The polysaccharide composition can be prepared from a suitable plant material, such as, for example, material from one or more plants of the Vitaceae family (e.g., grapes), the Ericaceae family (e.g., bilberries and blueberries), the Fabaceae family (e.g., peanuts), and the Polygonaceae (e.g., Japanese knotweed).

In particular embodiments, the plant is a grape plant and the material employed is in the seeds, the skin, or a combination of the two. "Grape seed extract" is commercially available from a variety of sources and can be employed to prepare a substantially homogeneous aqueous mixture or solution. For example, Spectrum Chemicals and Laboratory Products (Gardena, Calif.) sells grape seed extract percent powder G1273, which contain the seed and skin of *Vitis vinifera*. In accordance with certain embodiments, a 5 percent solution (25 gm/500 mL) of this powder in water can be prepared as described in Example 1. The solution can be filtered using a coarse filter paper (e.g., Whatman cat No 1213-185 18.5 cm circle) to remove any large particles.

The homogeneous aqueous mixture or solution is then subjected to ion exchange and the colored product is recovered. In certain embodiments, the ion exchange resin employed is an anion exchange resin, such as a weak base anion exchange resin. For example, a Dowex™ M-43 resin, sold by Dow Chemical can be employed. This resin is Styrene-DVB macroporous resin with tertiary amine functional groups, and it has the typical properties shown in Table A1. The polysaccharide of the invention can be eluted from this column using distilled water.

TABLE A1

Properties of Dowex ™ M-43 Resin

| Typical Physical and Chemical Properties | FB (Free Base) Form | Units |
|---|---|---|
| Total Exchange Capacity, min. | 1.55 | eq/L |
| Weak Base Capacity, min. | 1.35 | eq/L |
| Water Retention Capacity | 40-50 | % |
| Particle Size Distribution | | |
| Range | 300-1200 | μm |
| >1200 μm, max. (16 mesh) | <2 | % |
| <300 μm, max. (50 mesh) | <3 | % |

In particular embodiments, two ion exchange steps are carried out, e.g., the colored product recovered from a first ion exchange column is passed over a second ion exchange column. The second ion exchange resin can be the same as the first, for example the homogeneous aqueous mixture or solution can be run through two sequential anion exchange columns, as described in Example 1. In such embodiments, all of the colored eluate from the first column can be passed over a second, smaller column. In an exemplary embodiment, both columns include about 20 inches of resin, and the first is about 3 inches in diameter, while the second is 1.5 inches in diameter. A first fraction of the colored eluate from the second column can be discarded, for example, the first about 40 to about 60 percent by volume (e.g., 50%). A second fraction of the colored eluate is collected, for example about 40 to about 60 percent by volume (e.g., 50%) or collection can be continued until the color of the eluate becomes significantly lighter, e.g., almost clear. This second fraction can then be further processed to obtain the polysaccharide composition of the invention. In alternative embodiments, all of the colored eluate is collected from the second column and subjected to dialysis. See Example 1.

The colored product recovered after ion exchange can be concentrated, which can be carried out using any suitable concentration method, such as dialysis or ultrafiltration. In various embodiments, the colored product is concentrated by at least about 2-fold, at least about 5-fold, and at least about 10-fold.

In particular embodiments, the colored product recovered after ion exchange is further purified by removing low molecular weight material, e.g., material having a molecular weight of less than about 500,000 Daltons, less than about 750,000 Daltons, or less than about $10^6$ Daltons. Low molecular weight material can be removed by any suitable means, such as dialysis or ion trap. This removal step can be carried out before or after concentration, or can be carried out by a single step that accomplishes both concentration and removal of low molecular weight material.

II. Pharmaceutical Formulations

The polysaccharide compositions of this invention can be formulated in a pharmaceutically acceptable excipient, for example, for administration to an individual in accordance with the methods of inhibiting viral infectivity or pathogenicity or methods of inhibiting growth and/or proliferation of cancer cells, which are described below. Pharmaceutically acceptable excipients are described in Remington's Pharmaceutical Sciences (1980) 16th editions, Osol, ed., 1980. Pharmaceutically acceptable excipients can contain one or more physiologically acceptable compound(s) that act, for example, to stabilize the composition or to increase or decrease the absorption of the polysaccharide composition. A pharmaceutically acceptable excipient suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable excipient is an aqueous pH-buffered solution.

Other pharmaceutically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable excipient(s), including a physiologically acceptable compound depends, for example, on the route of administration of the polysaccharide composition.

Pharmaceutical formulations of the invention can be stored in any standard form, including, e.g., an aqueous solution or a lyophilized cake. If appropriate, i.e., for injectables, such formulations are typically sterile when administered to subjects. Sterilization of an aqueous solution is readily accomplished by filtration through a sterile filtration membrane. If the formulation is stored in lyophilized form, the formulation can be filtered before or after lyophilization and reconstitution.

In particular embodiments, the polysaccharide composition is formulated as a unit dosage formulation, i.e., a formulation that provides a specific dose of polysaccharide composition. The unit dosage formulation provides a therapeutically effective dose, or some fraction thereof, such that multiple doses can be taken to deliver a therapeutically effective dose that is sufficiently well tolerated by the subject that the potential benefits of the dose outweigh the risks.

Exemplary dosage formulations include a powder, a solution, a tablet, a capsule, a lozenge, an ointment, a cream, a transdermal formulation (e.g., a patch), a gel, a nasal spray, a suppository, an injectable, an implantable sustained-release formulation, a lipid complex, etc. In certain embodiments, one or more components of a solution can be provided as a "concentrate," e.g., in a storage container (e.g., in a premeasured volume) ready for dilution or in a soluble capsule ready for addition to a volume of water.

In various embodiments, the polysaccharide compositions described herein can be administered orally, in which case delivery can be enhanced by the use of protective excipients. This is typically accomplished either by complexing the polysaccharide composition with a composition to render it resistant to acidic and enzymatic hydrolysis or by packaging the agents in an appropriately resistant carrier, e.g. a liposome. Means of protecting agents for oral delivery are well known in the art (see, e.g., U.S. Pat. No. 5,391,377).

Examplary formulations for topical delivery include, but are not limited to, ointments and creams. Ointments are semisolid preparations which are typically based on petrolatum or other petroleum derivatives. Creams containing the selected polysaccharide composition, are typically viscous liquid or semisolid emulsions, often either oil-in-water or water-in-oil. Cream bases are typically water-washable and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base is preferably inert, stable, nonirritating, and nonsensitizing.

III. Methods of Inhibiting Viral Infectivity and/or Pathogenicity

A. In General

Polysaccharide compositions according to the invention can be employed as an anti-viral agent against viruses that infect plant or animal cells. Accordingly, another aspect of the invention is a method of inhibiting the infectivity and/or pathogenicity of a virus, which entails contacting the virus with a polysaccharide composition of the invention. As noted above, the polysaccharide composition binds and inhibits the infectivity of enveloped, non-enveloped, RNA, and DNA viruses, including, for example, Adenoviridae, Picornaviridae, Reoviridae, Arenaviridae, Bunyaviridae, Coroanviridae, Herpesviridae, Orthomyxoviridae, Paramyxoviridae, Poxviridae Rhabdoviridae, Flaviviridae, and Retroviridae.

The virus is generally contacted with polysaccharide composition under physiological conditions (e.g., 37° C.), typically before or during a period of contact with cells that the virus is capable of infecting. The duration of contact with the polysaccharide composition can vary, depending on the particular application of the method. The duration of contact can range from minutes to days or longer. For certain applications, the polysaccharide composition is typically contacted with virus for, e.g., about 10, about 20, about 30, about 40, or about 50 mins.; or about 1, about 3, about 6, about 12, about 18, or about 24 hours.

This method can be carried out in vitro, i.e., cell or tissue culture (see Example 6), or in vivo, i.e., in an organism. The cells/tissues can be derived from, or the organism can be, a plant or animal, e.g., a vertebrate, such as a bird or a mammal, and is preferably an animal having research or commercial value or value as pets, such as a mouse, rat, hamster, guinea pig, rabbit, cat, dog, chicken, pig, sheep, goat, cow, horse, as well as a monkey or other primate. In particular embodiments, human cells/tissues or a human subject is employed in the method.

For in vivo applications, the composition can be administered to a subject who is already infected with a virus, to treat the infection (i.e., therapeutic use) or to a subject at risk for infection (i.e., prophylactic use). In each case a route of administration is chosen so as to deliver the polysaccharide to a site containing, or likely to contain, virus. For example, in the case of an influenza virus, the polysaccharide composition can be administered as a nasal spray to an individual who may be at risk for contracting an influenza infection (e.g., a healthcare worker). Alternatively, the polysaccharide composition can be used in a vaginal barrier cream to prevent cervical herpes infections.

B. Administration

For in vitro applications, the polysaccharide composition can simply be added to virus prior to, or during contact with cells.

For in vivo applications, the polysaccharide compositions identified herein are useful for local or systemic administration, for example, oral, sub-lingual, topical, injectable (including intrathecal injection), systemic, nasal (or otherwise inhaled), rectal, or local administration, such as by aerosol or transdermally, for prophylactic and/or therapeutic treatment of one or more of the pathologies/indications described herein.

Elevated serum half-life can be maintained by the use of sustained-release "packaging" systems. Such sustained release systems are well known to those of skill in the art (see, e.g., Tracy (1998) *Biotechnol. Prog.* 14: 108; Johnson et al. (1996), *Nature Med.* 2: 795; Herbert et al. (1998), *Pharmaceut. Res.* 15, 357).

In certain embodiments, the polysaccharide compositions may also be delivered through the skin using conventional transdermal drug delivery systems, i.e., transdermal "patches" wherein the polysaccharide composition is typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir or may take some other form. The backing layer in these laminates, which serves as the upper surface of the device, preferably functions as a primary structural element of the "patch" and provides the device with much of its flexibility. The material selected for the backing layer is preferably substantially impermeable to the polysaccharide composition and any other materials that are present.

In certain embodiments, one or more polysaccharide compositions described herein are administered alone or in combination with one or more other therapeutics in implantable (e.g., subcutaneous) matrices, termed "depot formulations."

A major problem with standard drug dosing is that typical delivery of drugs results in a quick burst of medication at the time of dosing, followed by a rapid loss of the drug from the body. Most of the side effects of a drug occur during the burst phase of its release into the bloodstream. Secondly, the time the drug is in the bloodstream at therapeutic levels is very short; most is used and cleared during the short burst.

Drugs (e.g., the polysaccharide compositions described herein) imbedded in various matrix materials for sustained release can mitigate these problems. Drugs embedded, for example, in polymer beads or in polymer wafers have several advantages. First, most systems allow slow release of the drug, thus creating a continuous dosing of the body with small levels of drug. This typically prevents side effects associated with high burst levels of normal injected or pill-based drugs. Secondly, since these polymers can be made to release over hours to months, the therapeutic span of the drug is markedly increased. Often, by mixing different ratios of the same polymer components, polymers of different degradation rates can be made, allowing remarkable flexibility depending on the polysaccharide composition being used. A long rate of drug release is beneficial for people who might have trouble staying on regular dosage, such as the elderly, but also represents an ease of use improvement that everyone can appreciate. Most polymers can be made to degrade and be cleared by the body over time, so they will not remain in the body after the therapeutic interval.

Another advantage of polymer-based drug delivery is that the polymers often can stabilize or solubilize proteins, peptides, and other large molecules that would otherwise be unusable as medications. Finally, many drug/polymer mixes can be placed directly in the disease area, allowing specific targeting of the medication where it is needed without losing drug to the "first pass" effect. This is certainly effective for treating the brain, which is often deprived of medicines that can't penetrate the blood/brain barrier.

A wide variety of approaches to designing depot formulations that provide sustained release of a polysaccharide composition are known and are suitable for use in the invention. Generally, the components of such formulations are biocompatible and may be biodegradable. Biocompatible polymeric materials have been used extensively in therapeutic drug delivery and medical implant applications to effect a localized and sustained release. See Leong et al., "Polymeric Controlled Drug Delivery," Advanced Drug Delivery Rev., 1:199-233 (1987); Langer, "New Methods of Drug Delivery," Science, 249:1527-33 (1990); Chien et al., Novel Drug Delivery Systems (1982). Such delivery systems offer the potential of enhanced therapeutic efficacy and reduced overall toxicity.

Examples of classes of synthetic polymers that have been studied as possible solid biodegradable materials include polyesters (Pitt et al., "Biodegradable Drug Delivery Systems Based on Aliphatic Polyesters: Applications to Contraceptives and Narcotic Antagonists," Controlled Release of Bioactive Materials, 19-44 (Richard Baker ed., 1980); poly(amino acids) and pseudo-poly(amino acids) (Pulapura et al. "Trends in the Development of Bioresorbable Polymers for Medical Applications," J. Biomaterials Appl., 6:1, 216-50 (1992); polyurethanes (Bruin et al., "Biodegradable Lysine Diisocyanate-based Poly(Glycolide-co-.epsilon. Caprolactone)-Urethane Network in Artificial Skin," Biomaterials, 11:4, 291-95 (1990); polyorthoesters (Heller et al., "Release of Norethindrone from Poly(Ortho Esters)," Polymer Engineering Sci., 21:11, 727-31 (1981); and polyanhydrides (Leong et al., "Polyanhydrides for Controlled Release of Biopolysaccharide compositions," Biomaterials 7:5, 364-71 (1986).

Thus, for example, the polysaccharide composition can be incorporated into a biocompatible polymeric composition and formed into the desired shape outside the body. This solid implant is then typically inserted into the body of the subject through an incision. Alternatively, small discrete particles composed of these polymeric compositions can be injected into the body, e.g., using a syringe. In an exemplary embodiment, the polysaccharide composition can be encapsulated in microspheres of poly (D,L-lactide) polymer suspended in a diluent of water, mannitol, carboxymethylcellulose, and polysorbate 80. The polylactide polymer is gradually metabolized to carbon dioxide and water, releasing the polysaccharide composition into the system.

In yet another approach, depot formulations can be injected via syringe as a liquid polymeric composition. Liquid polymeric compositions useful for biodegradable controlled release drug delivery systems are described, e.g., in U.S. Pat. Nos. 4,938,763; 5,702,716; 5,744,153; 5,990, 194; and 5,324,519. After injection in a liquid state or, alternatively, as a solution, the composition coagulates into a solid.

One type of polymeric composition suitable for this application includes a nonreactive thermoplastic polymer or copolymer dissolved in a body fluid-dispersible solvent. This polymeric solution is placed into the body where the polymer congeals or precipitates and solidifies upon the dissipation or diffusion of the solvent into the surrounding body tissues. See, e.g., Dunn et al., U.S. Pat. Nos. 5,278,201; 5,278,202; and 5,340,849 (disclosing a thermoplastic drug delivery system in which a solid, linear-chain, biodegradable polymer or copolymer is dissolved in a solvent to form a liquid solution).

The polysaccharide composition can also be adsorbed onto a membrane, such as a silastic membrane, which can be implanted, as described in International Publication No. WO 91/04014. Other exemplary implantable sustained release systems include, but are not limited to Re-Gel®, SQ2Gel®, and Oligosphere® by MacroMed, ProLease® and Medisorb® by Alkermes, Paclimer® and Gliadel® Wafer by Guilford pharmaceuticals, the Duros implant by Alza, acoustic biSpheres by Point Biomedical, the Intelsite capsule by Scintipharma, Inc., and the like.

The polysaccharide composition can be co-administered with one or more additional agents that inhibit viral infectivity and/or pathogenicity by simultaneous administration or sequential administration.

Additional agents can be administered by a route that is the same as, or different from, the route of administration of the polysaccharide composition. Where possible, it is generally desirable to administer these agents by the same route of administration, preferably in the same formulation. However, differences in pharmacodynamics, pharmacokinetics, or other considerations may dictate the co-administration of the polysaccharide composition and additional agent(s) in separate formulations. Additional agents can be administered according to standard practice.

C. Dose

In particular embodiments, virus are contacted in vitro with an amount of polysaccharide composition effective to reduce infection of cells by about 25 percent, about 50 percent, about 75 percent, about 80 percent, about 90 percent, about 95 percent, about 96 percent, about 97 percent, about 98 percent, about 99 percent, or about 100 percent.

In in vivo applications, the compositions of this invention are administered, for example, to a subject in an amount sufficient (on average) to inhibit, by any of the percentages listed above, or prevent infectivity and/or pathogenicity of the virus. An amount adequate to accomplish this is defined as a "therapeutically effective dose." Amounts effective for this use will depend upon the severity of the condition and the general state of the subject's health. Single or multiple administrations of the compositions may be administered depending on the dosage and frequency as required and tolerated by the subject.

The concentration of polysaccharide composition can vary widely and will be selected primarily based on fluid volumes, viscosities, body weight and the like in accordance with the particular mode of administration selected and the subject's needs. In accordance with standard practice, the clinician can titer the dosage and modify the route of administration as required to obtain the optimal therapeutic effect. Generally, the clinician begins with a low dose and increases the dosage until the desired therapeutic effect is achieved. Starting doses for a given active agent can, for example be extrapolated from in vitro and/or animal data.

In particular embodiments, concentrations of active agent(s) will typically be selected to provide dosages ranging from about 0.1 or 1 mg/kg/day to about 300 mg/kg/day and sometimes higher. Typical dosages for an inhalant formulation of the polysaccharide composition can be about 1, about 3, about 5, about 10, about 15, about 20, about 25, about 30, about 35, about 40, about 45, about 50, about 55, about 60, about 65 and about 70 mg/kg/day, or any range having any of these values as an endpoint. Polysaccharide composition formulations can be administered in one or multiples doses a day. In some cases, one administration may be sufficient to achieve the desired results. Alternatively, polysaccharide composition can be administered over multiples days as needed. In certain embodiments, polysaccharide compositions of the invention can be administered in an intravenous (IV) drip at a dosage of about 10, about 15, about 20, about 25, about 30, about 35, about 40, about 45, about 50, about 75, about 100, about 125, about 150 about 175, about 200, about 250, about 300, and about 350 mg/kg/hour, or any range having any of these values as an endpoint. Treatment can be conducted, for example, over about 1 to about 8 hours, e.g., about 4 hours. It will be appreciated that such dosages may be varied to optimize a therapeutic regimen in a particular subject or group of subjects, and thus any of these values can represent the upper or lower limit of a suitable dosage range according to the invention.

In embodiments of the method in which an additional agent that inhibits viral infectivity and/or pathogenicity is co-administered with the polysaccharide composition, suitable doses of additional agents are known and can be adjusted by the clinician for co-administration with the polysaccharide composition.

The foregoing formulations and administration methods are intended to be illustrative and not limiting. It will be appreciated that, using the teaching provided herein, other suitable formulations and modes of administration can be readily devised.

IV. Methods of Inhibiting Growth and/or Proliferation of Cancer Cells

The invention also provides a method of inhibiting the growth and/or proliferation of a cancer cell. The method entails contacting the cell with a polysaccharide composition according to the invention. As used herein, the phrase "contacting the cell with a polysaccharide composition according to the invention" includes introducing this composition into the cellular environment such that the composition is in the proximity of the target cells.

The cell is generally contacted with polysaccharide composition under physiological conditions. The duration of contact with the polysaccharide composition can vary, depending on the particular application of the method. The duration of contact can range from minutes to days or longer. For certain applications, the polysaccharide composition is typically contacted with the cell for, e.g., about 30 mins.; or about 1, about 3, about 6, about 12, or about 24 hours. To kill cancer cells, the duration of contact is typically at least about 3 hours.

This method can be carried out in vitro, i.e., cell or tissue culture (see Example 8), or in vivo, i.e., in an organism. The cells/tissues can be derived from, or the organism can be an organism that is susceptible to cancer, including any of those described above with respect to viral inhibition. In particular embodiments, mammalian, particularly human, cells/tissues or a mammalian, particularly human, subject is employed in the method. The cell can be any type of cancer cell, i.e., any cell that displays a transformed phenotype (e.g., growth in soft agar) and/or uncontrolled proliferation. In particular embodiments, the cancer cell is a non-solid cancer cell (e.g., a leukemia or lymphoma cell). In particular embodiments, the cancer cell is a solid tumor cell. In certain embodiments, the cancer cell is a metastatic cancer cell. Any cancer cell can be inhibited by the polysaccharide composition of the invention, including bladder cancer, breast cancer, colon and/or rectal cancer, endometrial cancer, kidney cancer, leukemia, liver cancer, lung cancer, melanoma, non-Hodgkin lymphoma, ovarian cancer, pancreatic cancer, prostate cancer, skin cancer (non-melanoma), stomach cancer, and thyroid cancer.

For in vitro applications, the polysaccharide composition can simply be added to cells. The routes and considerations for in vivo administration are essentially as described above with respect to viral inhibition.

In particular embodiments, cancer cells are contacted in vitro in with an amount of polysaccharide composition effective to reduce growth and/or proliferation of cancer cells by about 50 percent, about 75 percent, about 80 percent, about 90 percent, about 95 percent, about 96 percent, about 97 percent, about 98 percent, about 99 percent, or about 100 percent. In preferred embodiments, the amount of polysaccharide composition employed is sufficient to kill the cancer cells.

In in vivo applications, the compositions of this invention are administered, for example, to a subject in an amount sufficient (on average) to inhibit cancer cell growth and/or proliferation, by any of the percentages listed above or to eradicate the cancer. An amount adequate to accomplish this is defined as a "therapeutically effective dose." Amounts effective for this use will depend upon the severity of the condition and the general state of the subject's health. Single or multiple administrations of the composition may be administered depending on the dosage and frequency as required and tolerated by the subject. General considerations for determining a suitable dosing regimen the polysaccharide composition are essentially as described above for viral inhibition.

In certain embodiments, an additional chemotherapeutic agent is co-administered with the polysaccharide composition, simultaneously or sequentially. Suitable doses of additional agents are known and can be adjusted by the clinician for co-administration with the polysaccharide composition.

The foregoing formulations and administration methods are intended to be illustrative and not limiting. It will be appreciated that, using the teaching provided herein, other suitable formulations and modes of administration can be readily devised.

V. Methods of Treating Pain and/or Inflammation

The invention also includes a method of using the polysaccharide composition of the invention to treat pain and/or inflammation. For example, the composition can be used to treat diseases characterized by a "hyperactivity" of the immune system and/or where the production of natural virus-like structures causes disease; examples include autoimmune diseases, e.g., rheumatoid arthritis, or other chronic inflammatory diseases. The method entails administering to a subject in need thereof, an effective amount of a polysaccharide composition according to the invention.

The subject of the method can be any organism in which it is desirable to treat pain and/or inflammation, including any of those described above with respect to viral inhibition. In particular embodiments, a mammalian, particularly a human, subject is employed in the method. In particular embodiments, the polysaccharide is applied topically to reduce pain experienced at or near the surface of the body.

In one embodiment, the subject suffers from inflammatory pain, which may be acute or chronic. A polysaccharide composition can be administered to reduce pain and/or inflammation. Examples of inflammation amenable to treatment by administering a polysaccharide composition of the invention include pain/inflammation due to trauma, such as cuts, stings (e.g., bee or wasp stings) or other reactions to venom (e.g., jellyfish), burn, sunburn; dermatitis; neuritis; mucositis; urethritis; cystitis; gastritis; pneumonitis; and collagen vascular disease.

In another embodiment, the subject suffers from neuropathic pain, which also may be acute or chronic. Examples of neuropathic pain amenable to treatment by administering a polysaccharide composition of the invention include pain due to conditions such as, e.g., neuralgia, causalgia (complex regional pain syndrome type II), diabetes, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, anti-viral therapy, AIDS, AIDS therapy, post-polio syndrome, and post-herpetic neuralgia. Neuropathic pain arising from, e.g., trauma, surgery, amputation, toxin, and/or chemotherapy can also be treated using the antagonists of the invention.

In particular embodiments, the subject suffers from a generalized pain disorder, such as, e.g., fibromyalgia, irritable bowel syndrome, and/or temporomandibular disorders.

Other indications for the method of the invention include allodynia, migraine, atypical facial pain, back pain, arthritic pain, sports injury pain, pain related to infection (e.g. HIV), labor pain, post-operative pain, conditions associated with visceral pain, angina, and urinary bladder incontinence (e.g. urge incontinence).

The routes and considerations for administration are essentially as described above with respect to viral inhibition. For topical administration, any suitable topical formulation (e.g., as described above) containing a polysaccharide of the invention is simply applied to the skin over the region affected by the pain and/or inflammation. The polysaccharide composition is present in the topical formulation in an amount sufficient to reduce pain and/or inflammation. The number of applications per day will depend upon a number of factors, including the type of formulation employed and the activities of the subject after application (i.e., if the subject must wash the area frequently, the polysaccharide composition may need to be reapplied more frequently.

The foregoing formulations and administration methods are intended to be illustrative and not limiting. It will be appreciated that, using the teaching provided herein, other suitable formulations and modes of administration can be readily devised.

VI. Immunogenic Compositions and Methods of Inducing an Immune Response

In other embodiments, the invention provides an immunogenic composition, said which includes a polysaccharide composition of the invention bound to a virus. The polysaccharide composition can be bound to the virus as described above with respect to viral inhibition. Suitable viruses include any to which the polysaccharide composition binds, e.g., enveloped, non-enveloped, RNA, and DNA viruses, including, for example, Adenoviridae, Picornaviridae, Reoviridae, Arenaviridae, Bunyaviridae, Coroanviridae, Herpesviridae, Orthomyxoviridae, Paramyxoviridae, Poxviridae Rhabdoviridae, Flaviviridae, and Retroviridae.

The viral-polysaccharide complex is employed at the desired degree of purity and at a sufficient concentration to induce an immune response and is typically mixed with a pharmaceutically acceptable excipient. In particular embodiments, the immunogenic composition is formulated for injection, e.g., intramuscular, intradermal, or subcutaneous injection, although other routes of administration, including oral and intranasal, are contemplated as well. Suitable carriers for injection include sterile water, but preferably are physiologic salt solutions, such as normal saline or buffered salt solutions (e.g., phosphate-buffered saline or ringer's lactate).

Immunogenic compositions according to the invention contain an adjuvant, although this is not essential. Useful adjuvants include QS21 (*Quillaja saponaria*, commercially available from Cambridge Biotech, Worcester, Mass.), which stimulates cytotoxic T-cells, and alum (aluminum hydroxide adjuvant). Formulations with different adjuvants that enhance cellular or local immunity can also be used. In particular, immunopotentiators such as cytokines can be included in the immunogenic composition. Examples of suitable immunopotentiating cytokines include interleukins, such as interleukin-2 (IL-2) and interleukin-12 (IL-12), and tumor necrosis factor-alpha (TNF-α).

Additional excipients that can be present in the immunogenic composition include low molecular weight polypeptides (less than about 10 residues), proteins, amino acids, carbohydrates including glucose or dextrans, chelating agents such as EDTA, and other excipients that stabilize the polysaccharide composition and/or the virus and/or the complex or inhibit growth of microorganisms.

Preferably, any virus in the immunogenic composition has been inactivated, for example, by binding to the polysaccharide composition of the invention, as described above with respect to viral inhibition. Suitable relative amounts of polysaccharide composition and virus to achieve viral inactivation can be determined from Examples 5 and 7, or empirically, by carrying out studies such as those described in these examples.

Exemplary immunogenic compositions according to the invention can include virus in a range of approximately $10^6 TCID_{50}$ to approximately $10^3 TCID_{50}$ depending on the route of administration of virus. ("TCID" refers to the "tissue culture infective dose," which is that amount of a pathogenic agent that will produce pathological change when inoculated on tissue cultures; $TCID_{50}$, refers to the amount that produces a pathological change in 50% of all cell cultures). Adjuvants or other components are used at concentrations in accordance with standard practice or at concentrations empirically determined to provide the desired effect(s).

The amount of immunogenic composition administered is generally one sufficient to elicit a measurable immune response, such as, e.g., a neutralizing antibody response, increase in interferon, increase in natural killer cell activity and/or survival of a lethal infection. Depending on formulation and route of administration, such response(s) can be achieved after one immunization or after one or more booster immunizations, following an initial immunization. Where the immune response is an antibody response, neutralizing or otherwise, antibodies induced by the immunogenic composition can be used in a diagnostic to detect the virus strain used in the immunogen or to affinity-purify such virus or to inactivate such virus.

In particular embodiments, the dosing regimen is sufficient to elicit an in vivo protective immune response, i.e., one in which an organism is protected from homologous viral challenge (i.e., challenge with the same viral strain as that included in the immunogenic composition). Any animal that mounts an immune response to the viral-polysaccharide composition-viral complex immunogen can be the subject of an immunization method according to the invention, including any of those described above with respect to viral inhibition. In particular embodiments, mammalian, particularly human, subjects are employed in the method. Suitable subjects can be seronegative or seropositive for the virus strain included in the immunogen. In the case of seronegative subjects, the dosing regimen will generally be designed to elicit a protective immune response, such that the risk of infection upon subsequent exposure to the virus is reduced by about 25 percent, about 50 percent, about 75 percent, about 80 percent, about 90 percent, about 95 percent, about 96 percent, about 97 percent, about 98 percent, about 99 percent, about 100 percent, or by a range having endpoints defined by any of the above values. In the case of seropositive subjects, the dosing regimen will generally be designed to reduce a measure of infection, such as, e.g., viral load, by about these same percentages.

In preferred embodiments, the dosing regimen is sufficient to elicit an in vivo protective immune response to heterologous viral challenge (i.e., challenge with a different strain of the type of virus included in the immunogenic composition). The regimen may vary depending on the virus, and the determination of a suitable regimen can be determined by one of skill in the art. In some cases, it may be advantageous to boost, e.g., annually or biannually after protection has be achieved. In addition, one or more immune responses, e.g., neutralizing antibody levels, can be assayed and the regimen adjusted accordingly.

VII. Methods of Ameliorating Symptoms of Aging

Another aspect of the invention is a method of ameliorating a symptom of aging in a subject in need thereof. The method entails administering to the subject an effective amount of a polysaccharide composition according to the invention, wherein the effective amount is sufficient to ameliorate a least one symptom of aging.

The subject of the method can be any organism in which it is desirable to treat pain and/or inflammation, including any of those described above with respect to viral inhibition. In particular embodiments, a mammalian, particularly a human, subject is employed in the method. Illustrative symptoms of aging that can be ameliorated by this method include, but are not limited to, hair loss, near vision loss due to aging, age spots, skin thinning and/or loss of elasticity, reduced hormone levels due to aging, loss of stamina due to aging, increased fat deposits, chronic joint and back pains, and/or age-related impairments in cognition.

The routes and considerations for administration are essentially as described above with respect to viral inhibition. The number of doses per day will depend upon a number of factors, including the type of formulation employed and the route of administration.

The foregoing formulations and administration methods are intended to be illustrative and not limiting. It will be appreciated that, using the teaching provided herein, other suitable formulations and modes of administration can be readily devised.

VIII. Methods and Devices for Detecting/Quantifying Virus

The invention also provides a method of detecting and/or quantifying a virus. This method entails contacting a sample with a polysaccharide composition of the invention and detecting and/or quantifying binding to said composition. This method is useful for assessing a sample for the presence and/or amount of a virus and can be employed in identifying a virus.

A. Sample Collection and Processing

The assay methods of the invention can be carried out on any sample suspected of containing a virus, but are generally carried out on biological samples derived from a plant or animal (including any of those described herein), preferably a mammal, and more preferably a human. Convenient samples include, for example, tissue, blood, serum, plasma, urine, and saliva.

The sample may be pretreated as necessary by dilution in an appropriate buffer solution or concentrated, if desired. Any of a number of standard aqueous buffer solutions, employing any of a variety of buffers, such as phosphate, Tris, or the like, at physiological pH, can be used.

B. Assaying for Virus

Virus can be detected and quantified by assaying binding to the polysaccharide composition using any of a number of binding assay formats well known to those of skill in the art.

In particular embodiments, virus is detected and/or quantified in the biological sample using any of the available immunoassay formats, in which the anti-analyte antibody is replaced by the polysaccharide composition of the invention (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. Thus, the polysaccharide composition of the invention can be employed as a capture agent for a virus of interest (e.g., any of those described here). Polysaccharide compositions according to the invention can be affixed to a solid phase via any available means for immobilizing polysaccharides, such as the 2-amino-methyl N,O-hydroxyethyl spacer described by Bohorov, O. et al. (2006) Glycobiology 16(12):21C-27C, which is hereby incorporated by reference in its entirety; see also Kamitani, R. et al. (2007) Bulletin of the Chemical Society of Japan 80(9):1808-1813 (describing the attachment of carbohydrates to polymer surfaces), which is hereby incorporated by reference in its entirety; U.S. Pat. No. 7,241,453, issued to Engel et al. on Jul. 10, 2007 (discussing the production of anti-microbial surfaces through the attachment of carbohydrates), which is hereby incorporated by reference in its entirety; Weiping, Q et al. (1999) J. Inclusion Phenomena and Macrocyclic Chemistry 35(1-2) (describing the attachment of oxidized carbohydrates to other moieties), which is hereby incorporated by reference in its entirety; corninfo.p-s.uci.edu/writings/surfacechem.html (describing the non-covalent attachment of carbohydrates to metal surfaces); Moritz, B. B. et al. (2005) ChemBioChem 6(6): 1007-1015) (describing the attachment of carbohydrates to glass surfaces), which is hereby incorporated by reference in its entirety; microarrays.ca/support/emerg_tech_docs/CarbArrays_July2007.pdf (describing the attachment of carbohydrates to glass surfaces); Lee, J-C. et al. (2006) Angewandte Chemie International Ed. 45:2753-57 (describing the use of a photocleavable linker to reversibly attach carbohydrates to polymer surfaces), which is hereby incorporated by reference in its entirety.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). The use of an anti-viral antibody as the labeled detection agent will aid in the identification and/or quantification of specific viruses. In other embodiments, the labeled detection agent can be a labeled form of the polysaccharide composition of the invention. Such embodiments would permit the detection and/or quantification of virus, but not its identification, since the polysaccharide composition does not distinguish between different types of virus.

Preferred immunoassays for detecting the target polypeptide(s) are either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled virus is added to the sample, and the sample is then contacted with a capture agent. The amount of labeled virus bound to the antibody is inversely proportional to the concentration of virus present in the sample.

The assays of this invention are scored (as positive or negative or quantity of analyte) according to standard methods well known to those of skill in the art. The particular method of scoring will depend on the assay format and choice of label. For example, an assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration.

C. Solid Phase

For embodiments of the invention that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, quartz, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as a planar substrate, e.g., films, sheets, or plates, or they may be coated onto, bonded, or laminated to appropriate inert carriers, such as paper, glass, plastic films, fabrics, or the like.

The porous structure of nitrocellulose has excellent absorption and adsorption qualities for a wide variety of reagents including monoclonal antibodies. Nylon also possesses similar characteristics and also is suitable.

Porous solid phases useful in the invention can be in the form of sheets of thickness from about 0.01 to 0.5 mm, e.g., about 0.1 mm. The pore size may vary within wide limits, and is preferably from about 0.025 to about 15 microns, especially from about 0.15 to about 15 microns.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute a bead, e.g., a microparticle. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods of the present invention can be adapted for use in systems that utilize microparticle technology including automated and semi-automated systems wherein the solid phase comprises a microparticle. Such systems include those described in pending U.S. App. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). Other possible supports for assay of the invention include capillaries, microchannels, and syringes, etc.

The capture agent can be attached to the solid phase by adsorption on the porous material, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase material or onto microparticles which then are retained by a solid phase material. Ion capture procedures for immobilizing an immobilizable reaction complex with a negatively charged polymer, described in U.S. App. No. 150,278, corresponding to EP Publication No. 0326100, and U.S.App. No. 375,029 (EP Publication No. 0406473), can be employed according to the present invention to affect a fast solution-phase immunochemical reaction. In these procedures, an immobilizable reaction complex is separated from the rest of the reaction mixture by ionic interactions between the negatively charged polyanion/immune complex and the previously treated, positively charged porous matrix and detected by using any of a number of signal-generating systems, including, e.g., chemiluminescent systems, as described in U.S. App. No. 921,979, corresponding to EPO Publication No. 0 273,115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl] aminobenzoate), and SMPB (succinimidyl 4-[1maleimidophenyl] butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. App. No. 150,278, filed Jan. 29, 1988, and U.S. App. No. 375,029, filed Jul. 7, 1989, each of which is incorporated herein by reference.

Other considerations affecting the choice of solid phase include the ability to minimize non-specific binding of labeled entities and compatability with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

D. Labeling Systems

As discussed above, many assays according to the invention employ a labeled detection agent.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, texas red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

E. Formats

The assays of the invention can be conducted using any format known in the art.

1. Fluorescence Polarization Immunoassay (FPIA)

In an exemplary embodiment, a fluorescent label is employed in a fluorescence polarization immunoassay (FPIA) according to the invention. Generally, fluorescent polarization techniques are based on the principle that a fluorescent label, when excited by plane-polarized light of a characteristic wavelength, will emit light at another characteristic wavelength (i.e., fluorescence) that retains a degree of the polarization relative to the incident light that is inversely related to the rate of rotation of the label in a given medium. As a consequence of this property, a label with constrained rotation, such as one bound to another solution component with a relatively lower rate of rotation, will retain a relatively greater degree of polarization of emitted light than when free in solution.

This technique can be employed in assays according to the invention, for example, by selecting reagents such that binding of the fluorescently labeled entities forms a complex sufficiently different in size such that a change in the intensity light emitted in a given plane can be detected.

Fluorophores useful in FPIA include fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. Examples of commercially available automated instruments with which fluorescence polarization assays can be conducted include: IMx® system, TDx® system, and TDxFLx™ system (all available from Abbott Laboratories, Abbott Park, Ill.).

2. Scanning Probe Microscopy (SPM)

The use of scanning probe microscopy (SPM) for assays also is a technology to which the immunoassay methods of the present invention are easily adaptable. In SPM, in particular, in atomic force microscopy, the capture agent is affixed to a solid phase having a surface suitable for scanning. The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the biological sample is contacted with the solid phase, and a scanning probe microscope is used to detect and quantify solid phase-affixed complexes. The use of SPM eliminates the need for labels which are typically employed in immunoassay systems. Such a system is described in U.S. App. No. 662,147, which is incorporated herein by reference.

3. MicroElectroMechanical Systems (MEMS)

Assays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

4. Electrochemical Detection Systems

In other embodiments, assays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical assays using PAPP volumes ranging from 20 .mu.l to 360 µL have been reported previously. In capillary assays with electrochemical detection, the lowest detection limit reported thus far is 3000 molecules of mouse IgG using a volume of 70 µL and a 30 min or 25 min assay time.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

IX. Methods of Isolating Virus from a Sample

The invention also encompasses the use of polysaccharide compositions according to the invention for isolating virus from a sample. As used herein, the term "isolating" refers to separating a desired component (in this case, one or more viruses) from one or more other components that are naturally present with the virus in the sample. This method exploits the capacity of the polysaccharide composition to bind viruses. Accordingly, the method entails contacting the sample with the polysaccharide composition of the invention, wherein the polysaccharide composition is affixed to a substrate, under conditions suitable for the polysaccharide composition to bind any virus present in the sample. The substrate is then washed to remove unbound sample material.

The sample can be any type of sample, including, but not limited to, a biological sample, such as any of those described herein. The substrate can be any substrate capable of binding the polysaccharide composition, including any of those described herein. In particular embodiments, the substrate is a resin, such as those used for immunoaffinity chromatography. The sample can be contacted with the substrate to allow any virus present to bind to the substrate-affixed polysaccharide composition. In particular embodiments, the polysaccharide composition is reversibly affixed to the substrate. Unbound material can be eluted from the column by washing with water or another wash solution which is designed to remove at least one component that naturally present in the sample. Bound virus can then be recovered, for example, by releasing the virus bound-polysaccharide composition from the substrate. Any suitable means for reversibly attaching polysaccharides to a substrate can be employed. See, e.g., Lee, J-C. et al. (2006) Angewandte Chemie International Ed. 45:2753-57 (describing the use of a photocleavable linker to reversibly attach carbohydrates to polymer surfaces), which is hereby incorporated by reference in its entirety.

In other embodiments, after viral binding to a solid phase-affixed polysaccharide composition of the invention. The bound virus(es) can be detected and quantified as described above.

As methods for isolating a component from a mixture, based the component's binding capacity are well known, the selection of a suitable format, substrate, and wash buffer for using the polysaccharide composition to isolate virus is within the level of skill in the art.

EXAMPLES

The following examples are offered to illustrate, but not to limit the claimed invention.

Example 1

Preparation of Polysaccharide Composition

A polysaccharide composition of the invention was prepared using seed extract (Spectrum Grape Seed Extract 95% Powder G1273 in the 25 kg size) according to the following protocol.

(1) Prepare a 5% solution (25 gm/500 cc) in distilled water by mixing with a magnetic stirring rod while slowly adding powder so as not to form surface clumps. Prepare 1000 mL at a time on the Nuova Stir Plate by Thermolyne with the speed set at 8.

(2) Vigorously mix/shake the 5% solution.

(3) Filter the solution with coarse filter paper. Use 4 papers/500 mL; pour 25% into each filter paper (Whatman cat No 1213-185 18.5 cm circle) and then pool the filtrates.

(4) For anion exchange, plug the bottom of a column (3.25 inch diameter, 24 inches long, number 4 stopcock) with glass wool and Dowex™ M-43 resin (Dow Chemical) saturated in distilled water to fill the column leaving 4 inches to the top free. Prepare the column by back-flow washing with distilled water so the resin is not packed too tightly in any one area). Load the filtrate obtained in step (3) onto the column gently so as not to disturb the resin. Elute with distilled water and collect all of the colored material.

(5) Take all colored material from the first column and pass it onto the second smaller column (1.5 inch diameter, 24 inches long) filled with the same resin; elute with distilled water. Collect all the colored material again. This gives a solution that is almost pure high molecular weight polysaccharide composition of the invention.

(6) The polysaccharide composition can be further purified by removing all the low molecular weight material (less than half a million Daltons) by either dialysis or by using an ion trap or any other means.

(7) The polysaccharide composition can be run through a micropore filter to ensure that it is sterile before putting it into glass ampules or large vacuum bottles, for storage as the polysaccharide composition deteriorates when exposed to air.

Example 2

NMR Spectroscopy of Polysaccharide Composition

Polysaccharide composition prepared as described in Example 1 was subjected to NMR spectroscopy.

Methods

NMR Spectroscopy

The sample was exchanged into $D_2O$ by repeated addition and concentration of $D_2O$ (99.9% D) on a rotary evaporator (add 30 mL, evaporate to 2 mL, repeat 6 times). 1-D proton (FIG. 3A) and 2-D gradient enhanced COSY, TOCSY and NOESY NMR spectra (FIGS. 3B-3D) were acquired on a Varian (nova-500 MHz spectrometer at 343 K (70° C.) using standard Varian pulse sequences. Proton chemical shifts are given relative to 2,2-Dimethyl-2-silapentane-5-sulfonic acid (DSS; δ=0.00 ppm) and measured against the HDO signal (δ=4.31 ppm).

Isolation of Non-Carbohydrate Polymer by Methanolysis

Freeze-dried sample (6 mg) was suspended in 1 mL 1 M HCl in MeOH and the mixture heated to 80° C. for 6 h in a sealed test tube. After cooling to room temperature, 1 mL $H_2O$ was added and the methanol was removed by passing a stream of air over the solution. As the methanol evaporated, a thick, red precipitate formed, which was collected by centrifugation. The pellet was washed with water 3 times, and then suspended in 0.7 mL $H_2O$. Upon addition of 5μL M NaOH the solid dissolved in the water and the resulting solution was freeze-dried.

Results

The proton spectrum (FIG. 3A) displays at least 10 different anomeric protons, a complex ring region between 3.6 and 4.8 ppm, an intense singlet at 3.8 ppm, likely due to presence of a methyl ester, and a broad peak between 6.2 and 7.5 ppm. A non-carbohydrate polymer is shown by the broad peak around 7 ppm. This polymer is probably the source of the color in the sample.

Figure 3A:
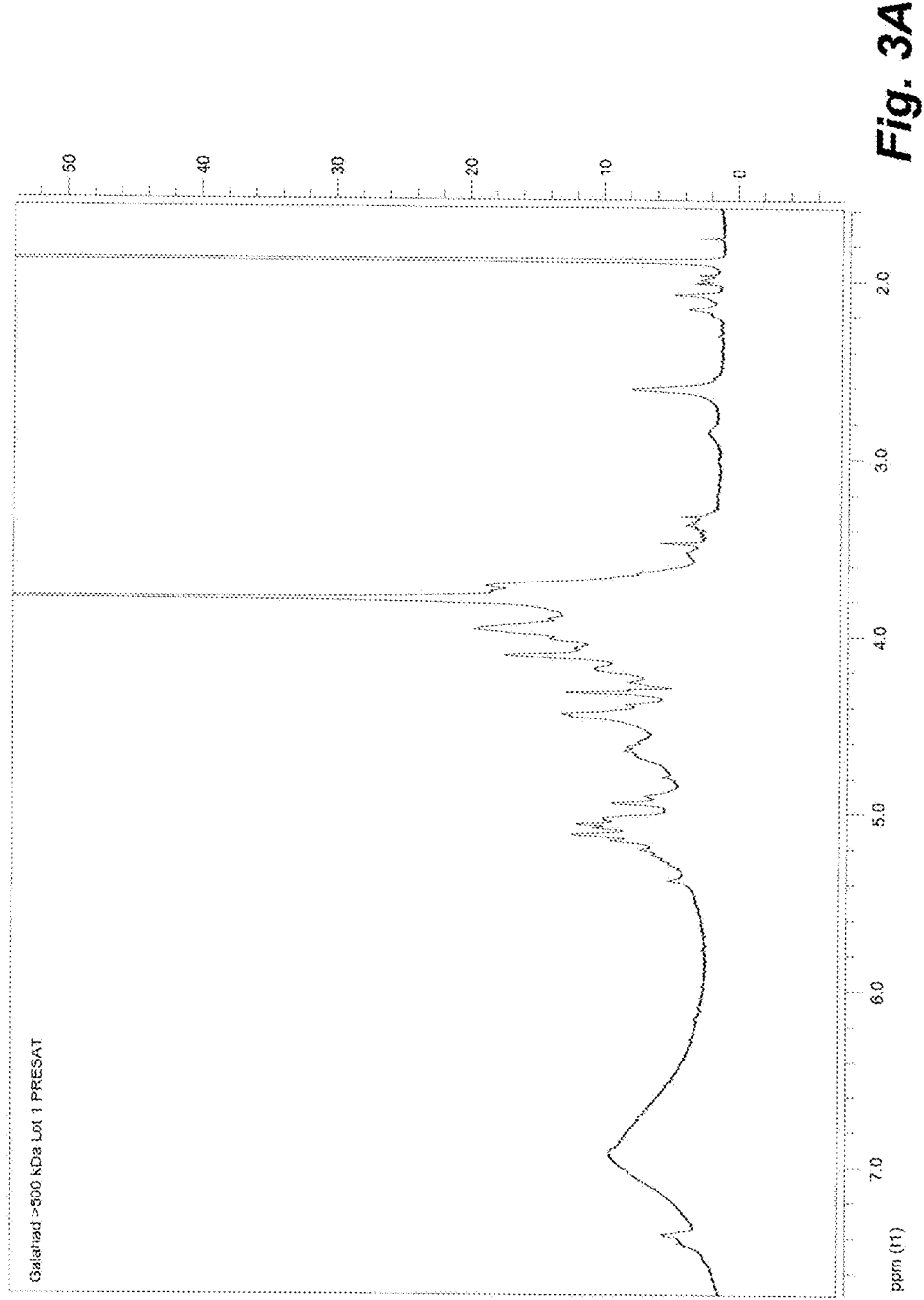
FIG. 3A-E shows NMR of a polysaccharide composition of the invention. 3A shows the 1-D proton spectrum; 3B-3D shows 2-D gradient enhanced COSY, TOCSY and NOESY NMR spectra, respectively; 3E shows the NMR spectrum of the non-carbohydrate portion of the polysaccharide composition.
Figure 3B:
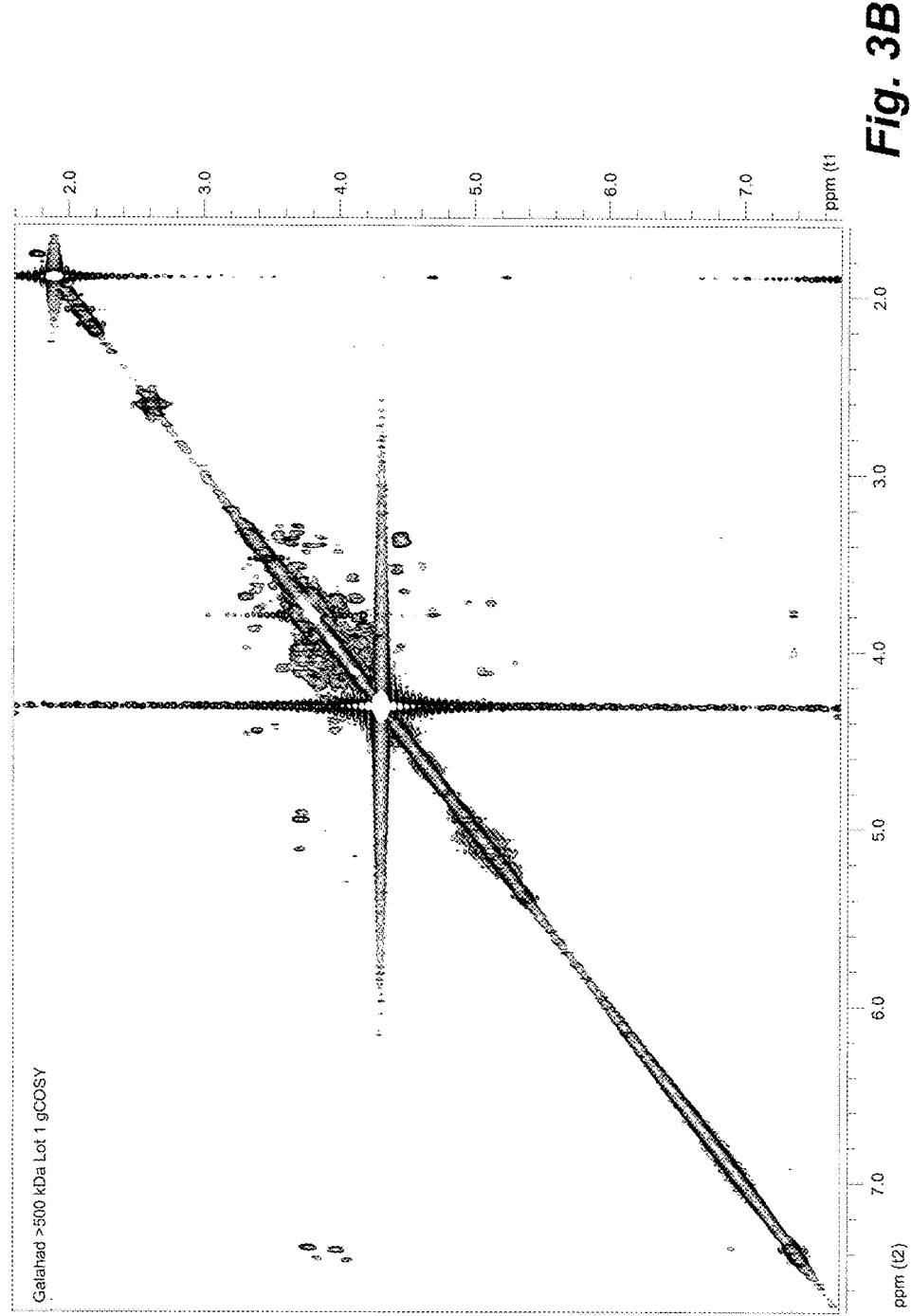
Figure 3C:
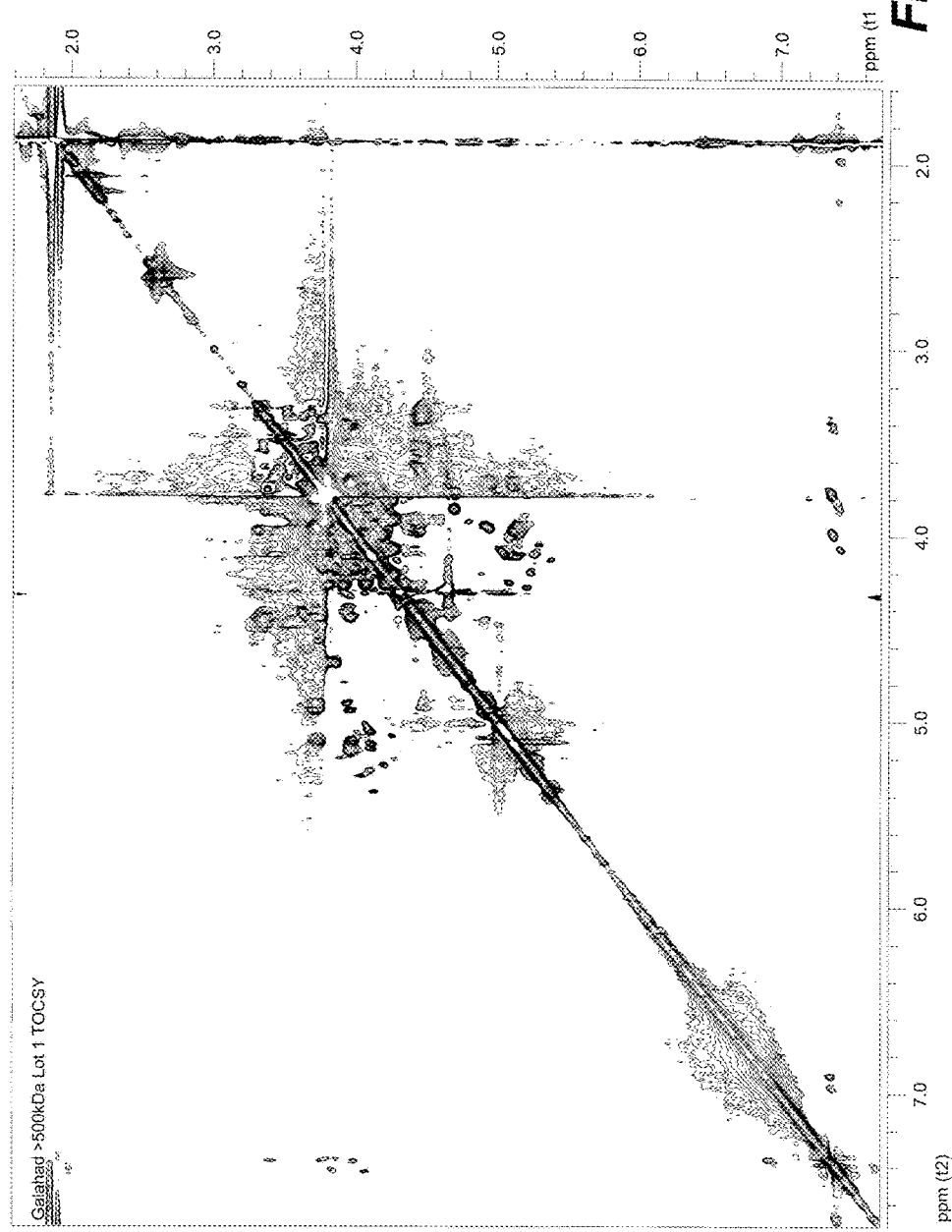
Figure 3D:
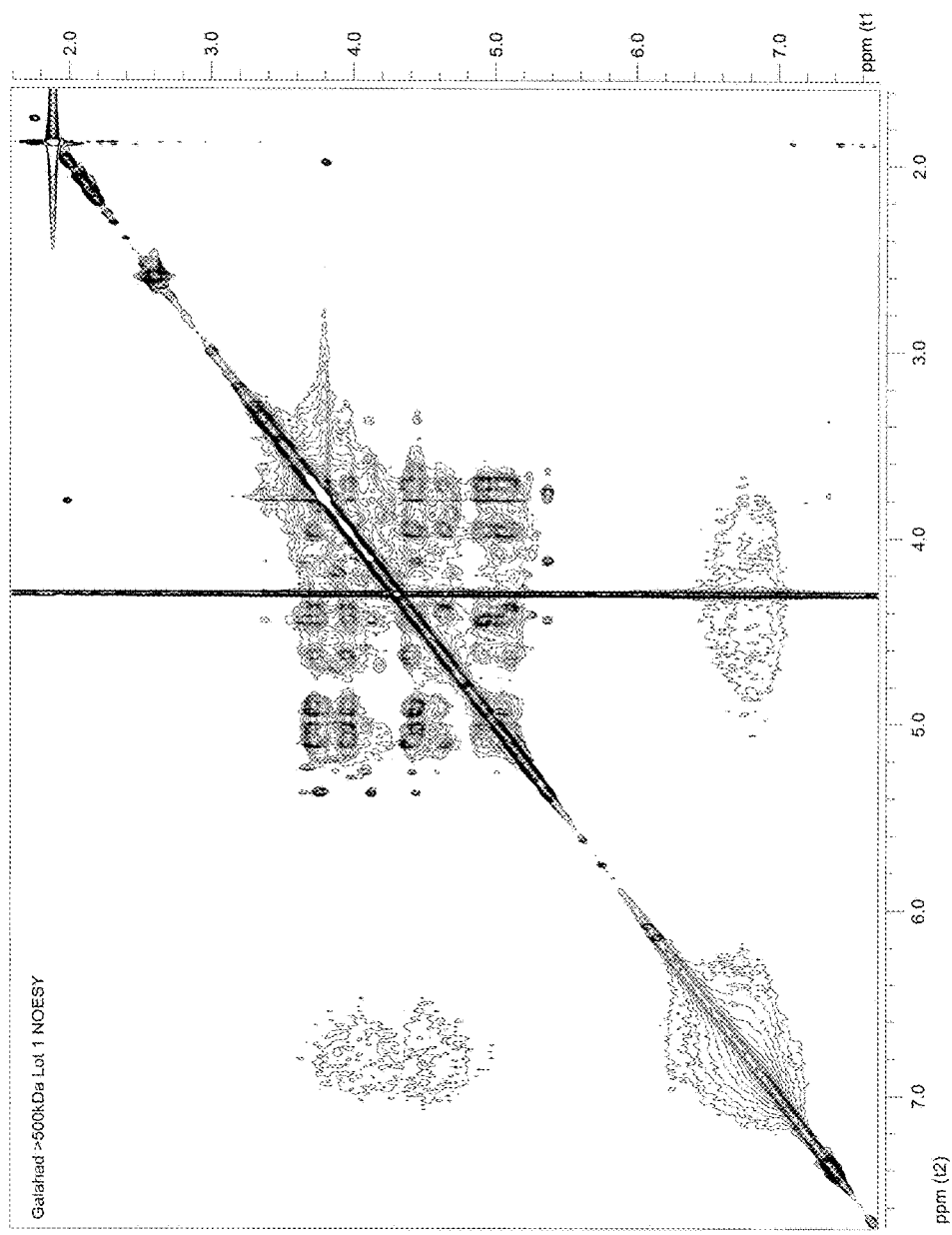
Figure 3E:
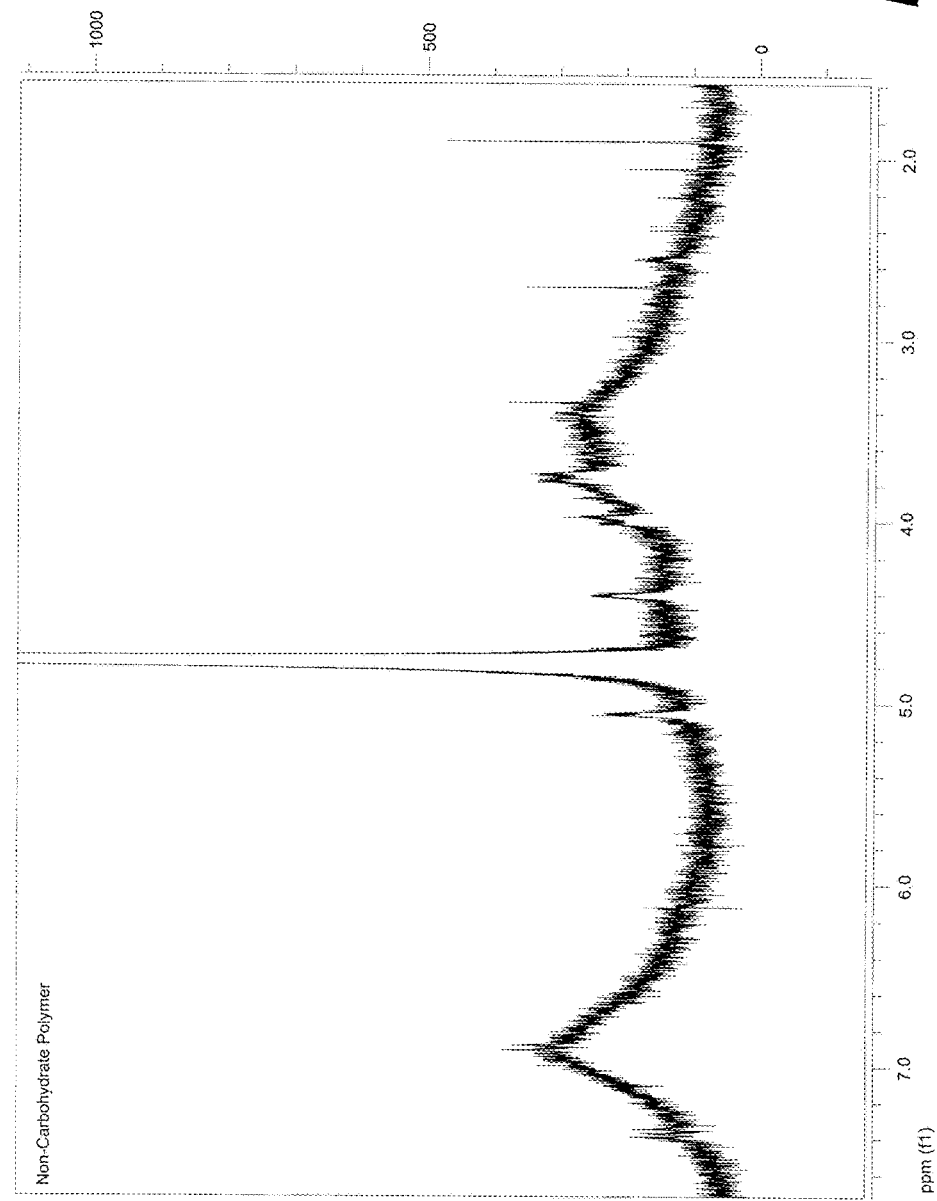

To separate the non-carbohydrate polymer from carbohydrate, we subjected the sample to methanolysis, followed by precipitation and washing, and found by NMR that the non-carbohydrate is stable to the methanolysis conditions. The NMR of this fraction showed that beside the aromatic peak two other broad peaks are present at 3.5 and 4.5 ppm (FIG. 3E).

Example 3

Glycosyl Composition of Polysaccharide Composition

Glycosyl composition analysis was carried out as previously described in Merkle and Poppe (1994) Methods Enzymol. 230: 1-15; York, et al. (1985) Methods Enzymol. 118:3-40. Briefly, an aliquot was taken from a sample of polysaccharide composition prepared as described in Example 1 and added to separate tubes with 20 μg of Inositol as the internal standard. Methyl glycosides were then prepared from the dry sample following the mild acid treatment by methanolysis in 1 M HCl in methanol at 80° C. (8 hours), followed by re-N-acetylation with pyridine and acetic anhydride in methanol (for detection of amino sugars). The sample was then per-O-trimethylsilylated by treatment with Tri-Sil (Pierce) at 80° C. (0.5 hours). GC/MS analysis of the TMS methyl glycosides was performed on an AT 6890N GC interfaced to a 5975B MSD, using a Supelco EC-1 fused silica capillary column (30m×0.25 mm ID). The results are shown in Table A2. Total carbohydrate by weight was found to be 8.2 percent.

TABLE A2

Glycosyl Composition of Polysaccharide Composition

| Glycosyl residue | Mass (: g) | Mole % |
|---|---|---|
| Arabinose (Ara) | 24.1 | 63.0 |
| Rhamnose (Rha) | 1.8 | 4.3 |
| Xylose (Xyl) | 0.9 | 2.3 |
| Galacturonic Acid (GalA) | 4.5 | 9.2 |
| Mannose (Man) | 1.1 | 2.4 |
| Galactose (Gal) | 6.6 | 14.4 |
| Glucose (Glc) | 2.0 | 4.4 |
| Total % carbohydrate by weight | E = 41.0 8.20% | E = 100 |

TABLE A3

Glycosyl Composition of the 150,000 MW Spin-Off Component

| Glycosyl residue | Mass (: g) | Mole % |
|---|---|---|
| Arabinose (Ara) | 20.3 | 65.2 |
| Rhamnose (Rha) | 1.7 | 5.0 |
| Xylose (Xyl) | 0.6 | 2.1 |
| Galacturonic Acid (GalA) | 3.8 | 9.5 |
| Mannose (Man) | 0.9 | 2.3 |
| Galactose (Gal) | 4.2 | 11.3 |
| Glucose (Glc) | 1.7 | 4.6 |
| Total % carbohydrate by weight | E = 33.3 5.55% | E = 100 |

Example 4

Glycosyl Linkage Analysis of Polysaccharide Composition

A solution of polysaccharide composition prepared as described in Example 1 was placed into a membrane dialysis bag (10,000 MW), dialyzed in deionized water for 3 days, followed by lyophilizing. This sample was then methylated by a modification of the method of Hakomori, in which the composition was depolymerized, reduced, and acetylated, and the resultant partially methylated alditol acetates (PMAAs) analyzed by gas chromatography-mass spectrometry (GC-MS) as described by York et al (1985) Methods Enzymol. 118:3-40. Briefly, an aliquot was taken from the sample after lyophilizing and dissolved in DMSO; 0.4 mL potassium dimsylate (2.0 M) was added. After 7 hours at room temperature on stirrer, the reaction mixture was cooled to 0° C., excess methyl iodide (0.7 mL) was added, and the tube sealed. Incubation was then continued for 24 h at room temperature. Following sample work-up, the permethylated material was hydrolyzed using 2 M trifluoroacetic acid (3 h in sealed tube at 100° C.), reduced with $NaBD_4$, and acetylated using acetic anhydride/pyridine. The resulting PMAAs were analyzed on a Hewlett Packard 5890 GC interfaced to a 5970 MSD (mass selective detector, electron impact ionization mode); separation was performed on a 30 m Supelco 2330 bonded phase fused silica capillary column.

TABLE A4

Glycosyl Linkage Analysis of Polysaccharide Composition

| Glycosyl Residue | DK121806 Percentage Present |
|---|---|
| terminally linked arabinofuranosyl residue (t-Araf) | 14.9% |
| 2-linked arabinofuranosyl residue (2-Araf) | 9.6% |
| 2-linked rhamnopyranosyl residue (2-Rhap) | 0.3% |
| 3-linked arabinofuranosyl residue (3-Araf) | 3.2% |
| terminally linked galactopyranosyl residue (t-Gal) | 2.1% |
| 5-linked arabinofuranosyl residue (5-Araf) | 15.8% |
| 3-linked glucopyranosyl residue (3-Glc)&2,4-linked rhamnopyranosyl residue (2,4-Rhap) | 0.7% |
| 2-linked glucopyranosyl residue (2-Glc) | 1.2% |
| 4-linked mannopyranosyl residue (4-Man) | 1.4% |
| 3,5-linked arabinofuranosyl residue (3,5-Araf) | 6.9% |
| 2,5-linked arabinofuranosyl residue (2,5-Araf) | 5.3% |
| 4-linked glucopyranosyl residue (4-Glc) | 4.8% |
| 2,3,5-linked arabinofuranosyl residue (3,5-Araf)& 2,3,4-linked arabinopyranosyl residue (2,3,4-Arap) | 27.0% |
| 4-linked galacturonic acid (4-gal A) | 1.5% |
| 3,6-linked galactopyranosyl residue (3,6-Gal) | 0.4% |
| 2,3,4,6-linked mannopyranosyl residue (2,3,4,6-Man) | 0.7% |
| 2,3,4,6-linked galactopyranosyl residue (2,3,4,6-Gal)&2,3,4-linked galacturonic acid | 2.1% |
| 2,3,4,6-linked glucopyranosyl residue (2,3,4,6-Glc) | 2.2% |

The linkage analysis gives information on the type of glycosidic linkages present in the polysaccharide. The glycosyl composition had shown that the sample is mainly Arabinose with small amount of an unidentified residue and trace amounts of Mannose, Galactose and Rhamnose. This data suggests that the main component in the sample is an arabinan. The linkage data shows that the arabinan consists of backbone of 5-Arabinose and 3,5-Arabinose with side chains of terminal Arabinose and possibly 2-Arabinose backbone.

Example 5

Binding of Polysaccharide Composition to Herpes Simplex Virus-1 (HSV-1) and Inhibition of Infectivity The effect of polysaccharide composition prepared as described in Example 1 on HSV-1 infectivity was tested in Vero cells (African Green Monkey kidney cells). The cells were grown in 12 or 24-well plastic tissue culture plates using standard media and conditions. When infected with HSV-1, these cells form characteristic plaques which, after 3 days, can be observed by light microscopy. For this study, a 2 log (i.e., 100-fold) dilution of polysaccharide composition was mixed with HSV-1 virus at a 2 log dilution in a screw top tube. A second tube contained virus only, and both were stored in the refrigerator for 11 days. An aliquot from each tube was taken on days 1-11 and assayed. No plaques were observed in any well that received the polysaccharide composition-virus mixture, whereas plaques were observed in wells that received virus only up until day 11 of storage. These results indicate that the polysaccharide composition inhibits HSV-1 infectivity for as long as the virus remains viable.

Example 6

Inhibition of Infectivity of a Broad Range of Viruses by Polysaccharide Composition The effect of polysaccharide composition prepared as described in Example 1 on HSV-1 infectivity was tested in Vero cells (African Green Monkey kidney cells). The cells were grown in 12 or 24-well plastic tissue culture plates using media and conditions that were standard for each virus. The results are shown in Tables B1-B4 below and in FIG. 1.

TABLE 1

Effects of undiluted LFT compound on virus infectivity.

| Virus Family | Virus | Strain | Virus Titer with no Treatment | Virus Titer with Treatment | $Log_{10}$ Reduction in Virus Titer |
|---|---|---|---|---|---|
| Non-enveloped viruses | | | | | |
| Adenoviridae | Adenovirus 1 | Chicago | 3.5 | 0[a] | 3.5 |
| Picornaviridae | Polio virus 1 | Chat | 4.5 | 0[a] | 4.5 |
| Picornaviridae | Rhinovirus 2 | HGP | 5.5 | 0[a] | 5.5 |
| Reoviridae | Human rotavirus | Wa | 2.25 | 0[a] | 2.25 |
| Enveloped viruses | | | | | |
| Arenaviridae | Tacaribe | TV | 4.5 | 0[a] | 4.5 |
| Bunyaviridae | Rift Valley Fever (vaccine) | MP-12 | 6.25 | 0[a] | 6.25 |
| Coronaviridae | SARS-CoV | Urbani | 4.25 | 0[a] | 4.25 |
| Herpesviridae | Herpes Simplex 1 | McIntyre | 4.75 | 0[a] | 4.75 |
| Orthomyxoviridae | Influenza A H3N2 | A/California/7/04 | 3.5 | 0[a] | 3.5 |
| Orthomyxoviridae | Influenza A H1N1 | A/New Caledonia/20/99 | 4.25 | 0[a] | 4.25 |
| Orthomyxoviridae | Influenza A H5N1 | Vietnam/1203/4 X Ann Arbor/6/60 (H1N1) | 2.75 | 0[a] | 2.75 |
| Orthomyxoviridae | Influenza A H5N1 | Vietnam/1203/4 X Ann Arbor/6/60 (H1N1)-oseltamivir resistant | 3.75 | 0[a] | 3.75 |
| Orthomyxoviridae | Influenza A H5N1 | DUCK/MN/1525/81 | 3.5 | 0[a] | 3.5 |
| Orthomyxoviridae | Influenza B | B/Shanghai/361/02 | 2.75 | 0[a] | 2.75 |
| Paramyxoviridae | Measles | MO-6 | 5.5 | 0[a] | 5.5 |
| Paramyxoviridae | Human parainfluenza virus 3 | 14709 | 3.75 | 0[a] | 3.75 |
| Paramyxoviridae | Human Respiratory syncytial virus | A1 | 4.75 | 0[a] | 4.75 |

TABLE 1-continued

Effects of undiluted LFT compound on virus infectivity.

| Virus Family | Virus | Strain | Virus Titer with no Treatment | Virus Titer with Treatment | Log₁₀ Reduction in Virus Titer |
|---|---|---|---|---|---|
| Poxviridae | Vaccinia virus | | 4.5 | 0[a] | 4.5 |
| Rhabdoviridae | Vesicular stomatitis virus | Indiana | 4.75 | 0[a] | 4.75 |
| Flaviviridae | Dengue Fever virus | New Guinea | | | |
| Flaviviridae | Yellow Fever virus | 17D | | | |
| Flaviviridae | West Nile virus | New York | | | |

[a]Below detectable limits of assay.

TABLE 2

Effects of LFT compound diluted 1/10 on virus infectivity.

| Virus Family | Virus | Strain | Virus Titer with no Treatment | Virus Titer with Treatment | Log₁₀ Reduction in Virus Titer |
|---|---|---|---|---|---|
| *Non-enveloped viruses* | | | | | |
| Adenoviridae | Adenovirus 1 | Chicago | 3.5 | 0[a] | 3.5 |
| Picornaviridae | Polio virus 1 | Chat | 4.5 | 1.5 | 3.0 |
| Picornaviridae | Rhinovirus 2 | HGP | 5.5 | 4.5 | 1.0 |
| Reoviridae | Human rotavirus | Wa | 2.25 | 1.5 | 0.75 |
| *Enveloped viruses* | | | | | |
| Arenaviridae | Tacaribe | TV | 4.5 | 4.75 | 0.0 |
| Bunyaviridae | Rift Valley Fever (vaccine) | MP-12 | 6.25 | 6.25 | 0.0 |
| Coronaviridae | SARS-CoV | Urbani | 4.25 | 2.25 | 2.0 |
| Herpesviridae | Herpes Simplex 1 | McIntyre | 4.75 | 3.75 | 1.0 |
| Orthomyxoviridae | Influenza A H3N2 | A/California/7/04 | 3.5 | 0[a] | 3.5 |
| Orthomyxoviridae | Influenza A H1N1 | A/New Caledonia/20/99 | 4.25 | 0[a] | 4.25 |
| Orthomyxoviridae | Influenza A H5N1 | Vietnam/1203/4 X Ann Arbor/6/60 (H1N1) | 2.75 | 0[a] | 2.75 |
| Orthomyxoviridae | Influenza A H5N1 | Vietnam/1203/4 X Ann Arbor/6/60 (H1N1)-oseltamivir resistant | 3.75 | 0[a] | 3.75 |
| Orthomyxoviridae | Influenza A H5N1 | DUCK/MN/1525/81 | 3.5 | 0[a] | 3.5 |
| Orthomyxoviridae | Influenza B | B/Shanghai/361/02 | 2.75 | 0[a] | 2.75 |
| Paramyxoviridae | Measles | MO-6 | 5.5 | 3.5 | 2.0 |
| Paramyxoviridae | Human parainfluenza virus 3 | 14709 | 3.75 | 1.25 | 2.5 |
| Paramyxoviridae | Human Respiratory syncytial virus | A1 | 4.75 | 3.75 | 1.0 |
| Poxviridae | Vaccinia virus | | 4.5 | 0[a] | 4.5 |
| Rhabdoviridae | Vesicular stomatitis virus | Indiana | 4.75 | 0[a] | 4.75 |
| Flaviviridae | Dengue Fever virus | New Guinea | | | |
| Flaviviridae | Yellow Fever virus | 17D | | | |
| Flaviviridae | West Nile virus | New York | | | |

[a]Below detectable limits of assay.

TABLE 3

Effects of LFT compound diluted 1/100 on virus infectivity.

| Virus Family | Virus | Strain | Virus Titer with no Treatment | Virus Titer with Treatment | Log₁₀ Reduction in Virus Titer |
|---|---|---|---|---|---|
| *Non-enveloped viruses* | | | | | |
| Adenoviridae | Adenovirus 1 | Chicago | 3.5 | 0[a] | 3.5 |
| Picornaviridae | Polio virus 1 | Chat | 4.5 | 1.5 | 3.0 |
| Picornaviridae | Rhinovirus 2 | HGP | 5.5 | 5.75 | 0.0 |
| Reoviridae | Human rotavirus | Wa | 2.25 | 1.5 | 0.75 |
| *Enveloped viruses* | | | | | |
| Arenaviridae | Tacaribe | TV | 4.5 | 5.25 | 0.0 |
| Bunyaviridae | Rift Valley Fever (vaccine) | MP-12 | 6.25 | 7.25 | 0.0 |
| Coronaviridae | SARS-CoV | Urbani | 4.25 | 3.5 | 0.75 |
| Herpesviridae | Herpes Simplex 1 | McIntyre | 4.75 | 4.5 | 0.25 |
| Orthomyxoviridae | Influenza A H3N2 | A/California/7/04 | 3.5 | 1.5 | 2.0 |

TABLE 3-continued

Effects of LFT compound diluted 1/100 on virus infectivity.

| Virus Family | Virus | Strain | Virus Titer with no Treatment | Virus Titer with Treatment | Log$_{10}$ Reduction in Virus Titer |
|---|---|---|---|---|---|
| Orthomyxoviridae | Influenza A H1N1 | A/New Caledonia/20/99 | 4.25 | 1.25 | 3.0 |
| Orthomyxoviridae | Influenza A H5N1 | Vietnam/1203/4 X Ann Arbor/6/60 (H1N1) | 2.75 | 0.75 | 2.0 |
| Orthomyxoviridae | Influenza A H5N1 | Vietnam/1203/4 X Ann Arbor/6/60 (H1N1)-oseltamivir resistant | 3.75 | 3.25 | 0.5 |
| Orthomyxoviridae | Influenza A H5N1 | DUCK/MN/1525/81 | 3.5 | 1.75 | 1.75 |
| Orthomyxoviridae | Influenza B | B/Shanghai/361/02 | 2.75 | 0$^a$ | 2.75 |
| Paramyxoviridae | Measles | MO-6 | 5.5 | 5.75 | 0.0 |
| Paramyxoviridae | Human parainfluenza virus 3 | 14709 | 3.75 | 2.75 | 1.0 |
| Paramyxoviridae | Human Respiratory syncytial virus | A1 | 4.75 | 4.25 | 0.5 |
| Poxviridae | Vaccinia virus | | 4.5 | 2.25 | 2.25 |
| Rhabdoviridae | Vesicular stomatitis virus | Indiana | 4.75 | 1.25 | 3.5 |
| Flaviviridae | Dengue Fever virus | New Guinea | | | |
| Flaviviridae | Yellow Fever virus | 17D | | | |
| Flaviviridae | West Nile virus | New York | | | |

$^a$Below detectable limits of assay.

TABLE 4

Effects of undiluted LFT compound on virus infectivity when virus is diluted by a factor of 10.

| Virus Family | Virus | Strain | Virus Titer with no Treatment | Virus Titer with Treatment | Log$_{10}$ Reduction in Virus Titer |
|---|---|---|---|---|---|
| | | Non-enveloped viruses | | | |
| Adenoviridae | Adenovirus 1 | Chicago | 2.5 | 0$^a$ | 2.5 |
| Picornaviridae | Polio virus 1 | Chat | No infectivity | | |
| Picornaviridae | Rhinovirus 2 | HGP | 3.75 | 0$^a$ | 3.75 |
| Reoviridae | Human rotavirus | Wa | 1.25 | 0$^a$ | 1.25 |
| | | Enveloped viruses | | | |
| Arenaviridae | Tacaribe | TV | 3.5 | 0$^a$ | 3.5 |
| Bunyaviridae | Rift Valley Fever (vaccine) | MP-12 | 5.25 | 0$^a$ | 5.25 |
| Coronaviridae | SARS-CoV | Urbani | 3.25 | 0$^a$ | 3.25 |
| Herpesviridae | Herpes Simplex 1 | McIntyre | 3.5 | 0$^a$ | 3.5 |
| Orthomyxoviridae | Influenza A H3N2 | A/California/7/04 | 2.5 | 0$^a$ | 2.5 |
| Orthomyxoviridae | Influenza A H1N1 | A/New Caledonia/20/99 | 3.25 | 0$^a$ | 3.25 |
| Orthomyxoviridae | Influenza A H5N1 | Vietnam/1203/4 X Ann Arbor/6/60 (H1N1) | 1.75 | 0$^a$ | 1.75 |
| Orthomyxoviridae | Influenza A H5N1 | Vietnam/1203/4 X Ann Arbor/6/60 (H1N1)-oseltamivir resistant | 1.75 | 0$^a$ | 1.75 |
| Orthomyxoviridae | Influenza A H5N1 | DUCK/MN/1525/81 | 2.5 | 0$^a$ | 2.5 |
| Orthomyxoviridae | Influenza B | B/Shanghai/361/02 | 1.75 | 0$^a$ | 1.75 |
| Paramyxoviridae | Measles | MO-6 | 4.25 | 0$^a$ | 4.25 |
| Paramyxoviridae | Human parainfluenza virus 3 | 14709 | 2.75 | 0$^a$ | 2.75 |
| Paramyxoviridae | Human Respiratory syncytial virus | A1 | 3.75 | 0$^a$ | 3.75 |
| Poxviridae | Vaccinia virus | | 3.5 | 0$^a$ | 3.5 |
| Rhabdoviridae | Vesicular stomatitis virus | Indiana | 3.75 | 0$^a$ | 3.75 |
| Flaviviridae | Dengue Fever virus | New Guinea | | | |
| Flaviviridae | Yellow Fever virus | 17D | | | |
| Flaviviridae | West Nile virus | New York | | | |

$^a$Below detectable limits of assay.

The polysaccharide composition appears not to act via binding to a receptor on cells because when the polysaccharide composition is added to cells, followed by washing and subsequent exposure to virus, there was no observed inhibition of infectivity. In addition, exposure of the polysaccharide composition to cells for 10 minutes did not reduce its ability to inhibit viral infectivity. These findings indicate that the effect of the polysaccharide composition on viral infectivity is due to its binding virus, as opposed to binding cells or some other component or uptake by cells.

The antiviral activity of polysaccharide composition was assessed in a cytopathic effect and plaque reduction assay reduction (CPE) assay, and the composition was found to have specific antiviral activity against both HSV-1 and HSV-2. To confirm these data, a standard plaque reduction assay was used to measure antiviral activity and no activity was observed. These results suggested that the extract might need to be present during the attachment phase of viral replication. When the study was repeated and the cells were pretreated with the polysaccharide composition, antiviral activity was observed although it was less effective than the activity observed in the CPE assay. This confirmed that the polysaccharide composition was acting during the attachment phase of viral replication. It was also possible that the extract might be directly inactivating virus particles prior to attachment, so a standard inactivation study was used to evaluate this potential activity. This study also confirmed that the polysaccharide composition can directly inactivate virus particles. These data taken together suggest that the polysaccharide composition acts prior to infection and can inactivate virions as well as block infection during attachment.

Example 7

In Vivo Protection Against Viral Challenge by Polysaccharide Composition-Based Vaccine In this study, the polysaccharide composition of the invention, prepared as described in Example 1 (referred to herein as "LFT compound") was tested for ability to confer in vivo protection against viral challenge.

Introduction

Example 6 shows that LFT compound can inactivate a wide range of enveloped and non-enveloped viruses, including avian influenza A viruses. It has been hypothesized that the interaction of LFT compound with each virion, which leads to the inactivation of infectious virions could be useful in developing an inactivated vaccine, especially if the interaction between the LFT compound and the virion did not alter the key immune recognition sites on the virion necessary for eliciting of a protective response to infectious virus. The purpose of the current research reported below was to test the hypothesis that avian influenza A H5N1 virus inactivated by LFT compound could be used to protect mice against lethal infection by influenza A/Duck/MN/1525/81 (H5N1) virus.

Materials and Methods

Virus and Cells

Madin Darby canine kidney cells (MDCK) were obtained from the American Type Culture Collection (ATCC, Manassas, Va., USA). Growth medium was minimal essential medium (MEM) with 5% fetal bovine serum (Hyclone Laboratories. Logan, Utah, USA) supplemented with 0.1% $NaHCO_3$. Growth medium had no supplemental antibiotics. When evaluating virus replication in the cells, the medium was MEM without serum, 0.18% NaHCO3, 20 μg trypsin/ml, 2.0 μg EDTA/ml, and 50 μg gentamicin/ml. Influenza A/Duck/MN/1525/81 (H5N1) was obtained initially from Dr. Robert Webster of St. Jude Hospital, Memphis, Tenn. It was either passaged in MDCK cells in vitro, or it was passaged through mice until adapted to the point of being capable of inducing pneumonia-associated death in the animals. Pools of the virus were subsequently prepared for animal studies or cell culture studies and were maintained at −80° C.

Inactivated Virus for Vaccine Study

Influenza A H5N1 virus (MN/1281/81) at $10^{5.5}$ $TCID_{50}$, $10^{4.5}$ $TCID_{50}$, or $10^{3.5}$ $TCID_{50}$ was treated with LFT lot #2 for 24 h at 37° C. After the treatment, the preparations were aliquoted and stored at −80° C. until used to immunize animals.

Reagents

LFT (lot #2) was used for this study. Alum was obtained from Pierce Biotechnology, Inc. (Rockford, Ill., USA).

Animals

Female specific pathogen-free 18-21 g BALB/c mice were obtained from Charles River Laboratories (Wilmington, Mass.). They were quarantined 5 days prior to use. They were housed in polycarbonate cages with stainless steel tops and provided tap water and standard rodent mouse chow ad libitum.

Vaccine Challenge Study

Groups of 10 mice were immunized with one of three concentrations ($10^{5.5}$ $TCID_{50}$, $10^{4.5}$ $TCID_{50}$, or $10^{3.5}$ $TCID_{50}$) of LFT-treated virus intramuscularly (i.m.) or intradermally (i.d.) or with PBS i.m. or i.d. in the presence or absence of alum. Immunizations were given on days 0, 14, and 28. On days −7, 21 and 42 and 56 relative to exposure to inactivated virus vaccine, serum was collected by submandibular bleed from all living mice for measurement of neutralizing antibody. On day 42, mice were challenged intranasally with $10^{3.5}$ $TCID_{50}$ of influenza A H5N1 virus (MN/1281/81). On day 46, 3 mice from each group were sacrificed to harvest lungs for assessment of virus lung titers; the remaining, surviving mice were sacrificed on day 56 to harvest lungs for virus titration and blood for virus neutralization tests.

Neutralizing Antibody Assay

An equal volume of a serum sample at an appropriate dilution (usually 1:50 or 1:100) and virus at 200 $TCID_{50}$ were mixed and incubated at 37° C. for 1 hour under gentle rocking conditions. At the end of this time, the neutralization mixture was serially diluted and the surviving virus titered by CPE (cytopathic effect) assay. Eight dilutions were plated in quadruplicate and the assay was done three times on the same plate for each serum. For the CPE assay, 0.1 ml of a neutralization sample was added directly to the cell culture plate containing cells at the appropriate cell density ($1\times10^4$ Vero 76 cells/well) plated the previous day in 96-well plate. An additional 0.1 ml of medium, containing 20 μg trypsin/ml, 2.0 μg EDTA/ml, and 50 μg gentamicin/ml (all final concentrations) was then added to each well, gently mixed and incubated at 37° C. for 6 days, the optimal time required to achieve full cytopathic effect in the non-treated infectivity controls when using the virus at 200 $TCID_{50}$ units. The wells in the plate were then scored by visual lobservation for cytopathic effect or cytotoxicity using light microscopy. CPE was graded upon a scale of 0-4; 0=no cytopathic effect and 4=100% cytopathic effect. Titers were then calculated using the Reed-Muench method. The inverse of the most dilute serum sample completely protecting cells from virus cytopathic effects was considered the virus neutralization titer for the serum. Infectivity controls virus titrations ("virus back titration"), which were an equal volume of virus added to an equal volume of MEM and treated in the same manner as the sera were titered last as a control for virus deterioration during the assays of the sera.

Lung Scoring

Lungs were scored based on surface appearance of lungs. Lungs were assigned a score from 0-4, with 0 meaning that the lungs looked normal and 4 denoting that the entire surface area of the lung was inflamed and showed plum colored lung consolidation.

Lung Virus Titer Determination

Each mouse lung was homogenized, the tissue fragments allowed to settle, and varying dilutions of the supernatant fluids were assayed in triplicate for infectious virus in Vero 76 cells by CPE assay and titers ($TCID_{50}$ values) calculated using the Reed-Muench method.

Histopathology

Thin sections of lungs were stained with hematoxylin and a board-certified veterinarian for pathology examined eosin and the slides.

Statistical Analysis

Differences in mean lung virus titers were evaluated by the analysis of variance. Differences in death rates were determined by Chi-square analysis.

Results

The results are shown in Table C1 below.

used with six of seven animals surviving. However, virus lung titers were not reduced compared to unimmunized animals and the lungs of animals receiving the largest dose of vaccine were again characterized by severe inflammation. However, the lungs of animals receiving ten-fold less inactivated virus particles were characterized by much less severe pathogenesis. Modest amounts of neutralizing antibody (titer=667) were generated at the two highest doses of vaccine used. Some neutralizing antibody was also generated by exposure to the infectious virus itself.

TABLE 1

Effects of Immunizing Mice with LFT-Inactivated Influenza A/Duck/MN/1525/81 (H5N1)

| GROUP | Vaccine (Amount of inactivated virus) | Neutralizing Antibody Titer* (Inverse of Dilution ± SD) Day of Bleed Relative to Vaccine Administration 0 | 21 | 46 | 56 | LUNG VIRUS TITER, $log_{10}$ CCID50 ± SD 46 | 56 | Live/Total Day 56 | Typical Histopathogical Description for Group |
|---|---|---|---|---|---|---|---|---|---|
| Vaccine without Adjuvant Intramuscular administration (i.m.) | | | | | | | | | (3 animals, day 46) |
| 1 | ($10^{5.5}CCID_{50}$) | <50† | <50 | <50 | 700 ± 589 | 5.96 ± 0.07 | 0.53 ± 0.06 | 4/7¶ | Severe inflammation |
| 2 | ($10^{4.5}CCID_{50}$) | <50 | <50 | <50 | 433 ± 197 | 6.00 ± 0.13 | 0.54 ± 0.07 | 3/7 | Moderate bronchopneumonia |
| 3 | ($10^{3.5}CCID_{50}$) | <50 | <50 | <50 | 400 ± 0 | 5.83 ± 0.19 | <0.50 ± 0.00 | 1/7 | Mild-Mod bronchopneumonia |
| 4 | PBS | <50 | <50 | <50 | No survivors | 5.75 ± 0.43 | No survivors | 0/7 | Mild-Mod bronchopneumonia |
| Intradermal administration (i.d.) | | | | | | | | | |
| 5 | ($10^{5.5}CCID_{50}$) | <50 | <50 | <50 | 667 ± 197 | 5.67 ± 0.29 | <0.50 ± 0.00 | 6/7‡ | Severe inflammation |
| 6 | ($10^{4.5}CCID_{50}$) | <50 | <50 | <50 | 667 ± 197 | 5.79 ± 0.64 | <0.50 ± 0.00 | 6/7‡ | Mild bronchopneumonia |
| 7 | ($10^{3.5}CCID_{50}$) | <50 | <50 | <50 | 450 ± 252 | 6.04 ± 0.52 | <0.50 ± 0.00 | 2/7 | Mild-Mod bronchopneumonia |
| 8 | PBS | <50 | <50 | <50 | 400 ± 0 | 5.79 ± 0.19 | <0.50 ± 0.00 | 3/7 | Mild bronchopneumonia |
| Vaccine + Alum adjuvant Intramuscular administration | | | | | | | | | |
| 9 | ($10^{5.5}CCID_{50}$) | <50 | <50 | 75 ± 43 | 1235 ± 1570 | 4.71 ± 0.69‡ | <0.50 | 6/6‡ | Moderate bronchopneumonia |
| 10 | ($10^{4.5}CCID_{50}$) | <50 | <50 | 108 ± 101 | 1494 ± 1885 | 5.63 ± 0.00 | <0.50 ± 0.00 | 4/7¶ | Mid-Mod bronchopneumonia |
| 11 | ($10^{3.5}CCID_{50}$) | <50 | <50 | <50 | All dead | 6.17 ± 0.59 | <0.50 ± 0.00 | 0/7 | Mild-Mod bronchopneumonia |
| 12 | PBS + Alum (i.m.) | <50 | <50 | <50 | 267 ± 230 | 6.21 ± 0.29 | <0.50 | 1/7 | Moderate bronchopneumonia |
| Intradermal administration | | | | | | | | | |
| 13 | ($10^{5.5}CCID_{50}$) | <50 | <50 | 450 ± 260 | 242 ± 186 | 1.88 ± 1.85¶ | <0.50 ± 0.00 | 7/7‡ | Moderate bronchopneumonia |
| 14 | ($10^{4.5}CCID_{50}$) | <50 | <50 | <50 | 535 ± 2 | 5.63 ± 0.33 | <0.50 ± 0.00 | 3/7 | Mild-Mod bronchopneumonia |
| 15 | ($10^{3.5}CCID_{50}$) | <50 | <50 | <50 | 533 ± 462 | 6.13 ± 0.38 | <0.50 ± 0.00 | 1/7 | Mild inflammation |
| 16 | PBS + Alum | <50 | <50 | <50 | 334 ± 94 | 5.54 ± 0.38 | <0.50 ± 0.00 | 2/7 | Mild-Mod bronchopneumonia |
| Toxicity Controls-No Virus challenge | | | | | | | | | |
| 17 | PBS + Alum (i.m.) | <50 | <50 | <50 | <50 | <0.50 | <0.50 ± 0.00 | 2/2 | No lesions |
| 18 | Vaccine + Alum (i.d.) | <50 | <50 | 400 ± 0 | 267 ± 189 | <0.50 | <0.50 ± 0.00 | 2/2 | No lesions |
| 19 | Vaccine + Alum (i.m.) | <50 | <50 | <50 | <50 | <0.50 | <0.50 ± 0.00 | 2/2 | No lesions |

*Neutralizing titer = largest antibody dilution that prevented virus cytopathic effect.

†Denotes that virus neutralization titer was below the limit of detection of assay.

‡Significantly different from placebo control, $P < 0.01$.

¶Significantly different from placebo control, $P < 0.001$.

The alum and the vaccine appeared to be well-tolerated when evaluated in mice without wild type virus challenge; they did not induce detectable pathogenesis in the lungs (See groups 17-19, Table C1).

Without Adjuvant

Intramuscular

Intramuscular administration of the whole unit inactivated virus vaccine without adjuvant was effective in protection against challenge from wild type virus. Four of seven animals survived, although the virus lung titers in these animals were not reduced relative to the placebo control (Table C1). This may have been the reason that the lungs of surviving animals seemed to be characterized by severe inflammation. Modest amounts of neutralizing antibody (titer=700) were generated at the highest dose of vaccine used. Administration by intradermal route using the vaccine without adjuvant was also protective at two highest dosages With Adjuvant Administration of vaccine in the presence of alum adjuvant appeared to be the most effective in terms of not only in protecting against death to due to virus challenge, but also in ameliorating lung pathogenesis and lowering virus lung titers.

Intramuscular and Intradermal

Animals treated with highest dose of vaccine, administered either i.m. or i.d., were all protected against death (i.m., 6/6; i.d., 7/7), the virus titers were significantly reduced (i.m., P<0.01; i.d., P<0.001) and the lung pathogenesis was not as severe as in animals immunized with vaccine only and protected against death. In addition, the i.d. immunization appeared to be the most effective of all immunizations in reducing virus lung titers (3.66 $log_{10}$ reduction).

Discussion

The data indicate that any animal that survives the lethal infection with challenge virus will produce neutralizing antibody (Table C1). In the presence of high doses of the inactivated vaccine, production of neutralizing antibody seemed to increase as did survival to lethal challenge of virus, a phenomenon which has been shown with other vaccines against influenza, for example with a vaccine against the 1918 strain of influenza A. The sole exception to this generalization was the vaccine regimen in which high dose inactivated vaccine in adjuvant, administered i.d was extremely protective, but did not result in much neutralizing antibody being produced. However, virus lung titers in animals treated with this vaccine were greatly reduced by almost a factor of 10,000. It may be that this particular vaccine regimen also stimulated other protective, immune responses such as interferon and natural killer cell activity very early in the challenge infection that resulted in the substantial elimination of infectious virus particles to be presented to antigen presenting cells. This early elimination of virus infectious virus may have significantly reduced the amount of virus available for antigen presentation and thus reduced the number of B cells programmed to produce neutralizing antibody. Intradermal administration of the whole unit inactivated virus vaccine with or without adjuvant seemed to be somewhat more protective against death than i.m. administration. This could be due to the fact underneath the skin are dendritic cells (Langerhans cells), one of the major antigen presenting cells of the body, while muscle is not considered to be a site for antigen presentation because it contains few if any dendritic cells. It may be that in this experiment, better antigen presentation occurred due to direct interaction of dendritic cells underneath the skin with the antigen present in the vaccine. This in turn could have led to an increased, proper presentation of the appropriate antigen to the immune system resulting in a more efficient and quicker response to infection upon challenge with live virus.

Administration of vaccine in the presence of alum adjuvant appeared to be the most effective regimen in terms of not only protecting against death due to virus challenge, but also in ameliorating lung pathogenesis and lowering virus lung titers. Adjuvants such as alum cause what amounts to be a time-release of antigen to the immune system, leading to enhanced uptake by phagocytic antigen presenting cells such as macrophages and dendritic cells. The results of such a release and enhancement could have also led to the enhanced immune response seen in the current study.

Conclusions

The intramuscular administration of vaccine in alum adjuvant was overall the most effective vaccine regimen used. It protected 100% of the mice from death due to virus challenge, limited lung pathogenesis, significantly reduced the virus lung titers in treated animals and stimulated the production of the greatest amount of neutralizing antibody. Intradermal immunization in the presence of adjuvant might be considered even more efficacious, if neutralizing antibody were generated in greater amounts. These results suggest that LFT-inactivated virus represents a new method of creating inactivated vaccines that should be pursued.

Example 8

Evaluating Adjuvant-Free Polysaccharide Composition Inactivated Influenza A/Duck/MN/1525/81 (H5N1) Virus Vaccines in a Lethal BALB/c H5N1 Influenza A Model Purpose of the Study The purpose of the study was to test the hypothesis that avian influenza A H5N1 virus that had been inactivated by a polysaccharide composition of the invention (prepared as described in Example 1), administered intradermally or intranasally, could be used to protect mice against lethal infection by influenza A/Duck/MN/1525/81 (H5N1) virus without using an adjuvant. This study employed the same general methods and types of animals as Example 7.

Summary

The polysaccharide composition-inactivated (10 min) influenza A/Duck/MN/1525/81 (H5N1) vaccine was completely protective against homologous virus challenge at certain doses without the use of adjuvant. Intranasally administered vaccine, given twice 14 days apart, was the most efficacious immunization regimen. The data suggest that polysaccharide composition represents an innovative and effective way of deriving vaccines.

Vaccine Regimen

"Vaccine 1a"=With 10 min. inactivated virus at $10^{5.7}$ $CCID_{50}$ administered twice intranasally.

"Vaccine 1b"=With 10 min. inactivated virus at $10^{4.7}$ $CCID_{50}$ administered twice intranasally.

"Vaccine 1c"=With 10 min. inactivated virus at $10^{3.7}$ $CCID_{50}$ administered twice intranasally.

Each of the above vaccines was prepared as described in Example 7, except that the polysaccharide composition was exposed to virus for 10 minutes, rather than 24 hours.

Survival

Two courses of Vaccine 1a and 1b (polysaccharide composition-inactivated for 10 min) delivered intranasally significantly protected mice completely, although Vaccine 1a prevented death in all immunized mice.

Neutralizing Antibody

In mice receiving Vaccines 1a, 1b, and 1c twice intranasally, there were substantial amounts of neutralizing antibodies two days prior to virus challenge and none in mice receiving no vaccine as had been expected. Three days after challenge with virus, the neutralizing antibody began to rise in the mice receiving Vaccines 1a and 1b, and, in general, these titers continued to rise to the end of the trial.

Virus Lung Titers

Interestingly, mice immunized twice intranasally with Vaccine 1a had no detectable virus lung titers, which corresponded with a 100% survival rate in this group and the highest virus neutralization titers.

Effects of Various Lung Parameters

It was assumed that if the vaccine prevented or lessened viral colonization of lung tissue, it should result in reduced lung scores, lung pathology, lung weights, and better lung function as manifested in higher saturated blood oxygen levels.

Lung Scores

Lung scores for mice immunized twice with Vaccine 1a intranasally were significantly lower on days 6 and 14 than those lung scores recorded for unimmunized mice on the same days after virus challenge ($P<0.05$-$0.01$). This corresponded with significant protection against death.

Lung Pathology

The lung pathology of mice immunized twice intranasally was not remarkably different than the lung pathology observed for the unimmunized cohort mice at day 3. In general, for all groups, the pathology was characterized by a few bronchioles segmentally lined by necrotic epithelial cells containing luminal neutrophils. A few large airways were surrounded by small aggregates of lymphocytes, some forming follicles.

Arterial Saturated Oxygen ($SaO_2$) Levels

In the current study, all of the unimmunized mice for each vaccine trial arm had much lower $SaO_2$ level trends than did the immunized cohorts, regardless of vaccine used or the route of delivery. When Vaccine 1a was given twice intradermally or intranasally, $SaO_2$ levels in these mice remained significantly higher when compared to the $SaO_2$ levels in the respective cohorts for each trial arm. This correlated well with survival rates, especially for mice receiving Vaccine 1a intranasally.

Weight Changes

One parameter that is often associated with severe disease and sometimes with death in the influenza mouse model used in the current vaccine study is weight loss. Mice receiving Vaccine 1 once or twice intranasally, which were some of the more effective vaccine regimens protecting mice against lethal virus challenge, also had the least amount of weight change throughout the duration of the experiment. They also had less weight loss.

Cytokine Levels

For mice receiving Vaccine 1 twice intranasally at day 6, only the levels of the chemokine MCP-1 and the cytokine TNF-alpha seemed to be dramatically reduced compared to levels of that chemokine and cytokine in unimmunized mice.

All levels for all cytokines and chemokines were nearly the same in immunized and in the unimmunized animals with the exception of IL-12 levels in unimmunized mice, which were much higher. The apparent reduction of IL-12 levels in immunized mice correlated with the significant increase in immunized mice surviving virus infection.

The cytokine "storm" one often expects with an H5N1 infection with mice was not detected in this vaccine study with the exception of in the unimmunized mice, which had drastically higher IL-12 levels. Immunization apparently reversed IL-12 levels in mice receiving the vaccine.

Discussion

The polysaccharide composition vaccines were well tolerated throughout the immunization period, regardless of the number of doses given, indicating a lack of overt toxicity.

For efficacy of protection, the best vaccine and regimen evaluated was using the vaccine containing $10^{5.7}$ virus inactivated by polysaccharide composition for 10 min, delivered intranasally twice with the second dose coming 14 days after the primary vaccine dose. The virus neutralization titers of mice immunized with the twice-delivered intranasal vaccine were highest 14 days after virus challenge.

The vaccine eliminated the colonization of the lung by challenge virus. This translated into less gross pathology and milder pathology detected in sectioned lungs.

The levels of proinflammatory cytokines detected in the lungs of these animals were also substantially lower than in other immunized group of mice, reinforcing the conclusion that the vaccine containing $10^{5.7}$ virus inactivated by polysaccharide composition for 10 min, delivered intranasally twice prevented severe lung pathology due to virus infection. These effects probably are indicative of near normal lung function as well. This conclusion is supported by the fact the arterial saturated oxygen levels in this immunized group of mice were substantially higher than those detected in the unimmunized mice and most other immunized groups of mice.

Inactivation of the virus with polysaccharide composition for only 10 minutes was sufficient to reduce the levels on infectious virus to the undetectable limits of the assay used to quantitate infectious virus (data not shown), yet was sufficient to elicit high titers of neutralizing antibody.

Conclusions

The results suggest that an effective vaccine can be made from polysaccharide composition-inactivated virus after only a 10 minute exposure, that it can be delivered without adjuvant, unlike previously conjectured, and that intranasal delivery provides the most protective response against death, pathology, localized detrimental cytokine increases, and virus colonization by challenge virus.

The efficacy seen with the current polysaccharide composition-inactivated vaccine given intranasally and without adjuvant was achieved with two exposures and no adjuvant. In addition to reduced lung pathogenesis or no lung pathogenesis and little or no virus colonization of the lung by challenge virus, neutralizing antibody titers were high. This suggests that polysaccharide composition inactivated vaccines without adjuvant are efficacious without the problems associated with adjuvant formulation.

Thus, polysaccharide composition-inactivated virus represents a new method of creating inactivated vaccines that should be pursued for possible use in developing a new human influenza A vaccine. The technology is be amenable for creating inactivated vaccines for other viral diseases.

Example 9

The Polysaccharide Composition Inhibits Growth of Cancer Cells

The treatment of cancer cell lines with polysaccharide composition prepared as described in Example 1 inhibits replication of various cancer cells. In this study, Vero cells, A549 (human lung carcinoma), HeLa229 (human cervix adenocarcinoma), NCI-H292 (pulmonary muco-epidermoid carcinoma), and (CACO-2: human colon carcinoma) were exposed to various concentrations of the polysaccharide composition to generate dose-response curves indicating that the polysaccharide composition can inhibit and even prevent replication and that this effect correlated with dose. The effect was reversible if the cells were washed within 3 hours of initial exposure. After 3 hours of exposure, the cells would not replicate and went on to die. If the polysaccharide composition was washed off within 3 hours, cell division restarted in 4-6 hours.

Example 10

Treatment of Squamous Cell Carcinoma with a Polysaccharide Composition

Topical Administration

A human subject having a squamous cell carcinoma on the chin was treated with a polysaccharide composition prepared as described in Example 1. FIG. 4A shows the lesion as it appeared before treatment. The treatment regimen consisted of topical application of the polysaccharide composition every 15 minutes for a period of 4 hours; this treatment was carried out once daily. The appearance of the lesion on treatment day 5 is shown in FIG. 4B. Whereas the lesion included a large, raised mound prior to treatment, at day 5, the lesion included a much smaller raised area, and the edges of the lesion are beginning to heal inward. In addition, comparison with the blue dot (¼ inch in diameter) indicates that the lesion is smaller. FIG. 4C shows the lesion on treatment day 9. At day 9, the lesion appeared smaller and flatter than on day 5, indicating that the healing process was continuing.

Oral Administration

Oral administration of the polysaccharide composition, prepared as described in Example 1, was also studied. An 89-year-old male subject received 150 ml daily of approximately 40 mg/ml polysaccharide composition, taken in divided doses over 4 hours. After 20 oral treatments, the skin cancer was significantly reduced (see FIG. 5).

A 94-year-old female subject with terminal metastatic squamous cell carcinoma was given one treatment of the polysaccharide composition orally (about 100 ml of approximately 40 mg/ml taken in divided doses over 4 hours). Measurements were preformed on the left posterior neck region. The measurable external part of the tumor was initially 1.75 inches in diameter on the evening of 7-26-08, then 1.5 inches in diameter on the morning of 7-27-08, and 1.25 inches on the evening of 7-28-08. On 8-1-08, the tumor was ⅞ inches in diameter with necrotic areas. See FIGS. 6A-C.

Example 12

Treatment of Chronic Lymphocytic Leukemia with a Polysaccharide Composition

An 87-year-old male subject with chronic lympocytic leukemia was treated with the polysaccharide composition prepared as described in Example 1. Specifically, each day, 4 drops were applied to surface skin every 15 minutes for a duration of 4 hours.

The initial blood count and cytology are shown below.
Collected Date: Aug. 21, 2006 15:10:00 Case #: SP-06-0007883

Diagnosis

Peripheral Blood for Flow Cytometric Analysis:
  B-cell chronic lymphocytic leukemia.
  Immunophenotype: CD5, CD19, CD20, CD22, CD23, kappa positive.
22 Aug. 2006 Pam Suwanjindar, MD
LSR/PS (Electronic Signature)
Comments
In addition to CLL, the peripheral smear and CBC data show findings suggestive of iron deficiency anemia.
Specimen
Peripheral blood for flow cytometry
Clinical Information
The patient is an 86-year-old male with absolute lymphocytosis.
CBC DATA: WBC 20.6 with 72% lymphocytes, hemoglobin 8, hematocrit 30, MCV 38, MCHC 27, and platelets 221.
Gross Description
Received from Dr. Kenyon through Legacy Bridgeview Laboratory, Newport, Oreg. is an EDTA tube of peripheral blood for flow cytometry studies. A Wright-stained peripheral smear is prepared and reviewed for morphologic correlation with flow cytometry results.
PS/lr
Microscopic
A Wright-stained peripheral smear demonstrates anisopoikilocytosis with scattered ovalocytes, microcytes, schistocytes, targets cells, and hypochromic cells. The WBC count is increased with an absolute lymphocytosis. The majority of lymphocytes are small with a condensed chromatin pattern. No significant prolymphocytes are seen. Platelets are adequate.
P S/lr
The post-treatment blood count and cytology follow. These show loss of CD20 marker with treatment, as well as reduction of white blood cells (WBC).

Surgical Pathology

Collected Date: Jul. 17, 2008 16:20:00 Case#: SP-08-0007308
Diagnosis
Peripheral Blood for Flow Cytometric Analysis:
  B-cell chronic lymphocytic leukemia.
  CD5, CD19, CD23, kappa positive and CD38 negative (see Comments).
18 Jul. 2008 Pam Suwanjindar, MD
MJC/PS (Electronic Signature)
Comments
The neoplastic B-cells do not express CD20 which may be due to previous chemotherapy.
Specimen
Peripheral blood for flow cytometry
Clinical Information
88-year-old male with history of B-cell chronic lymphocytic leukemia (CD5, CD19, CD20, CD23 and kappa positive).
CBC: WBC 9.3 with absolute lymphocyte count 5.0, hemoglobin 9, hematocrit 31, MCV 102, RDW 15, platelets 206.
Gross Description
Received from Samaritan Hematology and Oncology Consultant, Corvallis, Oreg., is an EDTA tube of peripheral blood for flow cytometry. A Wright—stained peripheral smear is prepared and reviewed for morphologic correlation with the flow cytometry results.
Microscopic
A Wright-stained peripheral smear demonstrates no significant anisopoikilocytosis. The WBC count is within the normal range with an absolute lymphocytosis of 5.0. The majority of lymphocytes are small with a condensed chromatin pattern. No significant large lyphoid cells or prolymphocytes are seen. Platelets are adequate.
PS/mjc Example 13

Effects Treatment with a Polysaccharide Composition on Various Parameters Associated with Aging Hair Restoration
  Oral Administration
  An 89-year-old male subject with apical balding for 30 years, where the remaining hair was white in color, received a 3-week oral treatment of 150 ml daily of approximate concentration of about 40 mg/ml polysaccharide composition (prepared as described in Example 1), taken in divided doses over 4 hours. After 3 weeks, this subject regrew hair in the bald area and developed 50% black hair, where he originally had white hair only. The color of the regrown hair was black, the color of this man's hair when young. See FIG. 7.

Topical Administration

With topical treatment twice daily of a solution 40 mg/ml of the polysaccharide composition, a 54-year-old male subject with mostly grey hair and a receding hair line re-established hair in the areas of thinning and recession. New hair was observed in the frontal hair line that was previously bald. The new hair was brown, rather than grey. Apical bald area was reduced from a diameter of 3 inches with new hair that brown. Mostly grey hair changed to color to brown over a 1-year treatment period.

Sub-Lingual Administration

Sub-lingual daily doses of approximately 20 mg over a 6-month period converted the hair color in a 68-year-old male subject from pure white to approximately 30% black and 70% white.

Hormonal Changes

Sub-lingual dose of 60 mg over a 4 hour period daily for 14 days changed the FSH and estradiol in a 63 year old woman as follows:

Pre-treatment: FSH: 78.5; Estradiol: 27
Post-treatment: FSH: 49.6; Estradiol: 23

Fat Loss

Three human subjects taking daily doses of approximately 20 mg polysaccharide composition noted reduced fat on the abdomen area after several weeks without changes in diet or exercise. This fat loss continued over a 3-month observational period.

Liver Spots

Topical application of a 40 mg/ml solution of polysaccharide composition to "liver spots" on the hands of a 55 year old man twice daily diminished and removed the spots over a few days of application, as well as improving elasticity and skin thickness.

Near Vision Improvement

Sub-lingual daily doses of approximately 20 mg polysaccharide composition produced near vision improvement in a 55-year-old male subject from over 1000 mm down to 140 mm for closest non-blurred vision over a 6-month treatment.

Improved Stamina, Muscle Mass, and Cognition

Three people (a 55-year-old man, a 68-year-old man, and an 85-year-old man) all taking sub-lingual doses of approximately 20 mg polysaccharide composition reported both subjective and objective improved mental function. Improvements were noted in memory, arithmetic skills, and logic. Stamina in exercise and muscle mass also improved slowly over several weeks.

Example 14

Additional Characterization Studies of Polysaccharide Composition

A polysaccharide composition according to the invention is referred to as "Galahad" in this example. A component of the polysaccharide composition is a red material that can be precipitated by addition of ammonium sulfate and can thus be separated from the carbohydrate in the composition. This red material is referred to as "Galahad Red" in this example.

Methods

Glycosyl Composition

Glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis.

Methyl glycosides were first prepared from dry sample provided by the client by methanolysis in 1 M HCl in methanol at 80° C. (18-22 hours), followed by re-N-acetylation with pyridine and acetic anhydride in methanol (for detection of amino sugars). The samples were then per-O-trimethylsilylated by treatment with Tri-Sil (Pierce) at 80° C. (0.5 hours). These procedures were carried out as previously described (Methods Enzymol. 230:1-15; York W. S., Darvill, A. G., McNeil, M., Stevenson, T. T., and Albersheim, P. (1985) *Methods Enzymol.* 118:3-40). GC/MS analysis of the TMS methyl glycosides was performed on an HP 5890 GC interfaced to a 5970 MSD, using a All Tech EC-1 fused silica capillary column (30m×0.25 mm ID).

Glycosyl Linkage

Hakamori Method:

For glycosyl linkage analysis, the dialyzed (10 kDa) sample was methylated by a modification of the method of Hakomori; depolymerized, reduced, and acetylated; and the resultant partially methylated alditol acetates (PMAAs) analyzed by gas chromatography-mass spectrometry (GC-MS) as described by York et al (1985) *Methods Enzymol.* 118:3-40. Briefly, An aliquot was taken from the sample after lyophilizing and dissolved in DMSO, 0.4 mL potassium dimsylate (2.0 M) was added. After 7 hours at room temperature on stirrer, the reaction mixture was cooled to 0° C., excess methyl iodide (0.7 mL) was added, and the tube sealed. Incubation was then continued for 24 h at room temperature. Following sample workup, the permethylated material was hydrolyzed using 2 M trifluoroacetic acid (3 h in sealed tube at 100° C.), reduced with $NaBD_4$, and acetylated using acetic anhydride/pyridine. The resulting PMAAs were analyzed on a Hewlett Packard 5890 GC interfaced to a 5970 MSD (mass selective detector, electron impact ionization mode); separation was performed on a 30 m Supelco 2330 bonded phase fused silica capillary column.

Size Exclusion Chromatography

Prior to loading, hydrophobic compounds were removed by C18 chromatography. Sample was loaded onto a Scc Waters C18 Sep Pak in 5% acetonitrile and eluted with water. A significant amount of red color remained at the top of the column and was eluted with 100% acetonitrile. This amounted to some 3 mg. Load and water wash were pooled and lyophilized to get approximately 20 mg of material. Interestingly, the red colored material which remained in the load was not soluble when resuspended at 10 mg/ml in 50 mM ammonium formate pH 5.06 and was retained when the material was passed through a 0.45 micron filter prior to chromatography. Filtered sample was loaded onto a 0.8×30 cm Toyopearl HW65 size exclusion column and eluted at 1.0ml/min in 50 mM ammonium formate pH 5.06. Detection was accomplished by means of an Agilent refractive index detector. Retention times were compared to standards of 1400 kD, 511 kD, 167 kD and 40 kD dextran.

Dynamic Light Scattering

Dextran standards (40, 167, 511, and 1400 kDa) and ammonium sulfate precipitated and dialyzed Galahad were prepared as 2 mg/mL solutions in water. The raw Galahad solution was diluted 5-fold with water. The samples were centrifuged for 15 min before analysis to remove particulates.

Measurements were carried out on a Protein Solutions DynaPro 99 dynamic light scattering machine at 25° C., using the Dynamics software, version 6.03. Laser power was set to 50% (standards) and 30% (samples), respectively.

Sampling interval was 5 s and a minimum of 20 measurements was collected and averaged.

Molecular Weight Determination Using SDOC PAGE of Galahad

Electrophoresis was performed on 8×10 cm 18% T 2.7% C mini gels using a Tris/Glycine (1:4.8 w/w) 0.25% sodium deoxycholate running buffer at 30 mA current and 400V potential. The gels were fixed in 40% ethanol 5% acetic acid 0.005% alcian blue 60 minutes then reincubated in the same solution overnight. Gels were then rinsed in water and oxidized in 0.7% sodium metaperiodate for 10 minutes. After this, they were rinsed 5 times in water and incubated 10 minutes in 10% Bio Rad silver reagent concentrate, rerinsed in water and developed in 3.2% Bio Rad developer until satisfactory staining was observed. Staining was stopped with 5% acetic acid.

Non-carbohydrate aromatic polymer component:

DEAE Purification 11.7 mg of dialyzed Galahad ammonium sulfate precipitate were loaded onto a 2.5 cm wide by 1 cm high DEAE column equilibrated in pH 6.8 20 mM Tris. Sample was loaded in 1.0 ml of equilibration buffer then washed with 3.0 ml of same. The column was then eluted with 5 ml 20 mM Tris 1M NaCl producing a colorless eluate. Finally, color was eluted from the column with 10 ml 25% NaOH. Eluate was dialyzed against RODI water and lyophilized to give a pink powder, SS120808. Note that some pink color was retained on column.

Butanol HCl Iron Digestion

Samples were treated according to the method of Porter and Chan (Phytochemistry (1986) v25(1) p223). Briefly, 3 mg of Galahad Ammonium sulfate precipitate or green tea extract (positive control) were suspended in butanol concentrated HCl 19:1 with 33 ul of 2% ferric ammonium sulfate then incubated at 100 celsius for 40 minutes. This reaction is judged to be positive if an increase in absorbance at 650 nm is observed.

Extraction of Low Molecular Weight Proanthocyanidins

Low molecular weight anthocyanidins were extracted using the prodelphinidin gallate extraction procedure of Nishioka et al. (Nishioka et al. Chem. Pharm Bulletin, v31(11) p3906-3914 1983) from 200 ul of Galahad 08:016 in parallel with 2 g of Da Li Shu green tea using 80% acetone which was then dried to a minimal volume and filtered. No precipitate was noted upon addition of acetone to Galahad. Samples were then extracted 3 times with 1 volume ethyl acetate. 0.2 mg of material was obtained from Galahad and approximately 200 mg from the green tea.

TLC was performed on Whatman HPTLC plates using either chloroform:methanol 4:1 or benzene:acetone:acetic acid 4:1:1 as developing solvents. Plates contained a UV fluorescent dye and were examined for the presence of UV absorbing compounds under UV illumination then stained with Ceric ammonium nitrate ammonium molybdate.

Isolated phloroglucinolysis products were analyzed by spotting onto a matrix of 2,5 dihydroxybenzoic acid. MS analysis of the products was performed on an Applied biosystems Voyager MALDI run in the positive ion mode.

UV/Visible Spectroscopy

Samples were suspended in 0.5M HCl in Methanol and spectra were recorded on a Beckman DU600 UV visible spectrophotometer. Periodate oxidation was accomplished by suspending sample in approximately 40 ul $HIO_4$ then diluting solution into methanolic HCl for spectrophotometry.

CHN Analysis

Carbon Hydrogen Nitrogen Analysis was performed by the Chemical Analysis Laboratory of the UGA.

Protein and Composition Analysis of Galahad Ammonium Sulfate Precipitate

Ammonium Sulfate Precipitation

The contents of 1 vial of Galahad were precipitated with 5 volumes of saturated ammonium sulfate. Sample was incubated on ice. Pellet was harvested by centrifugation.

Protein Assay

Samples were analyzed for protein using the Bio Rad Microplate protein assay. Briefly, 10 ul of sample or BSA standard were incubated with 200 ul Bio Rad reagent (diluted 1:4 with water) for 5 minutes at room temperature. Absorbance at 650 nm was monitored using a Molecular Devices plate reader.

Heptafluorobutyryl (HFB) Composition

Glycosyl composition analysis was performed by combined gas chromatography/mass spectrometry (GC/MS) of the HFB derivatives of the monosaccharide methyl glycosides produced from the sample by acidic methanolysis.

Methyl glycosides were first prepared from dry sample provided by the client by methanolysis in 1M HCl, in methanol at 80° C. (18-22 hours), followed by acetylation with heptafluorobutyric acid anhydride. GC/MS analysis of the HFB methyl glycosides was performed on an HP 5890 GC, using a CPSil-5 Low Bleed capillary column (30m× 0.25 mm ID).

TLC

The initial solvent used for TLC of intact Galahad Red was the strong solvent used for LC—methanol:water:acetic acid 48:1:1. This was used to develop silica gel Kieselgel 60 F254 plates which were examined for visible TLC bands, illuminated with UV light to find bands absorbing in the UV spectrum then stained with ceric ammonium nitrate ammonium molybdate to locate other, non UV absorbing materials.

Ultrafiltration

To see whether Galahad Red is approximately the same size as the compound characterized in the laser light scattering experiments, we ultrafiltered 50 ul aliquots of Galahad lot 08:016 through filters of 10 kD and 100 kD MWCO. Filtrates were inspected visually for color.

Phloroglucinolysis

Two different methods of phloroglucinolysis were used. For breakdown of the components of a standard compound, Carlo Rossi Burgundy, we used incubation in 1M HCl in methanol at 80° C. for 2 hours in the presence of 50 mg phloroglucinol. All hydrolyses of Galahad Red were made using 50 mg/ml phloroglucinol in 1M HCl in methanol 80° C. with overnight incubation. Reactions were analyzed by TLC on silica gel TLC plates using chloroform methanol 9:1 and in some cases chloroform methanol 0.25% KCl 5:4:1 as a developing solvent. Visualization was accomplished either by the use of a UV lamp and by staining with ceric ammonium nitrate/ammonium molybdate in ethanol sulfuric acid.

MALDI-Ms for Determination of Molecular Weight

Isolated phloroglucinolysis products were analyzed by spotting onto a matrix of 2,5 dihydroxybenzoic acid. MS analysis of the products was performed on an Applied biosystems Voyager MALDI run in the positive ion mode.

Purification of Galahad Red on Butyl Sepharose 200 ul of Galahad lot 08:016 were loaded on a 08×8 cm column of butyl sepharose equilibrated in water. Column was then eluted with 5 ml of water giving some colored compounds but leaving most color at the top of the column. Column was then eluted with methanol, isopropanol, hexane:isopropanol 1:1, 1M methanolic HCl, n butanol, Isopropanol with 1% TEA and 1% HOAc, pyridine, and phenol: 0.5M methanolic HCl 1:1. Only the phenol methanolic HCL eluted any significant color and a substantial amount of material was left on the column.

Amino Acid Composition

Amino acid composition analysis was performed by combined gas chromatography/mass spectrometry (GC/MS) of the heptafluorobutyrate (HFB) derivatives of the amino acid isoamyl esters produced from the sample by acidic transesterification as per the method of Pons et al. (Pons et al. Biochemistry 2003, v42 p 8342-8353).

Briefly, samples were first hydrolyzed in 6M HCl overnight at 110° C. 1nmol of norleucine internal standard was then added and samples were dried under a gentle stream of nitrogen. Samples were then resuspended in 0.5M methanolic HCl and incubated at 80° C. overnight. Transesterification was then performed in 1.5M isoamyl HCl at 100° C. overnight followed by evaporation under nitrogen and acylation with heptafluorobutyric acid anhydride (50 ul in 200 ul acetonitrile). GC/MS analysis of the amino acid derivatives was performed on an HP 5890 GC interfaced to a 5970 MSD, using a CP Sil5 capillary column (30m×0.25 mm ID) and a temperature gradient of 90 to 260° C. at 5° C./min.

Biological Activity of Separated Material

CPE Assay

Human foreskin fibroblasts (HFF) cells were plated into six well plates and incubated at 37° C. with 5% $CO_2$ and 90% humidity. Two days later, drug was serially diluted 1:5 in MEM with 2% FBS using six concentrations of drug. The virus to be used was diluted in MEM containing 10% FBS to a desired concentration which gave 20-30 plaques per well. The media was then aspirated from the wells and 0.2 ml of virus was added to each well in triplicate with 0.2 ml of media being added to control wells. The plates were then incubated for one hour with shaking every fifteen minutes and drug was added to appropriate wells. After an incubation period of 3 days, the cells were stained with 0.1% crystal violet in 20% methanol, washed with PBS, and the plaques counted using a stereomicroscope. Plaque number in drug treated and untreated wells, were used to calculate $EC_{50}$ values.

Direct Inactivation

Two days prior to use, HFF cells were seeded in six well plates and incubated at 37° C. On the day of the assay the virus to be used was diluted in MEM with 10% FBS to a desired concentration which would yield 40-60 plaques. The drug was at an initial concentration of 100% solution. This was serially diluted 1:5 to give six concentrations in 0.4 ml of media. Then 0.4 ml of virus was added to each concentration of drug to yield the final concentrations ranging from 50% to 0.016%, and 0.4 ml of MEM with 10% FBS was added to the virus control and cell control tubes. The mixtures were incubated in a 37° C. water bath for 1 hour. The mixtures were then placed on ice. The media was aspirated from the wells of confluent HFF cells and 0.2 ml of the mixture was added to the appropriate wells in duplicate. The plates were then incubated for 1 hour at 37° C. and shaken every 15 minutes. After the incubation, 2.0 ml of MEM with 2% FBS and pooled human sera was added to each well. The plates were then incubated for 3 days, after which the cells were stained with 1 ml per well of 0.1% crystal violet/20% methanol the wells washed with PBS, and the plaques counted using a stereomicroscope. The $EC_{50}$ values were calculated using a computer program.

Neutral Red Uptake Assay

Compound concentration that reduced the uptake of the neutral red vital dye by 50% ($CC_{50}$) was used as a measure of toxicity. Briefly, 2.5×10⁴ cells were seeded into each well of 96 well tissue culture plates containing growth media and incubated for 24 h at 37° C. in a $CO_2$ incubator. Media containing compound dilutions were then added to the plates, which were incubated for an additional 7 days. Cell monolayers were stained with a 0.01% solution of neutral red in PBS and incubated for 1 hour. Cells were washed and dye internalized by the cells was solubilized in 100 µl of a 50% ethanol solution supplemented with 1% glacial acetic acid and the optical density was determined at 540 nm. $EC_{50}$ values were calculated by standard methods (as per Kern, E. R., N. L. Kushner, C. B. Hartline, S. L. Williams-Aziz, E. A. Harden, S. Zhou, J. Zemlicka, and M. N. Prichard. 2005. In vitro activity and mechanism of action of methylenecyclopropane analogs of nucleosides against herpesvirus replication. Antimicrob Agents Chemother 49:1039-45).

Test for Tannin, Purification and Semipreparative Phloroglucinolysis on Galahad Red Tannin Test 500 ul of sample or Carlo Rossi Burgundy (positive control) were added to 1 ml of 1 mg/ml BSA suspended in either 50 mM tricine pH 8.0 or pH 5.0 ammonium formate and observed for precipitation. As a control, buffer without BSA was added.

Purification 20 ml of Galahad TK020209 were precipitated with 17 ml saturated ammonium sulfate. The deep red precipitate from centrifugation (15 minutes 3000 rpm) was then suspended in 100 mM TFA pH 1.3 and recentrifuged. Pellet was then dissolved in 40 ml water+1 ml concentrated ammonia and recentrifuged. Little material was pelleted at this stage and the supernatant was lyophilized to get 740 mg Galahad Red SS030909A.

Semipreparative Phloroglucinolysis 55 mg of Galahad Red SS030909a were suspended in 3 ml 50 mg/ml phloroglucinol 1M methanolic HCl and incubated overnight at 80° C. Reaction was then partially dried, diluted with 10 volumes of water and loaded onto a 20 ml C18 sep pak (Waters). Column was then eluted with 30 ml acetonitrile in 4 fractions, 10 ml 15% acetonitrile, then 20 ml 100% acetonitrile in 3 fractions. Significant color was noted in the first 2 acetonitrile fractions. Column was then eluted with 8 ml benzene isopropanol, 10 ml of same and 10 ml of same with 1% TFA. A bright yellow color was observed in benzene isopropanol wash 2 and a red color in benzene isopropanol TFA wash.

Material eluting in acetontrile showed a series of bands by TLC in benzene acetone acetic acid 5:4:1 (ceric ammonium nitrate stain). Half of the eluate was purified by preparative TLC on a 20×20 cm Analtech Silica gel H TLC plate. 7 different bands of material were scraped from the plate and eluted in methanol. These are numbered from highest Rf to lowest with 7 being material retained at the origin.

Mass Spectrometry MALDI-MS Both analyzed on an Applied Biosystems 4700 MALDI TOF MS run in both the positive and negative ion modes using DHB as a matrix. Samples were spotted from methanol.

Phloroglucinolysis

Two different methods of phloroglucinolysis were used. For breakdown of the components of a standard compound, Carlo Rossi Burgundy, we used incubation in 1M HCl in methanol at 80° C. for 2 hours in the presence of 50 mg phloroglucinol. All hydrolyses of Galahad Red were made using 50 mg/ml phloroglucinol in 1M HCl in methanol 80° C. with overnight incubation. Reactions were analyzed by TLC on silica gel TLC plates using chloroform methanol 9:1 and in some cases chloroform methanol 0.25% KCl 5:4:1 as a developing solvent. Visualization was accomplished either by the use of a UV lamp and by staining with ceric ammonium nitrate/ammonium molybdate in ethanol sulfuric acid.

Isolation of Phloroglucinolysis Reaction Products

Reaction mixes were dry loaded onto columns of Iatrobeads for flash chromatography. Initial solvent was chloroform, followed by chloroform methanol 9:1 then 4:1.

NMR

Proton NMR was acquired using a Varian Inova 600 MHz instrument at 25° C. using a 3-mm cryogenic probe. Spectra were recorded in CDCl$_3$ or CD$_3$OD as solvent. Chemical shifts were referenced to the respective residual solvent signal (CDCl$_3$: 7.26 ppm, 77.16 ppm; CD$_3$OD: 3.31 ppm, 49.00 ppm)

Solid Phase Extraction (SPE) with Sep Pak C18

Galahad (070609) was lyophilized. Solid material was dissolved in 10 mM ammonium acetate and loaded on Sep-Pak C18 catridge, followed by elution with 10 mM ammonium acetate, water and acetontrile as illustrated in Scheme 1. The hydrophilic and hydrophobic fractions collected were lyophilized and analyzed by $^1$H NMR.

Scheme 1: Solid phase extraction of Galahad with Sep-Pak C18

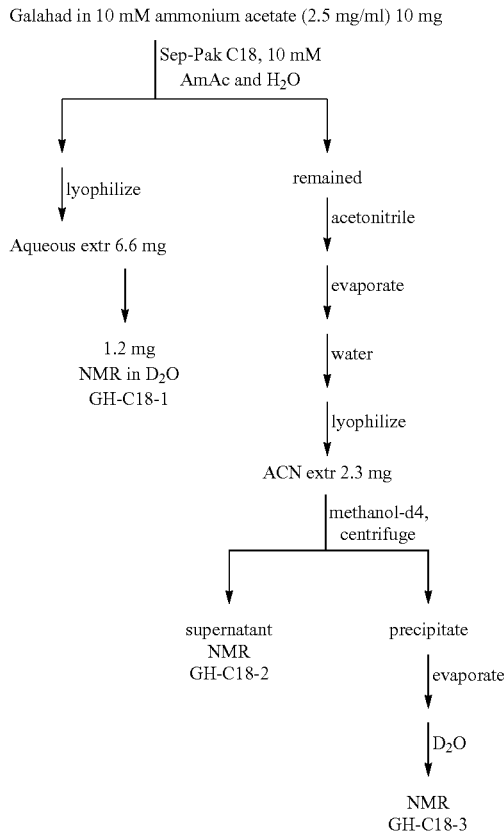

Fractional Precipitation with Methanol and Iso-Propanol

Galahad (070609) was lyophilized. Solid material was dissolved in 10 mM ammonium acetate and precipitated in 90% methanol. The methanol soluble part was evaporated, re-dissolved in 10 mM ammonium acetate and precipitated in 80% iso-propanol as shown in Scheme 2. All fractions were analyzed by GC/MS after TMS derivatization or by $^1$H NMR.

Scheme 2: Fractional precipitation of Galahad in alcohol

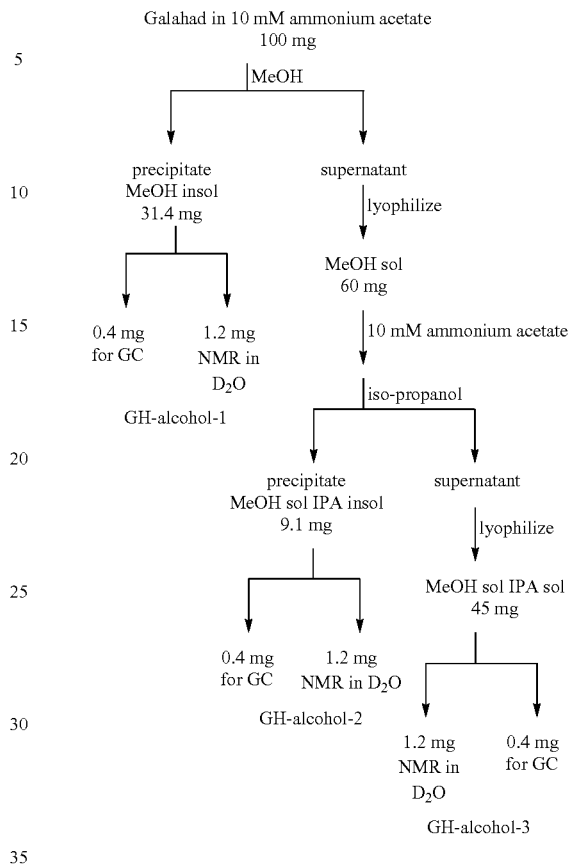

NMR Spectroscopy of Monosaccharide Methyl Glycosides

Samples were dissolved in 0.2 mL D$_2$O or methanol-d4. 1D proton NMR spectra were acquired on a Varian Inova-600 MHz spectrometer at 298 K (25° C.) using standard Varian pulse sequences. Proton chemical shifts were measured relative to internal acetone ($\delta_H$=2.225 ppm). The sample was dissolved in DMSO and again permethylated by the method of Ciukanu and Kerek (1984) *Carbohydr. Res.* 131:209-217 (treatment with sodium hydroxide and methyl iodide in dry DMSO). The sample was subjected to the NaOH base for 10 minutes then methyl iodide was added and left for 10 minutes. More methyl iodide was then added for 40 minutes. The base was then added for 10 minutes and finally more methyl iodided was added for 40 minutes. This addition of more methyl iodide and NaOH base was to insure complete methylation of the polymer. Following sample workup, the permethylated material was hydrolyzed using 2 M trifluoroacetic acid (2 h in sealed tube at 121° C.), reduced with NaBD$_4$, and acetylated using acetic anhydride/trifluoroacetic acid. The resulting PMAAs were analyzed on a Hewlett Packard 5890 GC interfaced to a 5970 MSD (mass selective detector, electron impact ionization mode); separation was performed on a 30 m Supelco 2330 bonded phase fused silica capillary column.

Results

Initial studies of Galahad focused on an arabinan which is present in the sample. According to glycosyl composition analysis before and after ammonium sulfate precipitation the arabinan precipitates together with the material producing the red color.

Glycosyl Composition

TABLE D1

Glycosyl Composition Analysis of Galahad

| Sample | Glycosyl residue | Mass (μg) | Mole %[1] |
|---|---|---|---|
| Crude Galahad | Rhamnose (Rha) | 25.5 | 7.1 |
| | Fucose (Fuc) | n.d. | n.d. |
| | Arabinose (Ara) | 141.0 | 42.9 |
| | Xylose (Xyl) | 8.5 | 2.6 |
| | Glucuronic Acid (GlcUA) | 17.3 | 4.1 |
| | Galacturonic acid (GalUA) | 103.1 | 24.3 |
| | Mannose (Man) | 14.1 | 3.6 |
| | Galactose (Gal) | 42.1 | 10.7 |
| | Glucose (Glc) | 18.8 | 4.8 |
| | N Acetyl Galactosamine (GalNAc) | n.d. | n.d. |
| | N Acetyl Glucosamine (GlcNAc) | n.d. | n.d. |
| | Heptose (Hep) | n.d. | n.d. |
| | 3 Deoxy-2-manno-2 Octulsonic acid (KDO) | n.d. | n.d. |
| | Sum | 370 | 100 |
| Galahad 08:016 A.S. Ppt | Rhamnose (Rha) | 0.9 | 2.1 |
| | Fucose (Fuc) | n.d. | n.d. |
| | Arabinose (Ara) | 31.6 | 77.8 |
| | Xylose (Xyl) | n.d. | n.d. |
| | Glucuronic Acid (GlcUA) | n.d. | n.d. |
| | Galacturonic acid (GalUA) | 4.7 | 8.9 |
| | Mannose (Man) | 0.5 | 1.0 |
| | Galactose (Gal) | 4.1 | 8.4 |
| | Glucose (Glc) | 0.9 | 1.8 |
| | N Acetyl Galactosamine (GalNAc) | n.d. | n.d. |
| | N Acetyl Glucosamine (GlcNAc) | n.d. | n.d. |
| | Heptose (Hep) | n.d. | n.d. |
| | 3 Deoxy-2-manno-2 Octulsonic acid (KDO) | n.d. | n.d. |
| | Sum | 43 | 100 |

TABLE D2

Average of the Glycosyl composition data. Mol % of sugar in the carbohydrate component:

| Sugar | Low % | High % | Mean ± 3SD |
|---|---|---|---|
| Arabinose (Ara) | 33.2 | 74.2 | 53.7 ± 20.5 |
| Rhamnose (Rha) | 0 | 9.3 | 4.2 ± 5.1 |
| Xylose (Xyl) | 0 | 4.4 | 1.7 ± 2.7 |
| Glucuronic Acid (GlcUA) | 0 | 7.3 | 1.7 ± 5.6 |
| Galacturonic acid (GalUA) | 3.4 | 35.8 | 19.6 ± 16.2 |
| Mannose (Man) | 0 | 6.0 | 2.9 ± 3.1 |
| Galactose (Gal) | 1.9 | 19.5 | 10.7 ± 8.8 |
| Glucose (Glc) | 0 | 12.5 | 5.4 ± 7.1 |

Glycosyl Linkage

TABLE D3

Glycosyl Linkage Analysis of Galahad (CCRC Code DK121806)

| Glycosyl Residue | Percentage Present |
|---|---|
| terminally linked arabinofuranosyl residue (t-Araf) | 14.9% |
| 2-linked arabinofuranosyl residue (2-Araf) | 9.6% |
| 2-linked rhamnopyranosyl residue (2-Rhap) | 0.3% |
| 3-linked arabinofuranosyl residue (3-Araf) | 3.2% |
| terminally linked galactopyranosyl residue (t-Gal) | 2.1% |
| 5-linked arabinofuranosyl residue (5-Araf) | 15.8% |
| 3-linked glucopyranosyl residue (3-Glc)&2,4-linked rhamnopyranosyl residue (2,4-Rhap) | 0.7% |
| 2-linked glucopyranosyl residue (2-Glc) | 1.2% |
| 4-linked mannopyranosyl residue (4-Man) | 1.4% |
| 3,5-linked arabinofuranosyl residue (3,5-Araf) | 6.9% |
| 2,5-linked arabinofuranosyl residue (2,5-Araf) | 5.3% |
| 4-linked glucopyranosyl residue (4-Glc) | 4.7% |
| 2,3,5-linked arabinofuranosyl residue (3,5-Araf)& 2,3,4-linked arabinopyranosyl residue (2,3,4-Arap) | 27.0% |
| 4-linked galactouronic acid (4-gal A) | 1.5% |
| 3,6-linked galactopyranosyl residue (3,6-Gal) | 0.4% |
| 2,3,4,6-linked mannopyranosyl residue (2,3,4,6-Man) | 0.7% |
| 2,3,4,6-linked galactopyranosyl residue (2,3,4,6-Gal)&2,3,4-linked galactouronic acid | 2.1% |
| 2,3,4,6-linked glucopyranosyl residue (2,3,4,6-Glc) | 2.2% |

TABLES D4

Glycosyl Linkage Analysis of various lots in detail

| Glycosyl Residue | Percentage Present |
|---|---|
| terminally linked rhamnopyranosyl residue (t-Rha) | 1.42 |
| terminally linked arabinofuranosyl residue (t-Araf) | 21.90 |
| terminally linked arabinopyranosyl residue (t-Ara) | 0.24 |
| terminally linked xylopyranosyl residue (t-Xyl) | 0.67 |
| 2 linked rhamnopyranosyl residue (2-Rha) | 3.48 |
| terminally linked manopyranosyl residue (t-Man) | 1.12 |
| terminally linked glucopyranosyl residue (t-Glc) | 4.35 |
| 3 linked arabinofuranosyl residue (3-Araf) | 5.25 |
| terminally linked galactopyranosyl residue (t-Gal) | 6.36 |
| 4 linked arabinopyranosyl residue or 5-linked arabinofuranosyl residue (4-Ara or 5-Araf) | 14.71 |
| 4 linked xylopyranosyl residue (4-Xyl) | 0.71 |
| 2,4 linked rhamnopyranosyl residue (2,4-Rha) | 2.81 |
| 2 linked manopyranosyl residue (2-Man) | 4.40 |
| 2 linked glucopyranosyl residue & 2-gulcuronic acid residue (2-Glc & 2-GlcA) | 0.18 |
| 3 linked galactopyranosyl residue (3-Gal) | 3.36 |
| 4 linked manopyranosyl residue (4-Man) | 0.45 |
| 3,4 linked arabinopyranosyl residue or 3,5 linked arabinofuranosyl residue (3,4-Arap or 3,5-Araf) | 6.62 |
| 4 linked galactouronic acid residue & 4 linked galactopyranosyl residue (4-Gal A & 4-Gal) | 4.41 |
| 2,4 linked arabinopyranosyl residue or 2,5 linked arabinofuranosyl residue (2,4-Arap or 2,5-Araf) | 1.07 |
| 4-linked glucopyranosyl residue & 4-Glucuronic acid residue (4-Glc & 4-GlcA) | 4.73 |
| 2,3 linked manopyranosyl residue (2,3-Man) | 1.62 |
| 6-linked galactopyranosyl residue (6-Gal) | 1.17 |
| 2,3,4 linked arabinopyranosyl residue (2,3,4-Ara) | 2.33 |
| 3,4 linked glucopyranosyl residue (3,4-Glc) | 0.47 |
| 2,6 linked manopyranosyl residue (2,6-Man) | 0.69 |
| 4,6 linked glucopyranosyl residue (4,6-Glc) | 0.24 |
| 4,6 linked galactouronic acid residue & 4,6 linked galactopyranosyl residue (4,6-Gal A & 4,6-Gal) | 0.11 |
| 3,6 linked galactopyranosyl residue (3,6-Gal) | 5.16 |
| TK070609 | |
| Terminally linked Rhamnopyranosyl residue (t-Rha) | 1.7 |
| Terminally linked Arabinofuranosyl residue (t-Araf) | 11.6 |
| Terminally linked Fucopyranosyl residue (t-Fuc) | 0.1 |
| Terminally linked Arabinopyranosyl residue (t-Ara) | 1.0 |
| Terminally linked Xylopyranosyl residue (t-Xyl) | 0.8 |
| 2 linked Rhamnopyranosyl residue (2-Rha) | 3.5 |
| Terminally linked Manopyranosyl residue & 4 linked Rhamnopyranosyl residue (t-Man + 4-Rha) | 2.6 |
| Terminally linked Glucopyranosyl residue & Terminally linked Glucuronic Acid residue (t-Glc + t-GlcA) | 3.3 |
| 3 linked Arabinofuranosyl residue (3-Araf) | 3.9 |
| Terminally linked Galactopyranosyl residue & Terminally linked Galactouronic Acid residue (t-Gal + t-GalA) | 8.7 |
| 4 linked Arabinopyranosyl residue or 5 linked Arabinofuranosyl residue (4-Arap or 5-Araf) | 14.6 |
| 4 linked Xylopyranosyl residue (4-Xyl) | 1.1 |
| 2,3-Rhamnopyranosyl residue (2,3-Rha) | 0.1 |
| 2,4-Rhamnopyranosyl residue (2,4-Rha) | 2.4 |

TABLES D4-continued

Glycosyl Linkage Analysis of various lots in detail

| Glycosyl Residue | Percentage Present |
|---|---|
| 2 linked Manopyranosyl residue (2-Man) | 3.0 |
| 2 linked Glucopyranosyl residue & 2 linked Glucuronic Acid residue (2-Glc + 2-GlcA) | 0.4 |
| 3 linked Galactopyranosyl residue (3-Gal) | 2.9 |
| 4 linked Manopyranosyl residue (4-Man) | 1.1 |
| 3,4 linked Arabinopyranosyl or 3,5 linked Arabinofuranosyl (3,4-Arap or 3,5-Araf) | 6.4 |
| 6 linked Glucuronic Acid residue & 6 linked Glucopyranosyl residue (6-GlcA + 6-Glc) | 0.5 |
| 4 linked Galacturonic Acid residue & 4 linked Galactopyranosyl residue (4-GalA + 4-Gal) | 7.5 |
| 2,4 linked Arabinopyranosyl or 2,5 linked Arabinofuranosyl (2,4-Arap or 2,5-Araf) | 1.4 |
| 4 linked Glucuronic Acid residue & 4 linked Glucopyranosyl residue (4-GlcA + 4-Glc) | 7.3 |
| 2,3 linked Manopyranosyl residue (2,3-Man) | 0.9 |
| 6 linked Galactopyranosyl residue (6-Gal) | 1.1 |
| 2,3,4 linked Arabinopyranosyl residue (2,3,4-Ara) | 4.0 |
| 3,4 linked Galacturonic Acid residue & 3,4 linked Galactopyranosyl residue (3,4-Gal + 3,4-GalA) | 1.2 |
| 3,4 linked Glucuronic Acid residue & 3,4 linked Glucopyranosyl residue (3,4-Glc + 3,4-GlcA) | 0.4 |
| 2,4 linked Manopyranosyl residue (2,4-Man) | 0.1 |
| 2,4 linked Galacturonic Acid residue & 2,4 linked Galactopyranosyl residue (2,4-GalA + 2,4-Gal) | 0.9 |
| 4,6 linked Manopyranosyl residue (4,6-Man) | 0.1 |
| 4,6 linked Glucopyranosyl residue & 4,6 linked Glucuronic Acid residue (4,6-Glc + 4,6-GlcA) | 0.5 |
| 4,6 Galacturonic acid residue & 4,6-Galactopyranosyl residue (4,6-GalA + 4,6-Gal) | 0.5 |
| 3,6 linked Galactopyranosyl residue (3,6-Gal) | 4.1 |
| TK081109 | |
| Terminally linked Rhamnopyranosyl residue (t-Rha) | 1.8 |
| Terminally linked Arabinofuranosyl residue (t-Araf) | 16.6 |
| Terminally linked Fucopyranosyl residue (t-Fuc) | 0.1 |
| Terminally linked Arabinopyranosyl residue (t-Ara) | 0.8 |
| Terminally linked Xylopyranosyl residue (t-Xyl) | 0.6 |
| 2 linked Rhamnopyranosyl residue (2-Rha) | 3.5 |
| Terminally linked Manopyranosyl residue & 4 linked Rhamnopyranosyl residue (t-Man + 4-Rha) | 2.5 |
| Terminally linked Glucopyranosyl residue & Terminally linked Glucuronic Acid residue (t-Glc + t-GlcA) | 3.3 |
| 3 linked Arabinofuranosyl residue (3-Araf) | 4.1 |
| Terminally linked Galactopyranosyl residue & Terminally linked Galacturonic Acid residue (t-Gal + t-GalA) | 10.0 |
| 4 linked Arabinopyranosyl residue or 5 linked Arabinofuranosyl residue (4-Arap or 5-Araf) | 15.1 |
| 4 linked Xylopyranosyl residue (4-Xyl) | 0.7 |
| 2,3-Rhamnopyranosyl residue (2,3-Rha) | 0.0 |
| 2,4-Rhamnopyranosyl residue (2,4-Rha) | 2.4 |
| 2 linked Manopyranosyl residue (2-Man) | 4.6 |
| 2 linked Glucopyranosyl residue & 2 linked Glucuronic Acid residue (2-Glc + 2-GlcA) | 0.4 |
| 3 linked Galactopyranosyl residue (3-Gal) | 2.2 |
| 4 linked Manopyranosyl residue (4-Man) | 0.5 |
| 3,4 linked Arabinopyranosyl or 3,5 linked Arabinofuranosyl (3,4-Arap or 3,5-Araf) | 5.4 |
| 6 linked Glucuronic Acid residue & 6 linked Glucopyranosyl residue (6-GlcA + 6-Glc) | 0.2 |
| 4 linked Galacturonic Acid residue & 4 linked Galactopyranosyl residue (4-GalA + 4-Gal) | 7.5 |
| 2,4 linked Arabinopyranosyl or 2,5 linked Arabinofuranosyl (2,4-Arap or 2,5-Araf) | 0.7 |
| 4 linked Glucuronic Acid residue & 4 linked Glucopyranosyl residue (4-GlcA + 4-Glc) | 9.5 |
| 2,3 linked Manopyranosyl residue (2,3-Man) | 1.0 |
| 6 linked Galactopyranosyl residue (6-Gal) | 0.7 |
| 2,3,4 linked Arabinopyranosyl residue (2,3,4-Ara) | 1.8 |
| 3,4 linked Galacturonic Acid residue & 3,4 linked Galactopyranosyl residue (3,4-Gal + 3,4-GalA) | 0.8 |
| 3,4 linked Glucuronic Acid residue & 3,4 linked Glucopyranosyl residue (3,4-Glc + 3,4-GlcA) | 0.2 |
| 2,4 linked Manopyranosyl residue (2,4-Man) | 0.1 |
| 2,4 linked Galacturonic Acid residue & 2,4 linked Galactopyranosyl residue (2,4-GalA + 2,4-Gal) | 0.6 |
| 4,6 linked Glucopyranosyl residue & 4,6 linked Glucuronic Acid residue (4,6-Glc + 4,6-GlcA) | 0.3 |
| 4,6 Galacturonic acid residue & 4,6-Galactopyranosyl residue (4,6-GalA + 4,6-Gal) | 0.4 |
| 3,6 linked Galactopyranosyl residue (3,6-Gal) | 1.8 |
| TK020209 | |
| Terminally linked Rhamnopyranosyl residue (t-Rha) | 2.2 |
| Terminally linked Arabinofuranosyl residue (t-Araf) | 20.7 |
| Terminally linked Arabinopyranosyl residue (t-Ara) | 1.1 |
| Terminally linked Xylopyranosyl residue (t-Xyl) | 1.3 |
| 2 linked Rhamnopyranosyl residue (2-Rha) | 3.0 |
| Terminally linked Manopyranosyl residue & 4 linked Rhamnopyranosyl residue (t-Man + 4-Rha) | 2.5 |
| Terminally linked Glucopyranosyl residue & Terminally linked Glucuronic Acid residue (t-Glc + t-GlcA) | 6.0 |
| 3 linked Arabinofuranosyl residue (3-Araf) | 3.4 |
| Terminally linked Galactopyranosyl residue & Terminally linked Galacturonic Acid residue (t-Gal + t-GalA) | 6.9 |
| 4 linked Arabinopyranosyl residue or 5 linked Arabinofuranosyl residue (4-Arap or 5-Araf) | 18.4 |
| 4 linked Xylopyranosyl residue (4-Xyl) | 1.0 |
| 2,4-Rhamnopyranosyl residue (2,4-Rha) | 2.2 |
| 2 linked Manopyranosyl residue (2-Man) | 4.6 |
| 2 linked Glucopyranosyl residue (2-Glc) | 0.4 |
| 3 linked Galactopyranosyl residue (3-Gal) | 2.9 |
| 4 linked Manopyranosyl residue (4-Man) | 2.9 |
| 3,4 linked Arabinopyranosyl or 3,5 linked Arabinofuranosyl (3,4-Arap or 3,5-Araf) | 5.4 |
| 2 linked Galactopyranosyl residue & 6 linked Manopyranosyl residue (2-Gal + 6-Man) | 0.5 |
| 4 linked Galacturonic Acid residue & 4 linked Galactopyranosyl residue (4-GalA + 4-Gal) | 2.4 |
| 2,4 linked Arabinopyranosyl or 2,5 linked Arabinofuranosyl (2,4-Arap or 2,5-Araf) | 0.9 |
| 4 linked Glucuronic Acid residue & 4 linked Glucopyranosyl residue (4-GlcA + 4-Glc) | 3.5 |
| 2,3 linked Manopyranosyl residue (2,3-Man) | 1.1 |
| 6 linked Galactopyranosyl residue (6-Gal) | 1.1 |
| 2,3,4 linked Arabinopyranosyl residue (2,3,4-Ara) | 1.9 |
| 3,4 linked Galacturonic Acid residue & 3,4 linked Galactopyranosyl residue (3,4-Gal + 3,4-alA) | 0.7 |
| 4,6 linked Manopyranosyl residue (4,6-Man) | 0.3 |
| 4,6 linked Glucopyranosyl residue & 4,6 linked Glucuronic Acid residue (4,6-Glc) | 0.3 |
| 3,6 linked Galactopyranosyl residue (3,6-Gal) | 2.7 |

The glycosyl composition data shows that the Galahad carbohydrate portion is made of approximately 53% of arabinose, 19.6% of galacturonic acid, 10% of galactose, 5.4% of glucose, 4.2% of rhamnose, 1.7% of xylose, 1.7% of glucuronic acid and 2.8% of mannose. The presence of the galacturonic acid and glucuronic acid indicates that Galahad contains acidic residues as well as neutral monosaccharide residues.

The linkage analysis gives information on the type of glycosidic linkages present in the polysaccharide. The glycosyl composition showed that the carbohydrate portion of the sample is mainly arabinose with a small amount of an unidentified residue and trace amounts of mannose, galactose, and rhamnose. These data suggest that the main carbohydrate component in the sample is an arabinan. The linkage data shows that the arabinan consist of a backbone of 5-Arabinose and 3,5-Arabinose with side chains of terminal arabinose and possibly 2-Arabinose backbone.

Size Exclusion Chromatography

Figure 8:
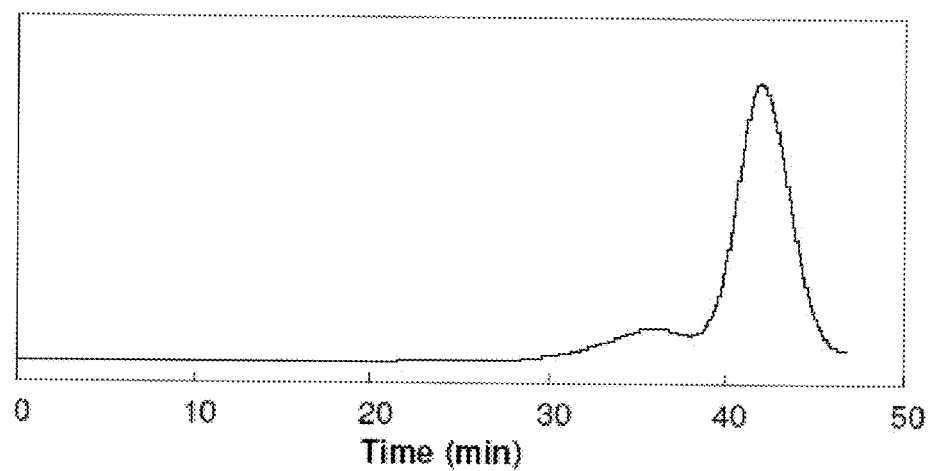
FIG. 8 shows the results of Example 14: Size Exclusion Chromatography. The filtered polysaccharide was purified on a HW 65 column, and 2-min fractions were collected. Elution was monitored by refractive index detection which is not specific for carbohydrate. However, it is estimated to be below 5 kD and made of smaller oligosaccharides.
Figure 9:
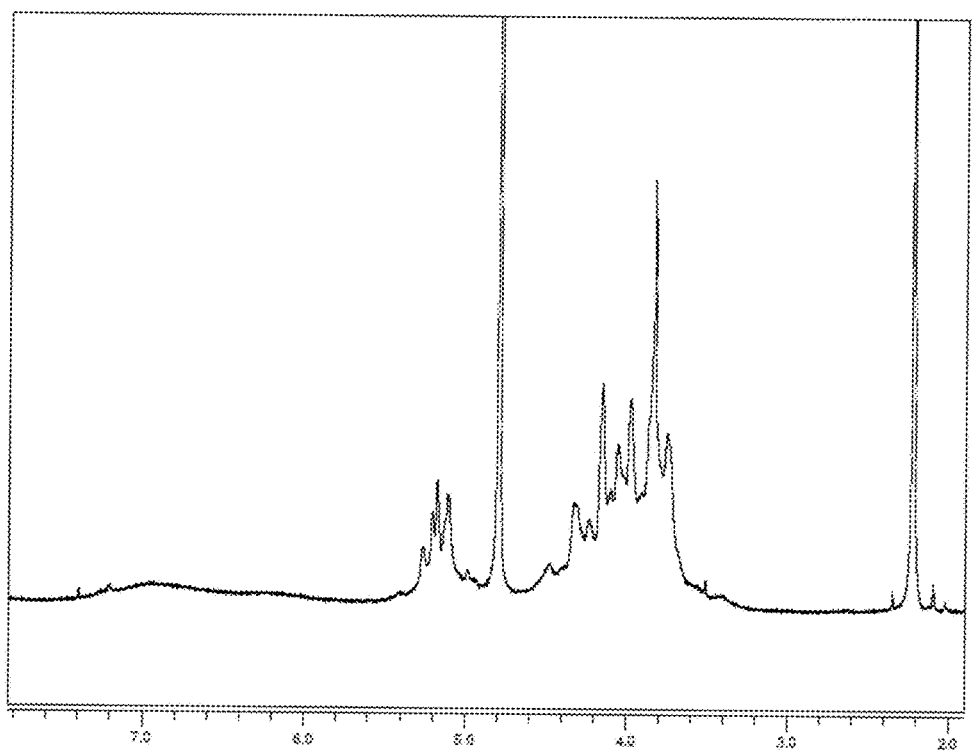
FIG. 9 shows the results of Example 14: 1-D Proton NMR Spectrum of Galahad Lot 1 (CCRC Code DK121806). A polysaccharide composition according to the invention is referred to as "Galahad" in Example 14. A component of the polysaccharide composition is a red material that can be precipitated by addition of ammonium sulfate and can thus be separated from the carbohydrate in the composition. This red material is referred to as "Galahad Red" in this example.
Figure 10:
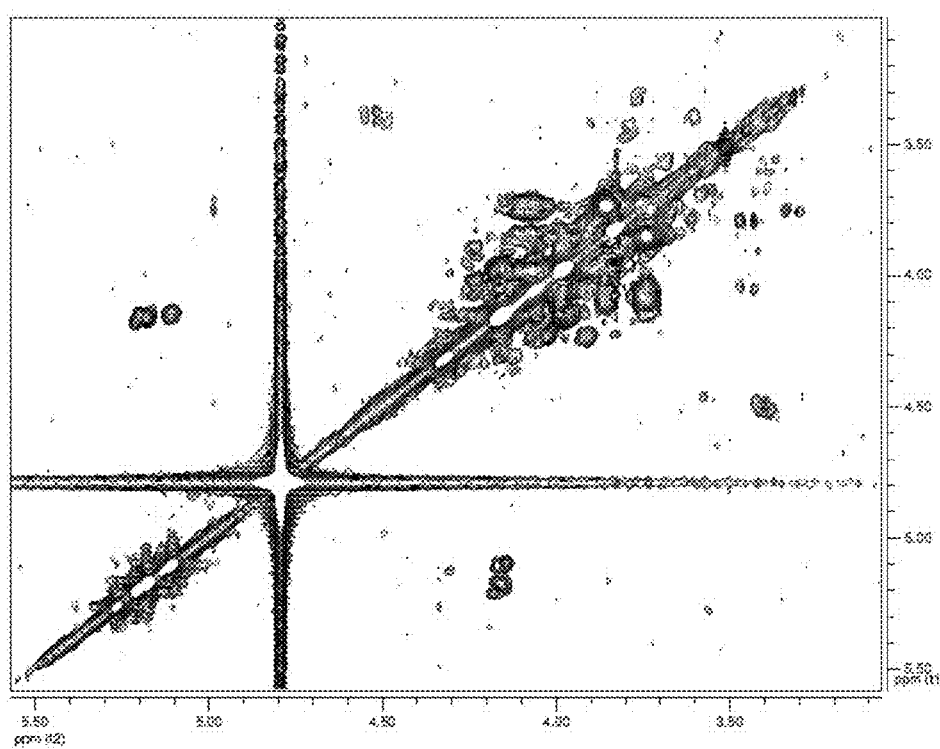
FIG. 10 shows the results of Example 14: Partial 2-D COSY NMR Spectrum of Galahad Lot 1 (CCRC Code DK121806).
Figure 11:
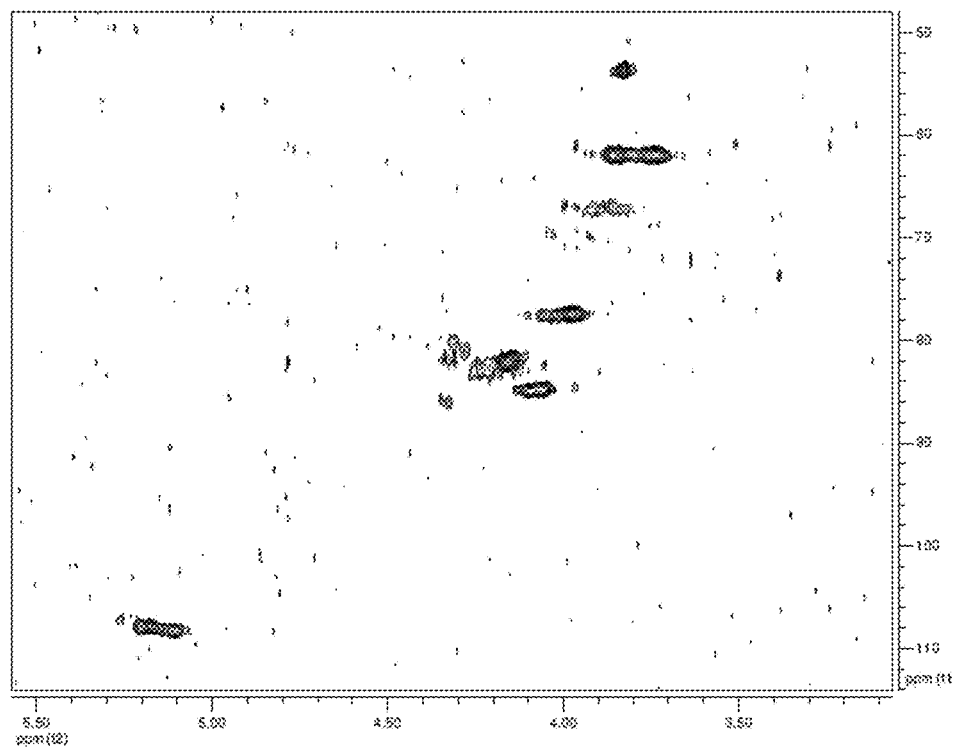
FIG. 11 shows the results of Example 14: 2-D HSQC NMR Spectrum of Galahad Lot 1 (CCRC Code DK121806).

The results of size exclusion chromatography are shown in FIG. 8. Approximate molecular weight of peaks was determined by comparison of retention time to that of known standards. Molecular weight of the 41 minute peak cannot be determined as it is in the included volume of the column.

TABLE D5

Size determination of Peaks

| | Retention Time (min) | Log M.W. | M.W. (kDa) |
|---|---|---|---|
| Dextran Stds. | 35.19 | 4.82 | 67 |
| | 33.92 | 5.22 | 167 |
| | 31.83 | 5.71 | 511 |
| | 27.91 | 6.15 | 1400 |
| Galahad 08:016 | 35.37 | 4.92 | 84 |

The red material within the sample was precipitated at the acidic pH used in the SEC. Thus, the molecular weight obtained by SEC likely refers to the arabinan.

NMR Spectroscopy

The 1-D proton NMR spectrum of Galahad showed a typical polysaccharide pattern with anomeric (5.2-4.5 ppm) and ring protons (4.3-3.5 ppm). Analysis of a set of 2-D spectra revealed several α-arabinofuranose spin systems. β-Galactopyranose is a minor components in the sample. A partial assignment is given in Table D7.

TABLE D7

NMR Chemical shift assignments of the arabinan.

| Residue | | Chemical Shift (ppm) | | | | | |
|---|---|---|---|---|---|---|---|
| | | 1 | 2 | 3 | 4 | 5 | 5' |
| t-α-Araf | $^1$H | 5.21 | 4.17 | 3.99 | 4.08 | 3.85 | 3.74 |
| | $^{13}$C | 108.0 | 82.0 | 77.5 | 84.8 | 61.8 | |
| t-α-Araf | $^1$H | 5.18 | 4.17 | 3.98 | n.d. | n.d. | n.d. |
| | $^{13}$C | 107.8 | 82.0 | 77.5 | n.d. | n.d. | |
| 5-α-Araf | $^1$H | 5.07 | 4.24 | 3.92 | 4.06 | 3.97 | 3.79 |
| | $^{13}$C | 108.2 | 82.0 | 77.5 | 82.0 | | |
| 3,5-α-Araf | $^1$H | 5.10 | 4.16 | 4.07 | 4.24 | 3.97 | 3.83 |
| | $^{13}$C | 108.2 | 82.0 | 82.7 | 82.9 | 67.2 | |
| 2,5-α-Araf | $^1$H | 5.27 | 4.24 | 4.06 | n.d. | 3.97 | 3.83 |
| | $^{13}$C | 107.3 | 86.2 | n.d. | n.d. | 67.2 | |
| 2,3,5-α-Araf | $^1$H | 5.14 | 4.32 | n.d. | n.d. | 3.97 | 3.83 |
| | $^{13}$C | 108.2 | 86.2 | n.d. | n.d. | 67.2 | |
| β-Galp | $^1$H | 4.52 | 3.39 | 3.56 | 3.69 | 3.76 | n.d. |

The 1-D spectrum also showed a broad peak around 7 ppm, indicating presence of an aromatic polymer (such as e.g. tannin). We attempted to remove this polymer by passage through a C18 column. It appeared that the fraction eluted with 5% acetic acid still contained the same relative amount of aromatic polymer, while the fraction eluted with water contained significantly less. It is not clear if the aromatic polymer is covalently attached to the polysaccharide or if the two components coelute from the column. It turned out that only a small portion of the sample was eluted from the column.

The NMR results confirmed the linkage analysis data. Terminal arabinofuranose is the main component in the spectra, indicating that the sample is a highly branched arabinan.

Dynamic Light Scattering

Figure 12:
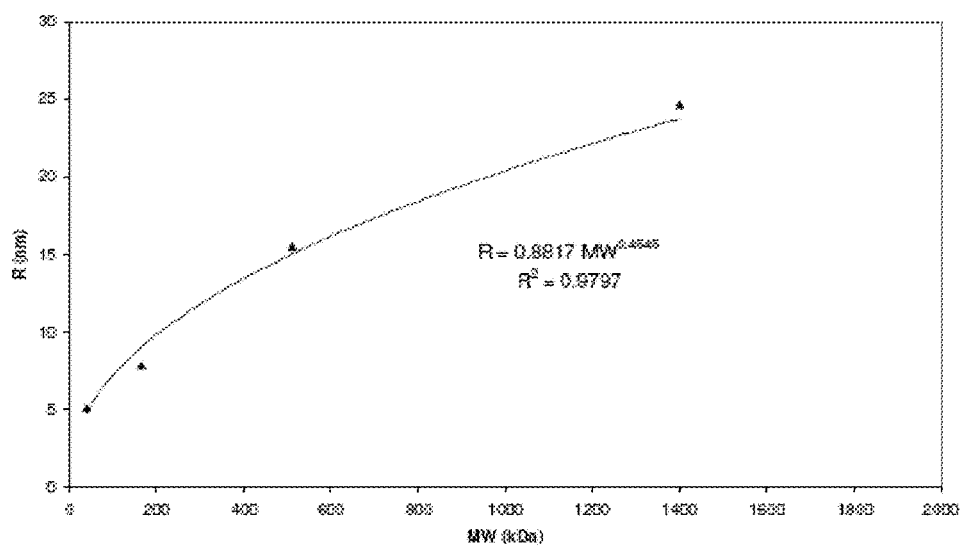
FIG. 12 shows the results of Example 14: Dextran standard curve.

To get an estimation of the size of the red material, which constitutes the bulk of the product was obtained through light scattering. The DLS software gave accurate molecular dimensions for the standards that were in agreement with the literature (http://www.dextran.net/dextran-physical-properties.html). The radius values of the standards were fitted to a power trendline in Excel (see FIG. 12), giving an R2 value of 0.9797, which indicates a good data fit. Both the raw Galahad sample and the ammonium sulfate precipitate each showed a major and a minor component. The minor component made up less than 5% of the mass in both samples. The measured radii of the two components in both samples, as well as their mass average molecular weights, polydispersity, and mass contribution are tabulated in Table 3.

TABLE D6

DLS results

| Sample | r (nm) | % polydispersity | MW (kDa) | % mass |
|---|---|---|---|---|
| Galahad | 6.1 | 13.0 | 68 | >95 |
| | 25.6 | 14.0 | 1,600 | <5 |
| AS ppt | 5.4 | 24.6 | 54 | >95 |
| | 28.5 | 21.6 | 2,200 | <5 |

The fact that the red material could be precipitated with ammonium sulfate led us to believe that the material might include a protein. Amino acid analysis, however, gave us only very low levels of the two amino acids, alanine and serine. Given these low levels of amino acid observed and the fact that most proteins are composed of more than 2 amino acids, Galahad Red is most likely composed of something other than protein.

This gives us a mass of around 68,000 for the most abundant component. We noted that Galahad Red could be precipitated by addition of ammonium sulfate and could be separated from the carbohydrate material.

Molecular Weight Determination Using SDOC PAGE of Galahad and DEAE Purification

We have performed an initial carbohydrate gel electrophoresis analysis to check for polysaccharides. This analysis can tell us whether the carbohydrate we have isolated by DEAE has a molecular weight consistent with what we observe with our SEC analysis. It also allows us to check for the presence of saccharides in other fractions. SDOC of Galahad fractions showed that Galahad is mainly made of high molecular weight polysaccharide.

High molecular weight saccharide was present in all fractions eluted from a DEAE column. The saccharide staining observed was consistent with the 84 kDa saccharide seen by SEC analysis.

We have concluded that the molecular weight determination by SEC, Dynamic Light Scattering and gel electrophoresis all agree and indicate a high molecular weight species about 80 kD.

Butanol HCl Iron Digestion

Color reaction in the presence of acidic iron solution is often used as a test for tannin. The Galahad Red ammonium sulfate precipitate and green tea both produced the dark red color which is taken as a positive for tannin, suggesting that Galahad Red is a high molecular weight tannin. Later experimenst led us to conclude that although the material may be a proanthocyanidin, it is not a tannin.

Extraction of Low Molecular Weight Proanthocyanidins

Figure 13:
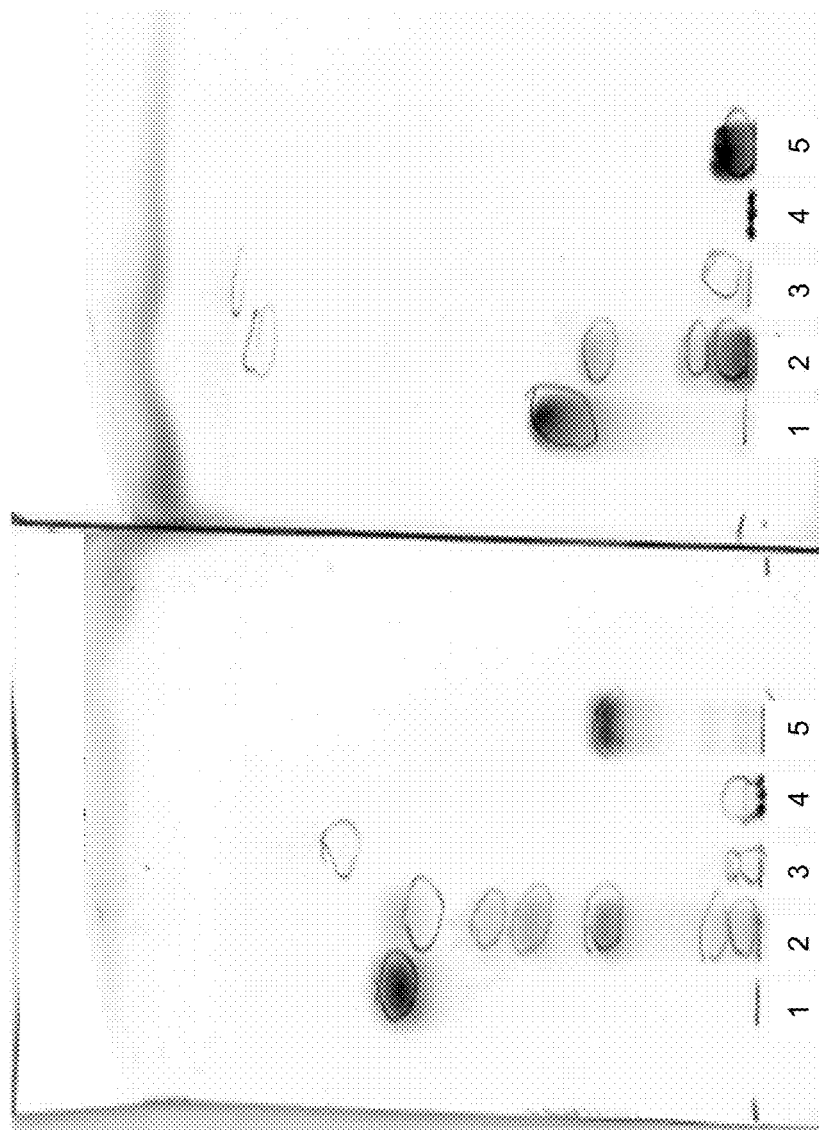
FIG. 13 shows the results of Example 14: TLC Analysis of Galahad and Green Tea Extracts as well as Galahad butanolic HCl iron digest. Lane 1—Catechin 15 ug; Lane 2—Green Tea Extract 20 ug; Lane 3—Galahad Ethyl acetate Extract, 40 ug; Lane 4—Galahad butanolic HCl iron digest; Lane 5—Proanthocyanidin B1 (dimeric proanthocyanidin), 20 ug.

The results of this study are shown in FIG. 13.

MALDI TOF Mass spectrometry was used to analyze both intact and extracted Galahad as well as dowex desalted butanolic HCL iron digest.

TABLE D7

MALDITOF results of intact and extracted Galahad as well as dowex desalted butanolic HCL iron digest

| Sample | Predicted Ion m/z | Observed Ions |
|---|---|---|
| Catechin | 291 | 291 |
| Procyanidin B1 | 578, 601 (M + Na) | 601 |
| Galahad Extract | | 291, 295, 301, 303, 313, 317, 339, 361, 381, 409, 413, 537, 545, 676, 699 |
| Green Tea Extract | | 528 |
| Galahad Iron Digest | | 215, 231, 245, 317, 361, 375 |

Extraction of Galahad with ethyl acetate did not give enough material to analyze by TLC. Acidic iron digestion suggested the presence of tannin in the ammonium sulfate precipitate. TLC shows both monomeric and dimeric cyanidins in the Green Tea extract.

UV/Visible Spectrophotometry

Spectra of Galahad compositions were compared to data obtained for known anthocyanidins (Freitas and Mateus Environ. Chem. Letters (2006) 4:175-183).

TABLE D8

UV/Visible Spectrophotometry

| Compound | Abs Max | Abs Max Glycosylated |
|---|---|---|
| Delphinidin | 546 | 541 |
| Petunidin | 543 | 540 |
| Malvidin | 542 | 538 |
| Cyanidin | 535 | 530 |
| Peonidin | 532 | 528 |
| Pelargonidin | 520 | 516 |
| Galahad A.S. ppt | 468 | |
| Galahad DEAE | 419 | (shoulder at 500) |
| Galahad DEAE post IO$_4^-$ | 370 | (no decrease on low side) |

CHN Analysis

CHN analysis shows a high level of carbon relative to hydrogen in the sample and little nitrogen. This is consistent with an anthocyanidin or proanthocyanidin but inconsistent with protein, which would be expected to have a high level of nitrogen.

TABLE D9

CHN analysis of the DEAE purified Galahad sample

| Sample | % C | % H | % N |
|---|---|---|---|
| Galahad DEAE | 23.281 | 3.929 | 0.101 |

Protein and Composition Analysis of Galahad Ammonium Sulfate Precipitate

The results of protein quantitation are shown in Table 10.

TABLE D10

Protein Quantitation

| | Absorbance | ug Protein | Average Concentration (mg/ml) | Std Dev. |
|---|---|---|---|---|
| Galahad Start | 0.721 | 1.839416058 | 18.03 | 0.80 |
| | 0.707 | 1.711678832 | | |
| | 0.723 | 1.857664234 | | |
| A.S. Ppt. (10 mg/ml) | 0.903 | 3.989484753 | 3.78 | 0.30 |
| | 0.85 | 3.432176656 | | |
| | 0.896 | 3.915878023 | | |

Note that both the Starting material and Ammonium sulfate precipitate (A.S. Ppt.) were originally assayed in a separate assay. Absorbance of starting material was above the level of the standard curve (BSA) and had to be diluted prior to reanalysis. 1 μl of a 10 mg/ml solution of ammonium sulfate precipitate was assayed and 10 μl of starting material diluted 1:100 was also assayed.

The results of glycosyl composition analysis are given in Table D11 and are explained below. Threitol was added to the sample before derivatization as an internal standard (10 micrograms to each sample). The sums of the area percentages shown here represent a sum of the values truncated to the first decimal place. There is thus a small rounding error associated with the sum of the percentages which is why they may not sum to 100.0%. Values under 2 ug or over 200 ug are given as approximations only due to the lack of assay linearity in these regions.

TABLE D11

Glycosyl Composition Analysis of A.S. Ppt.

| Sample Moiety Galahad 08:016 A.S. Ppt | Mass (μg) | Mole %[1] |
|---|---|---|
| Rhamnose (Rha) | 0.9 | 2.1 |
| Fucose (Fuc) | n.d. | n.d. |
| Arabinose (Ara) | 31.6 | 77.8 |
| Glucuronic Acid (GlcUA) | n.d. | n.d. |
| Galacturonic acid (GalUA) | 4.7 | 8.9 |
| Mannose (Man) | 0.5 | 1.0 |
| Galactose (Gal) | 4.1 | 8.4 |
| Glucose (Glc) | 0.9 | 1.8 |
| N Acetyl Galactosamine (GalNAc) | n.d. | n.d. |
| N Acetyl Glucosamine (GlcNAc) | n.d. | n.d. |
| Heptose (Hep) | n.d. | n.d. |
| 3 Deoxy-2-manno-2 Octulsonic acid (KDO) | n.d. | n.d. |
| 3OH C16 FA | n.d. | n.d. |
| C16 FA | n.d. | n.d. |
| C18 FA | n.d. | n.d. |
| Sum | 43 | 100 |

[1]Values are expressed as mole percent of total carbohydrate. The total % carbohydrate is calculated to be 6%.
n.d. = none detected Starting material is shown by this assay to have a very high concentration of protein. One caveat to this is that we are using a dye binding assay to measure protein and hydrophobic compounds can interfere with the assay, giving falsely high protein readings. Red color was noted to precipitate with ammonium sulfate. The ammonium sulfate precipitate appears to be approximately 40% protein and 6% carbohydrate. The sugars observed in the precipitate are largely the same as the starting material with only xylose absent (xylose was present at about 2 mol % in the starting material). SDS PAGE was attempted to identify proteins in this sample but low quantities of the red material interfered with the silver stain which we used to visualize the gel. Oddly, most of the red material aggregated at the top of the gel. During methanolysis (used for HFB composition), the red material became much more soluble and could be seen to migrate on a silica gel TLC plate.

TLC

Figure 14:
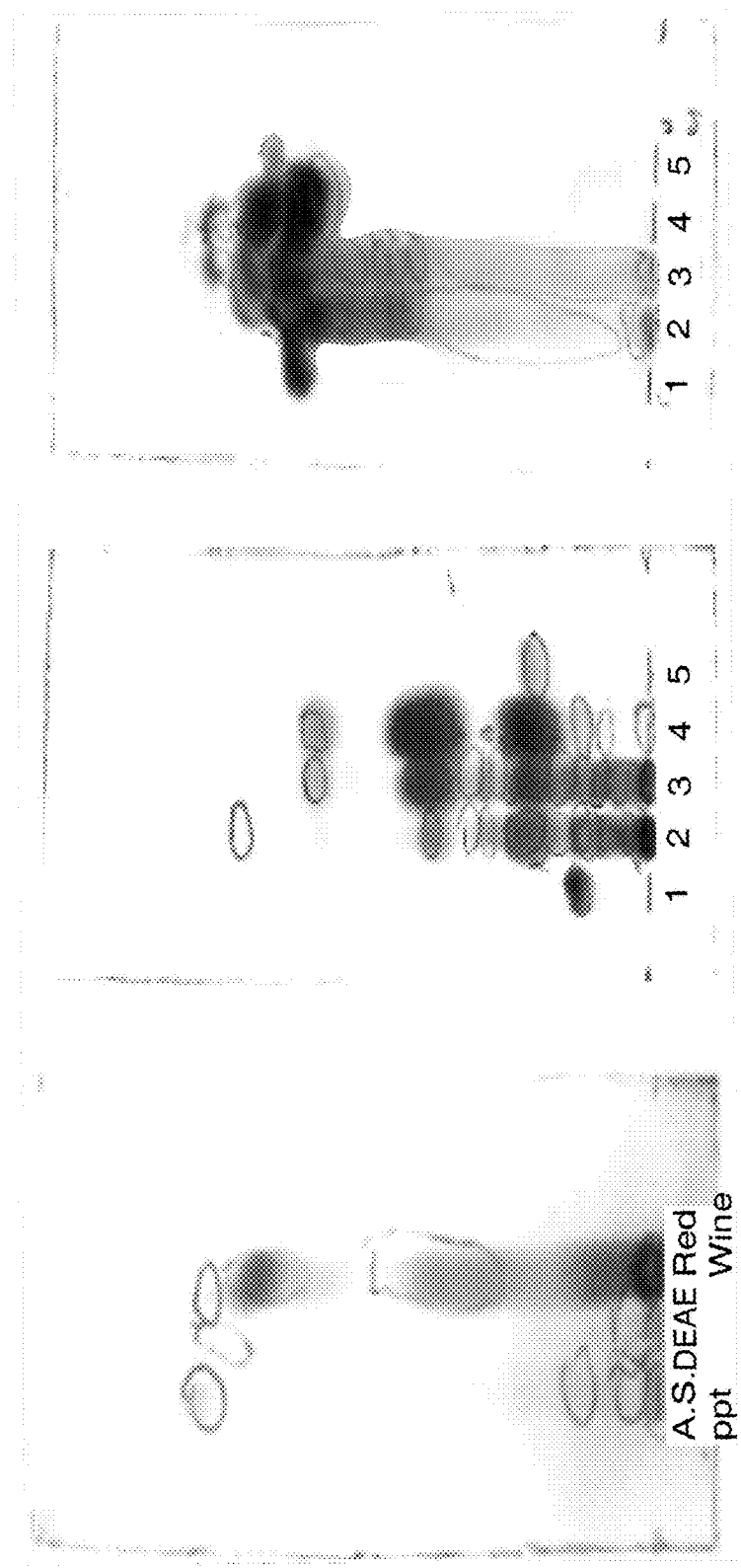
FIG. 14 shows the results o Example 14: Analysis of Intact Galahad and Phloroglucinol Products. TLC Plate at left: the ammonium sulfate precipitate and DEAE purified material (lanes 1 and 2 respectively) in comparison to 2 μl of Carlo Rossi burgundy which has a variety of anthocyanins and proanthocyanins. Considerable staining is observed at the origin of both Galahad lanes, consistent with a high molecular weight polymer. Middle and right TLC plates: oroglucinol reaction products. Lane 1—Catechin, 10 μg; Lane 2—Carlo Rossi Burgundy, Lane 3—Ammonium Sulfate precipitate; Lane 4 DEAE Purified Galahad; Lane 5 Phloroglucinol, 4 ug. Middle plate is developed in chloroform:methanol 9:1 to look for anthocyanidin adducts. Right plate is developed in chloroform:methanol: aqueous KCl 5:4:1 to look for partial degradation products. Note the series of slow eluting bands in the right plate seen in A. S. ppt and Carlo Rossi Burgundy. These may be partial breakdown products.

The results of TLC analysis of intact Galahad and phloroglucinol products is shown in FIG. 14.

The results of ultrafiltration of A.S. Ppt. through 2 filters is shown in Table D12.

TABLE D12

Ultrafiltration of A.S. Ppt. through 2 filters.

| Filtrate | Color |
|---|---|
| 100 kD | Pink |
| 10 kD | Clear |

Figure 15:
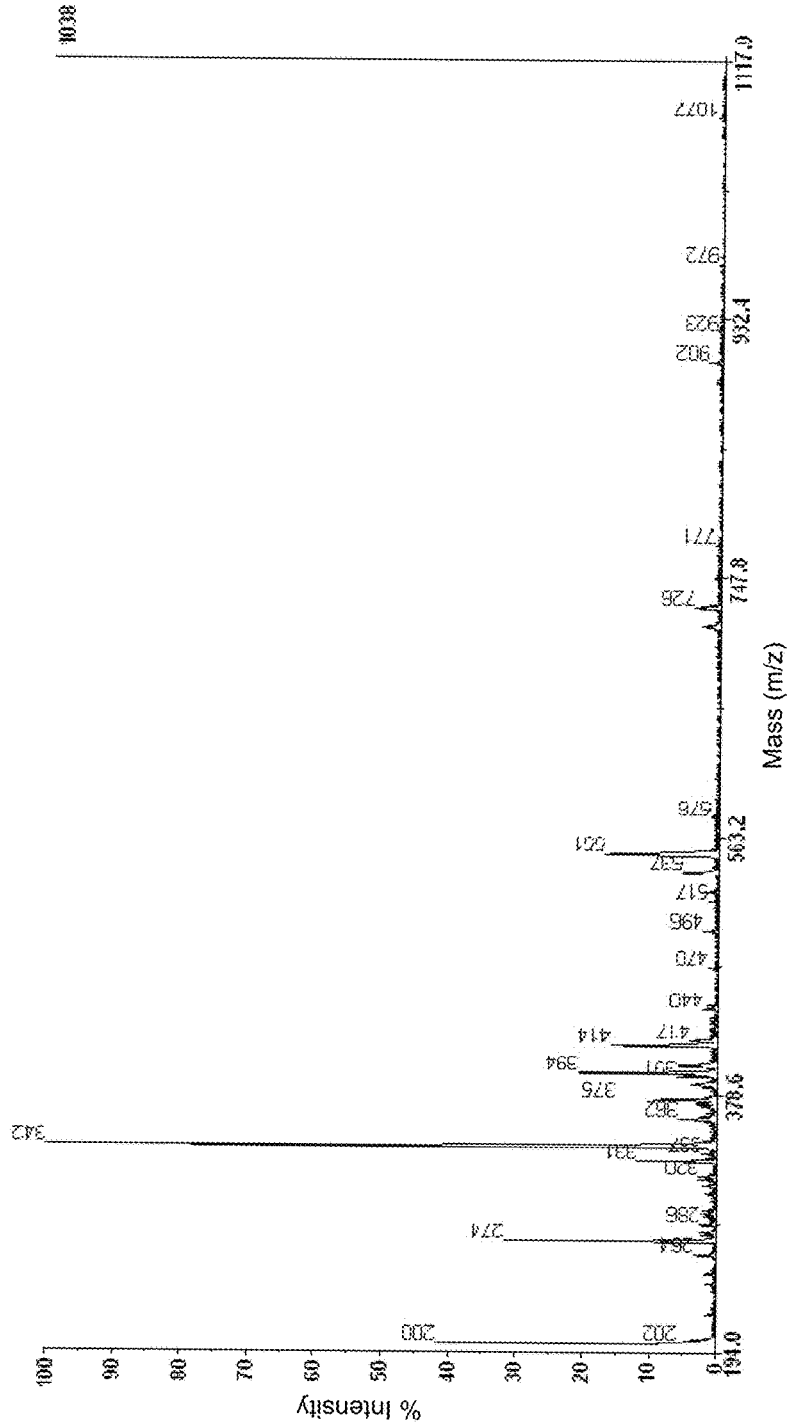
FIG. 15 shows the results of Example 14: MALDI TOF Analysis of Iatrobead Pool 2 from Phloroglucinolysis Reaction 2. Mass at m/z 342 is consistent with the sodium adduct of peonidin or petunidin.

Mild phloroglucinolysis was ineffective in rendering the molecule into its component anthocyanidin monomers, which suggested that it fell largely within the class of "condensed tannins" which are largely unanalyzed. TLC on intact Galahad Red shows substantial material at the origin. This, combined with the fact that ultrafiltration confirms the material to have a molecular weight over 10 kD mean that LC on silica of the intact material may well prove impossible. Our efforts to purify material on butyl sepharose have fared little better with even extremely hydrophobic solvents failing to elute all colored material. Our efforts at breaking up the molecule are meeting with more success. Phloroglucinolysis of the DEAE purified material shows all major bands to be present in red wine meaning that we have no unusual anthocyanin adducts in the reaction products. Phloroglucinolysis of the ammonium sulfate precipitate shows considerably more complexity with a number of potential partial phloroglucinolysis adducts present. MALDI MS of Pool2 from the second phloroglucinolysis shows an ion with m/z 342, consistent with the molecular mass of the sodium adduct of either petunidin or peonidin (FIG. 15). As this is not a phloroglucinol adduct, it may well be that this residue is at one end of the polymer.

Amino Acid Analysis

Amino acid analysis indicated low levels of alanine and serine. The low levels of amino acid observed and the fact that most proteins are composed of more than 2 amino acids indicated that Galahad Red is composed of something other than protein.

Biological Activity of Separated Material

The majority of the biological activity resided in the ammonium sulfate precipitate; the purified carbohydrate had little activity by itself. The results suggest that the combination of carbohydrate portion and the Galahad Red material to be biologically active.

TABLE D13

Biological Activity of Separated Components

| | CPE, Assay $EC_{50}$ | | Direct Inactivation | Neutral Red Uptake |
|---|---|---|---|---|
| Component | HSV-1 | HSV-2 | $EC_{50}$ | $CC_{50}$ |
| 1 | * 12.9 | * 6.1 | 13 ± 0.5 | **>4 |
| 2 | 92 | 48.2 | 51.5 ± 17 | >100 |
| 3 | >100 | >100 | >100 ± 0 | >100 |
| 4 | >100 | >100 | >100 ± 0 | >100 |

TABLE D13-continued

Biological Activity of Separated Components

| | CPE, Assay $EC_{50}$ | | Direct Inactivation | Neutral Red Uptake |
|---|---|---|---|---|
| Component | HSV-1 | HSV-2 | $EC_{50}$ | $CC_{50}$ |
| $^A$5 | 0.05 | 0.01 | **0.2 | >0.4 |
| ACV | 1.4 | 1.8 | NA | >100 |
| IGg | NA | | 0.3 ± 0.3 | NA |

Components:
1. Ammonium sulfate pellet (SS101008a)
2. Ammonium sulfate supernatant (SS101008b)
3. DEAE Load (SS101008c)
4. DEAE Eluate (SS101008d) (resupply)
5. Parent Compound (Galahad)
* Drug color at 100 µg/ml in CPE
**Drug color at 100 µg/ml and 20 µg/ml.
All Values are in µg/ml except #5 is % solution that is approximately 10 mg/ml
$^A$Toxicity in the direct inactivation assay for #5 $CC_{50}$ is 5.5%.
Galahad is %/ml for direct inactivation results and has an error of about 0.3

Given the color of the material and the fact that it did not seem to be composed of protein, nucleic acid, or lipid, and had only low levels of carbohydrate, we consider that the material might be a polymeric proanthocyanidin or tannin. We calculate that a polymer of the size we find in light scattering should have around 200 monomers.

A classic test for tannin, using protein precipitation of BSA as a marker, was performed. Though our Gallo Burgundy standard precipitated the protein nicely, Galahad demonstrated no such precipitation ability. This indicates that although the material may be a proanthocyanidin, it is not be a tannin.

TABLE D14

Results of Tannin Test

| | Precipitation with | | | |
|---|---|---|---|---|
| Sample | Low pH | Neutral pH | Low pH with BSA | Neutral pH with BSA |
| Galahad | + | − | + | − |
| Carlo Rossi Burgundy | − | − | + | + |

Phloroglucinolysis

Figure 16:
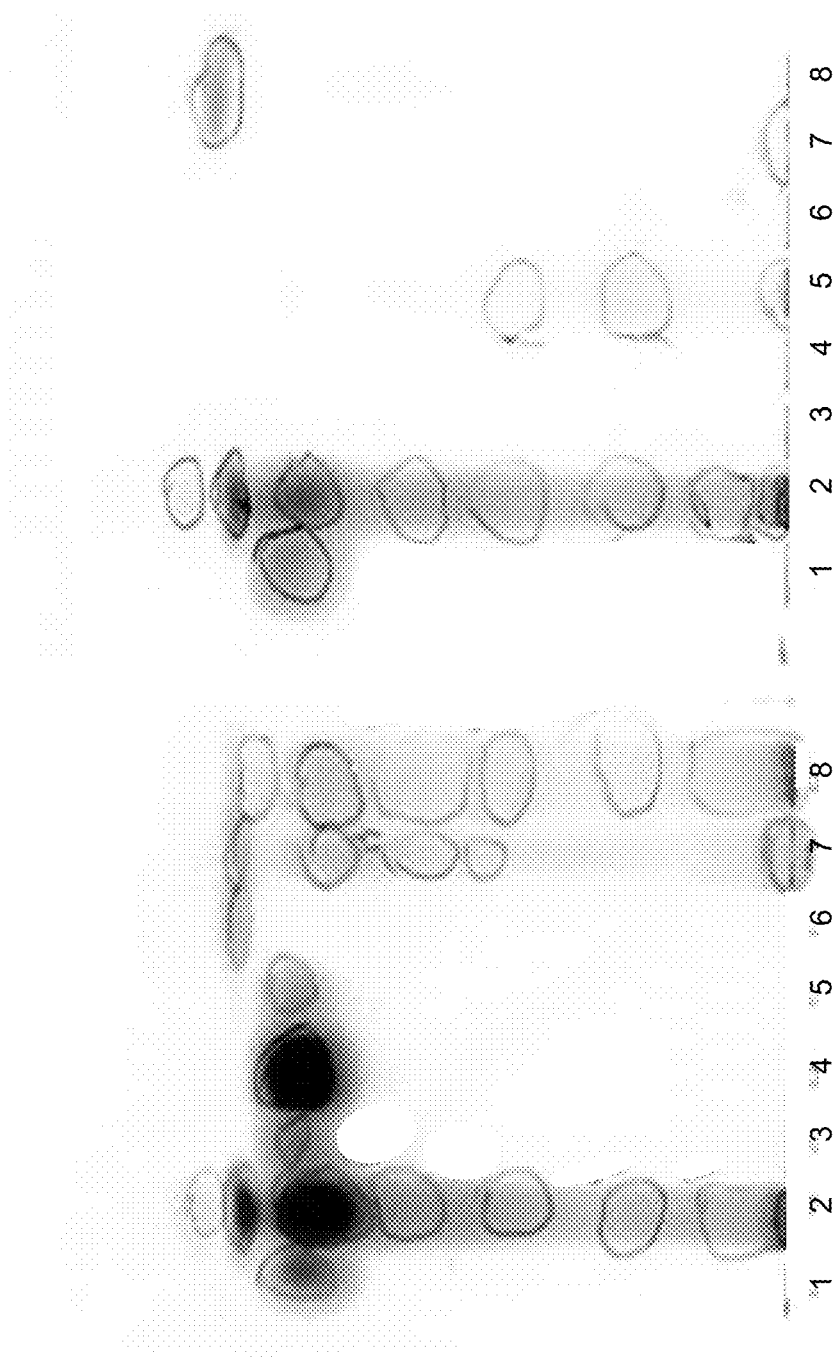
FIG. 16 shows the results of Example 14: TLC of Phloroglucinolysis Reaction Mix and Fractions from C18 Column. Phloroglucinolysis of a batch of Galahad Red produced an array of compounds as can be seen in lane 2 of each TLC. Lane 1 of each TLC corresponds to phloroglucinol, which is eluted in the load and 5% acetonitrile wash of the column, as shown in lanes 3, 4, and 5 of the TLC on the left. Methylated phloroglucinol elutes in the 15% and early 100% acetonitrile washes (lane 8 right plate and lane 7 of left plate) while most of the compounds produced on phloroglucinolysis elute with 100% acetonitrile (lanes 7 and 8 left plate). Benzene isopropanol elutes a strongly yellow band (lane 5 right plate) while addition of TFA to this solvent elutes a red band that remains at the origin (lane 7, right plate). Circled bands are visible without stain. Letters indicate color; P for pink, Y for yellow and B for brown.

The results of TLC of a phloroglucinolysis reaction mix and fractions from a C18 Column are shown in FIG. 16.

Figure 17:
FIG. 17 shows the results of Example 14: TLC of Silica Gel Purification of Acetonitrile Wash from C18. Acetonitrile eluate 2 from C18 chromatography was purified by preparative TLC. Shown are the reaction mix (lane 1) followed by the 7 pools (numbered). Circled bands are visible without stain and labeled as in FIG. 16.
Figure 18:
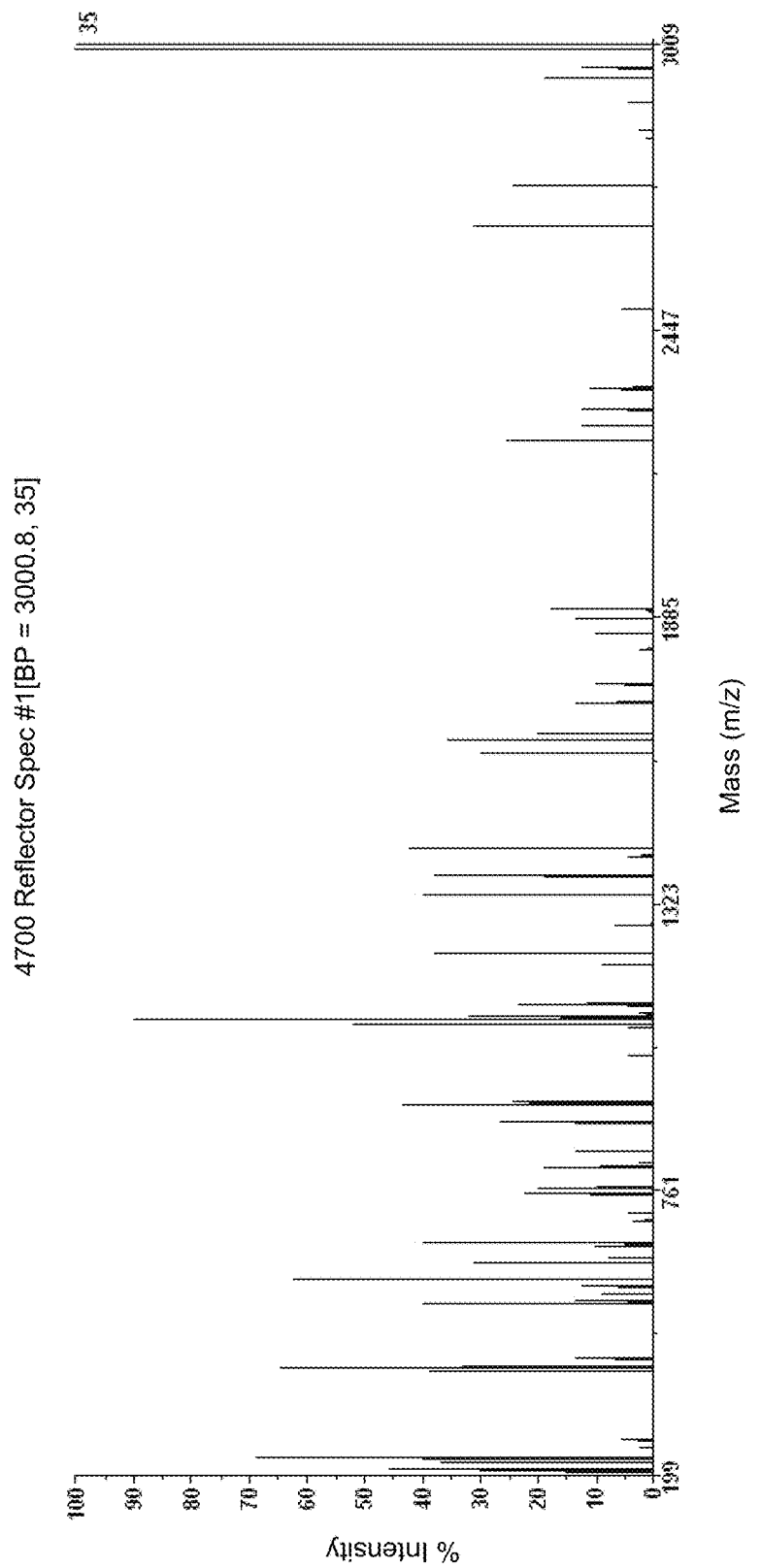
FIG. 18 shows the MALDI/MS results of Example 14: Silica Pool 1—Positive Mode.
Figure 19:
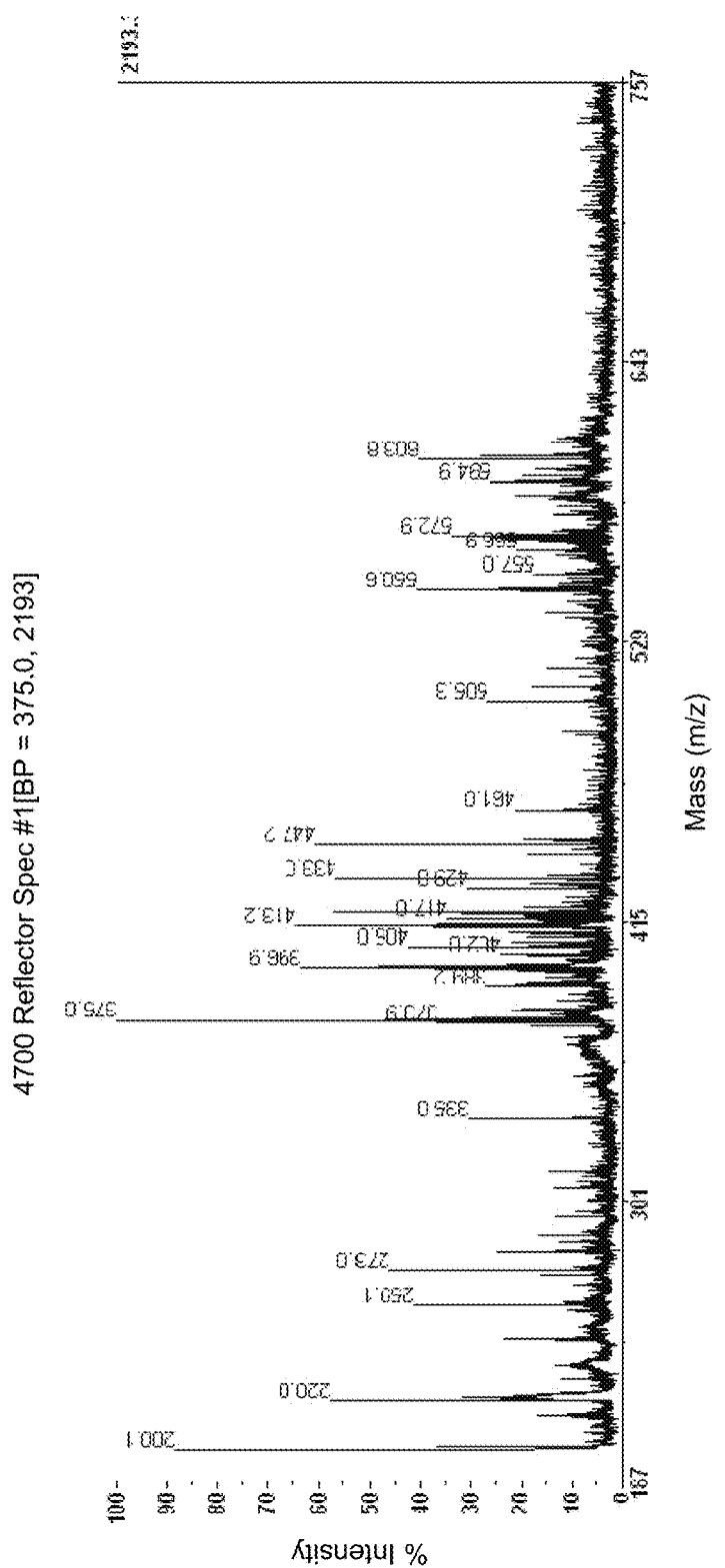
FIG. 19 shows the MALDI/MS results of Example 14: Silica Pool 2—Positive Mode.
Figure 20:
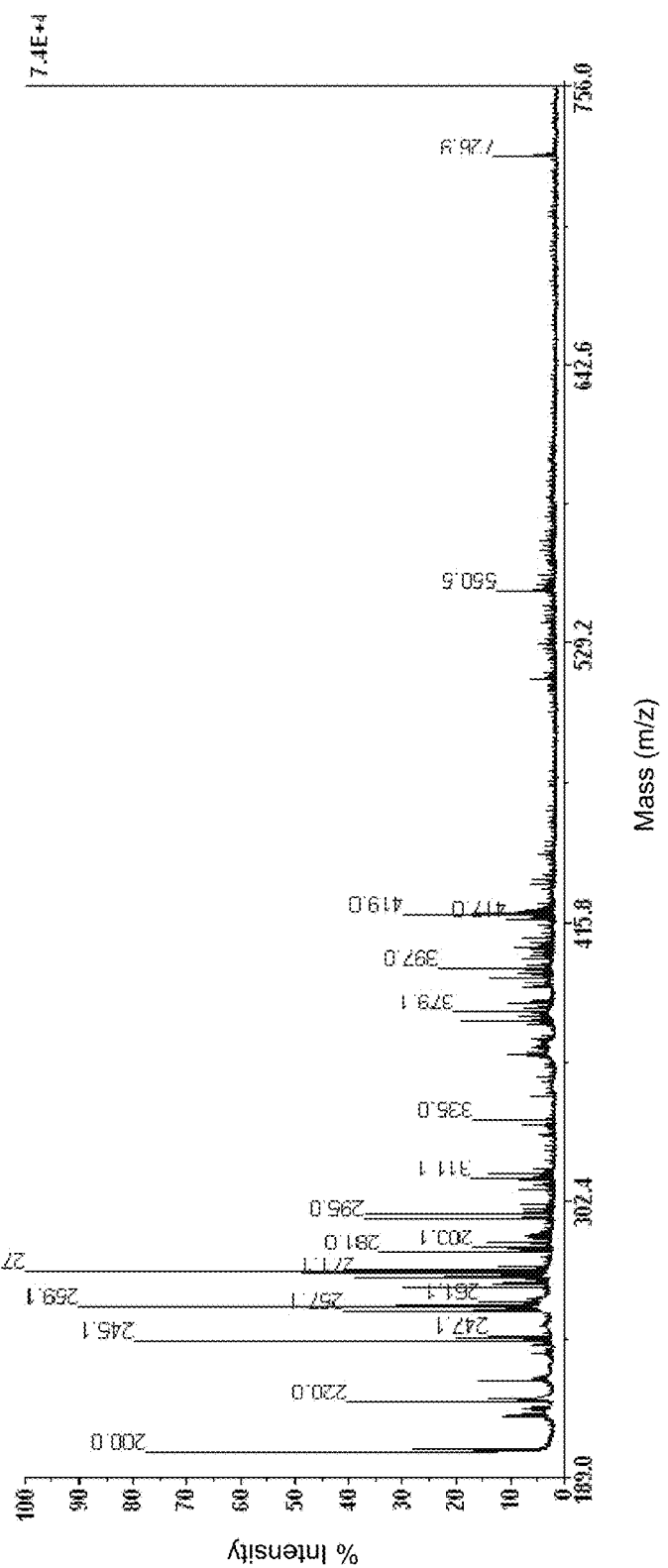
FIG. 20 shows the MALDI/MS results of Example 14: Silica Pool 3—Positive Mode.
Figure 21:
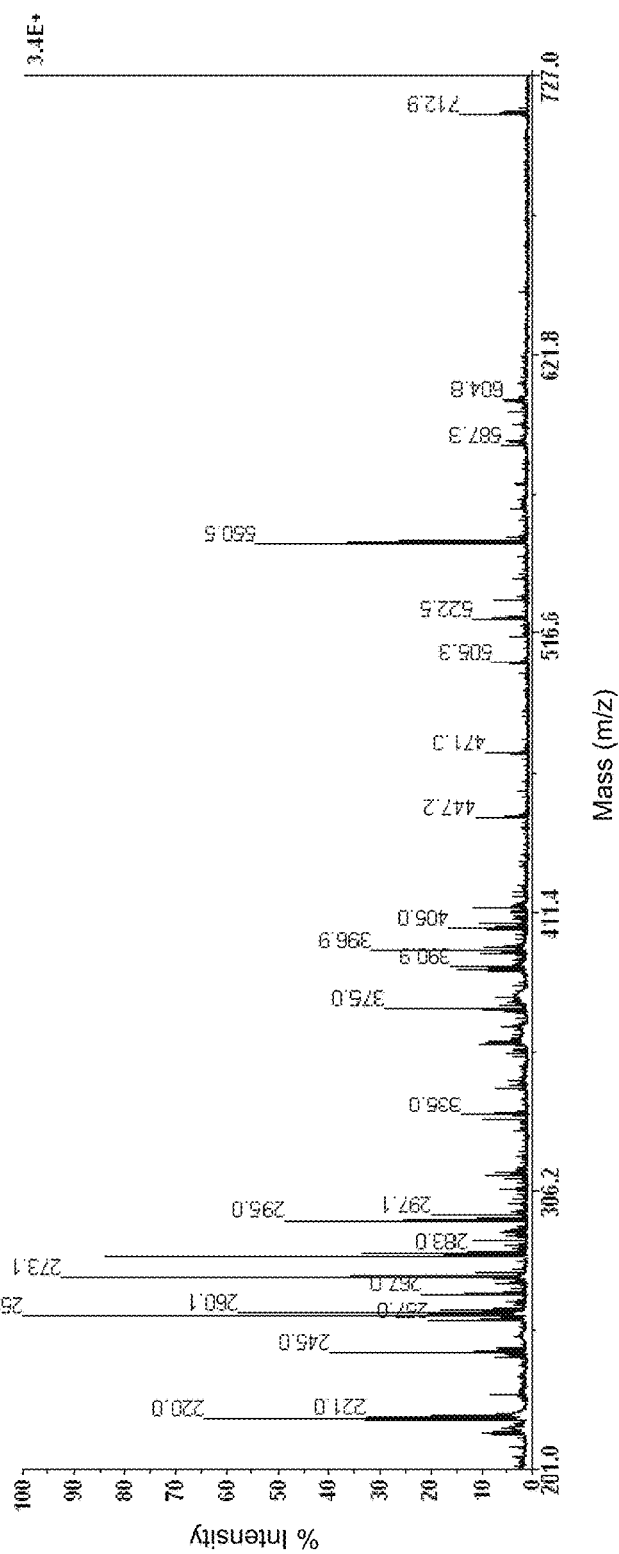
FIG. 21 shows the MALDI/MS results of Example 14: Silica Pool 4—Positive Mode.
Figure 22:
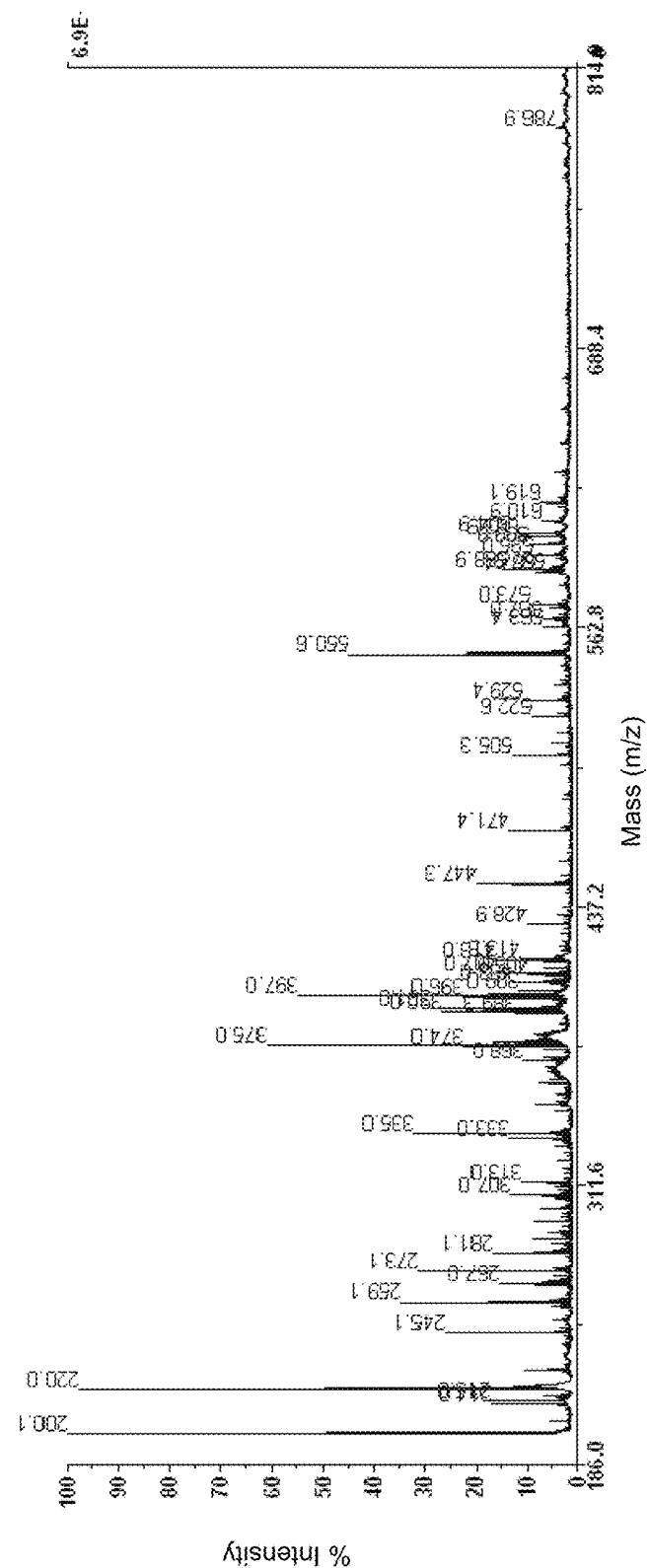
FIG. 22 shows the MALDI/MS results of Example 14: Silica Pool 6—Positive Mode.
Figure 23:
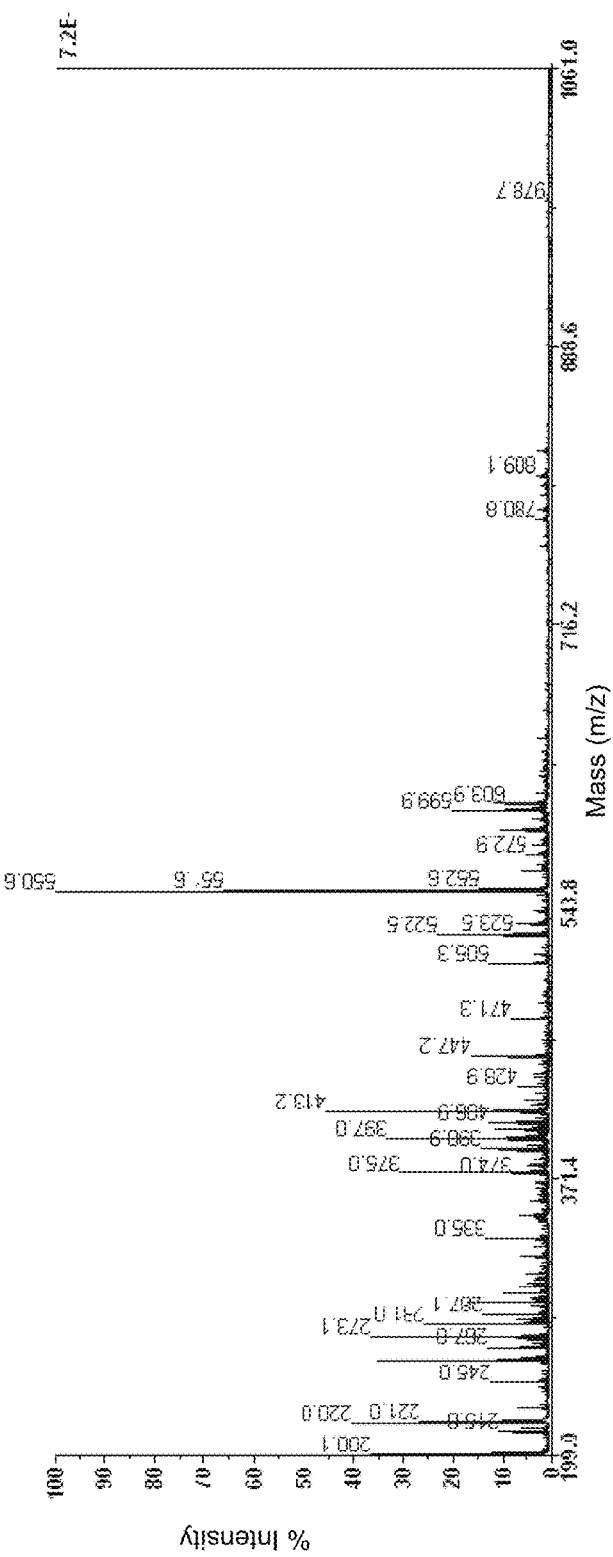
FIG. 23 shows the MALDI/MS results of Example 14: Silica Pool 7—Positive Mode.
Figure 24:
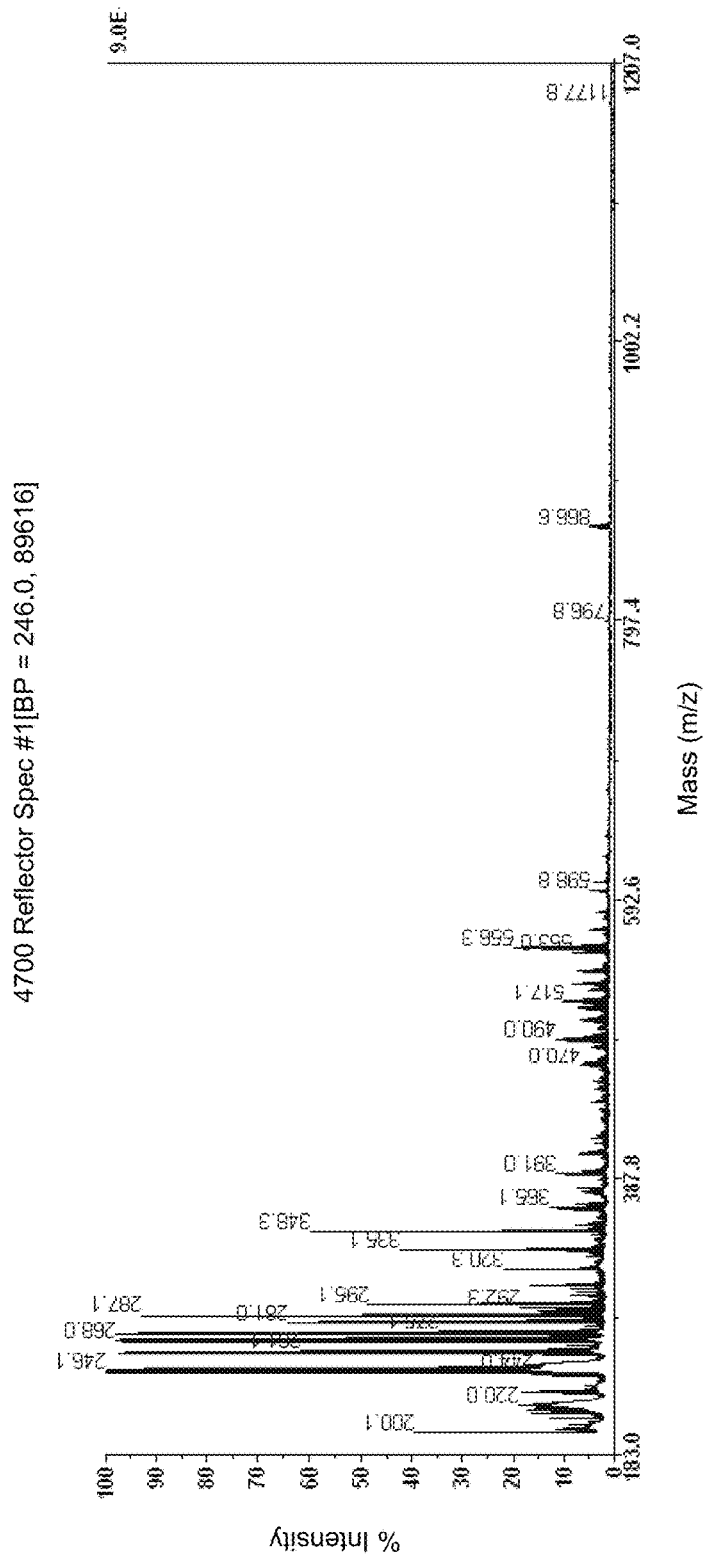
FIG. 24 shows the MALDI/MS results of Example 14: Benzene Isopropanol Eluate—Positive Mode.
Figure 25:
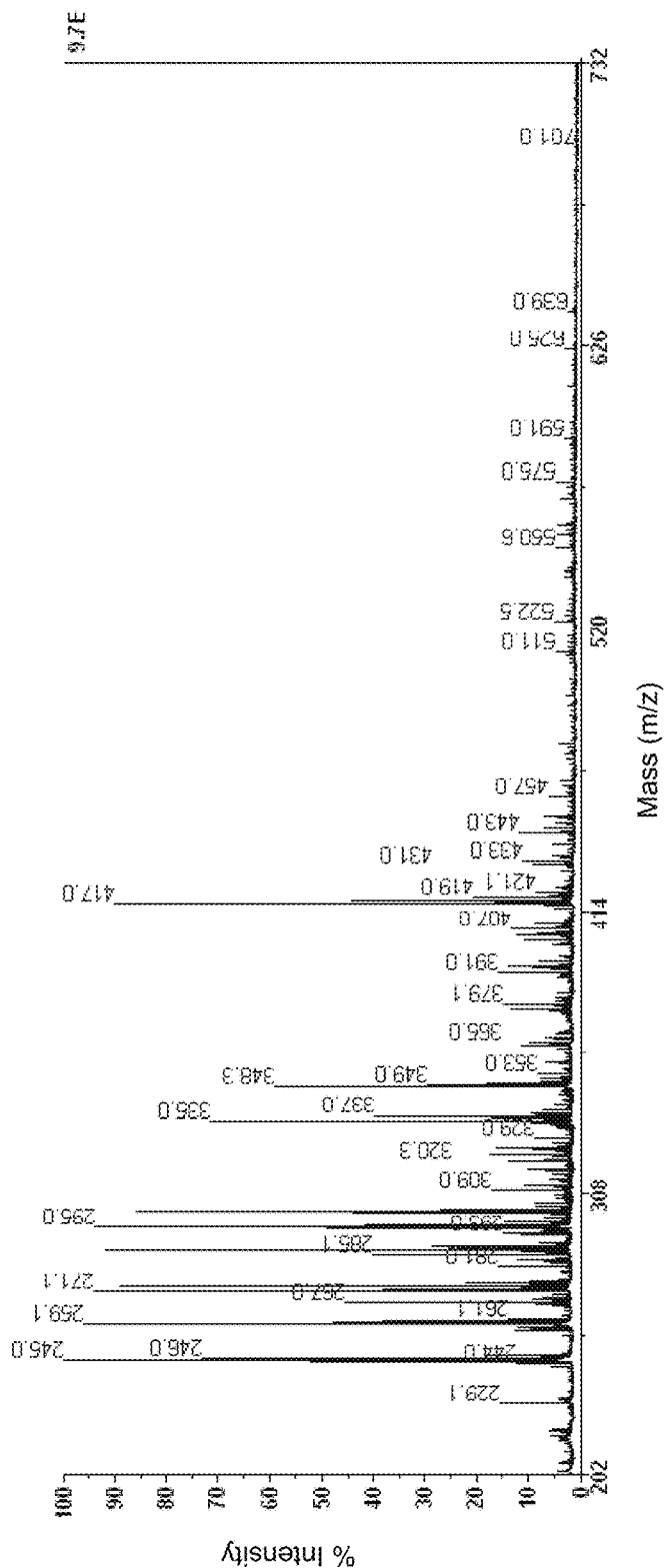
FIG. 25 shows the MALDI/MS results of Example 14: Benzene Isopropanol TFA—Positive Mode.
Figure 26:
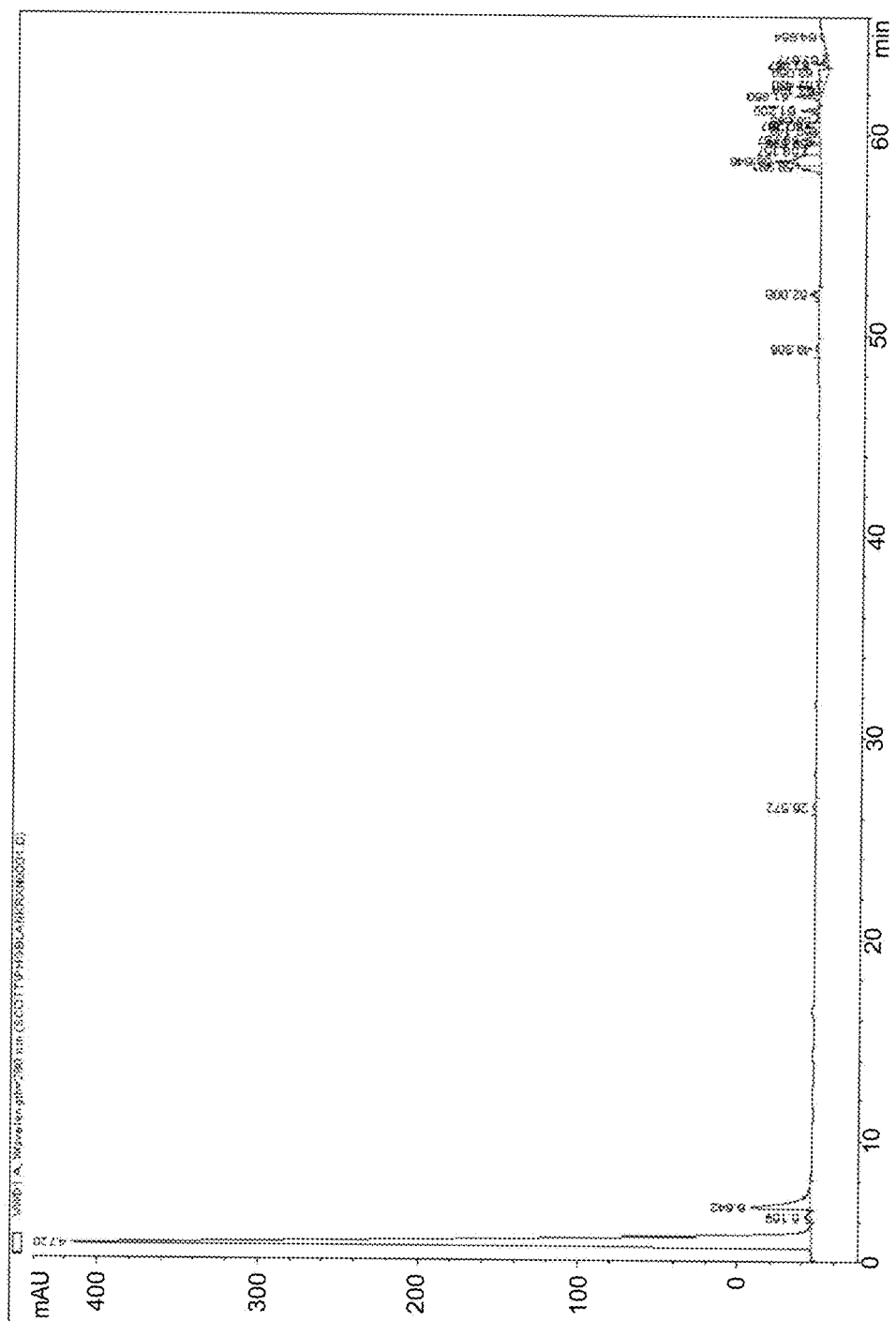
FIG. 26 shows the HPLC results of Example 14: Phloroglucinolysis Blank Reaction.
Figure 27:
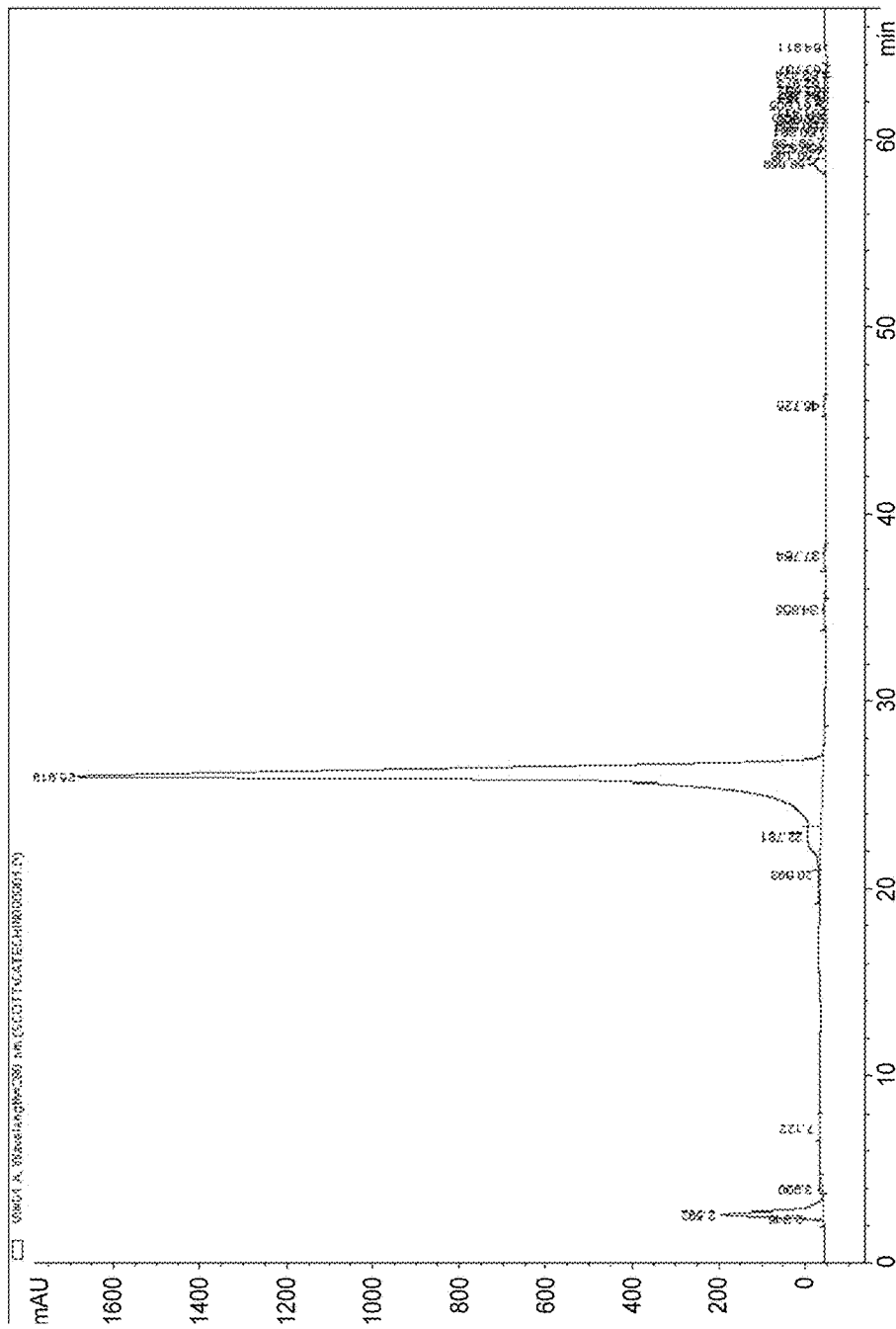
FIG. 27 shows the HPLC results of Example 14: Catechin Standard.
Figure 28:
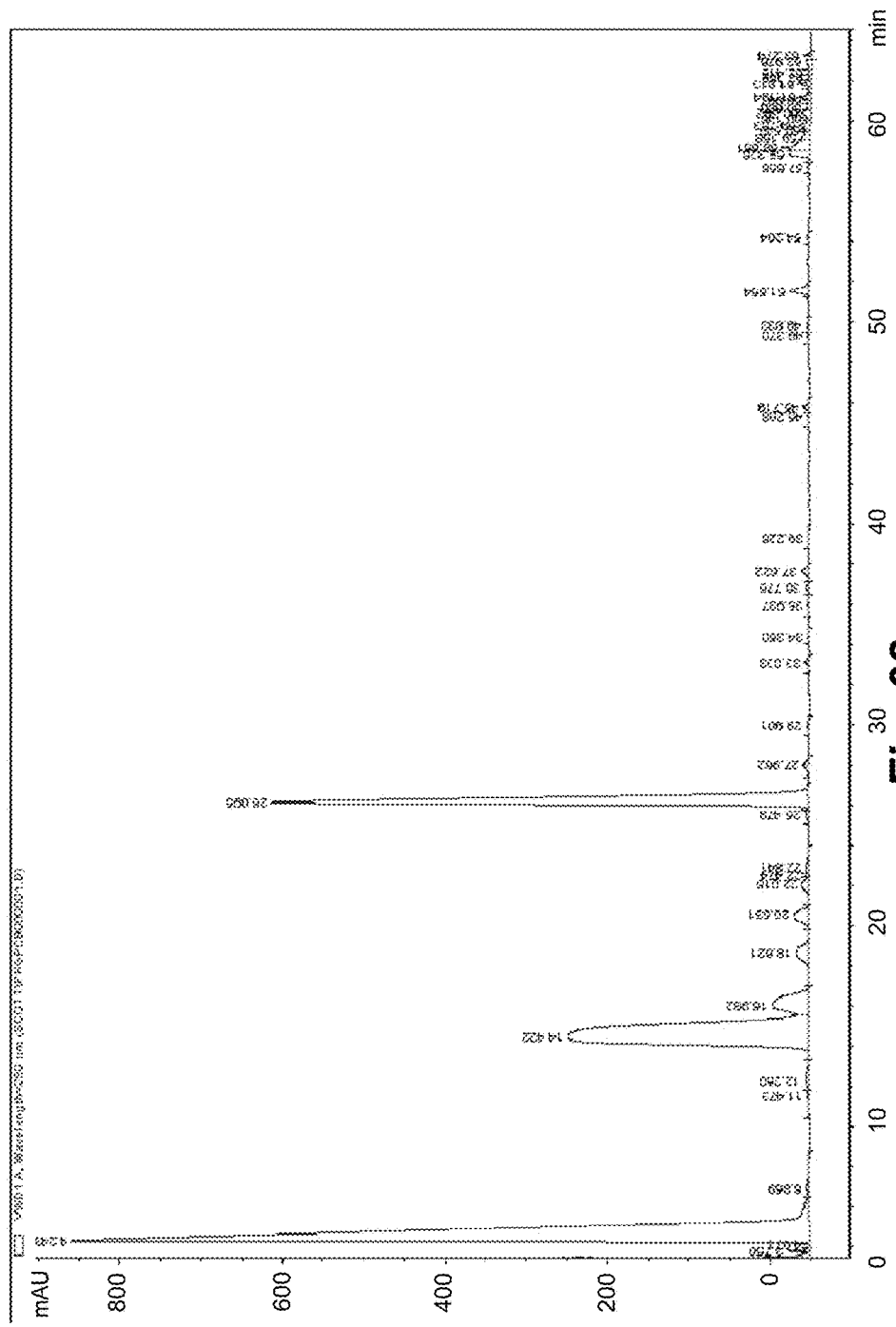
FIG. 28 shows the HPLC results of Example 14: Proanthocyanidin B1—Note that injection volume was 200 ul of 20% methanol, accounting for the peak shape of the catechin-phloroglucinol peak at 14.4 min.
Figure 29:
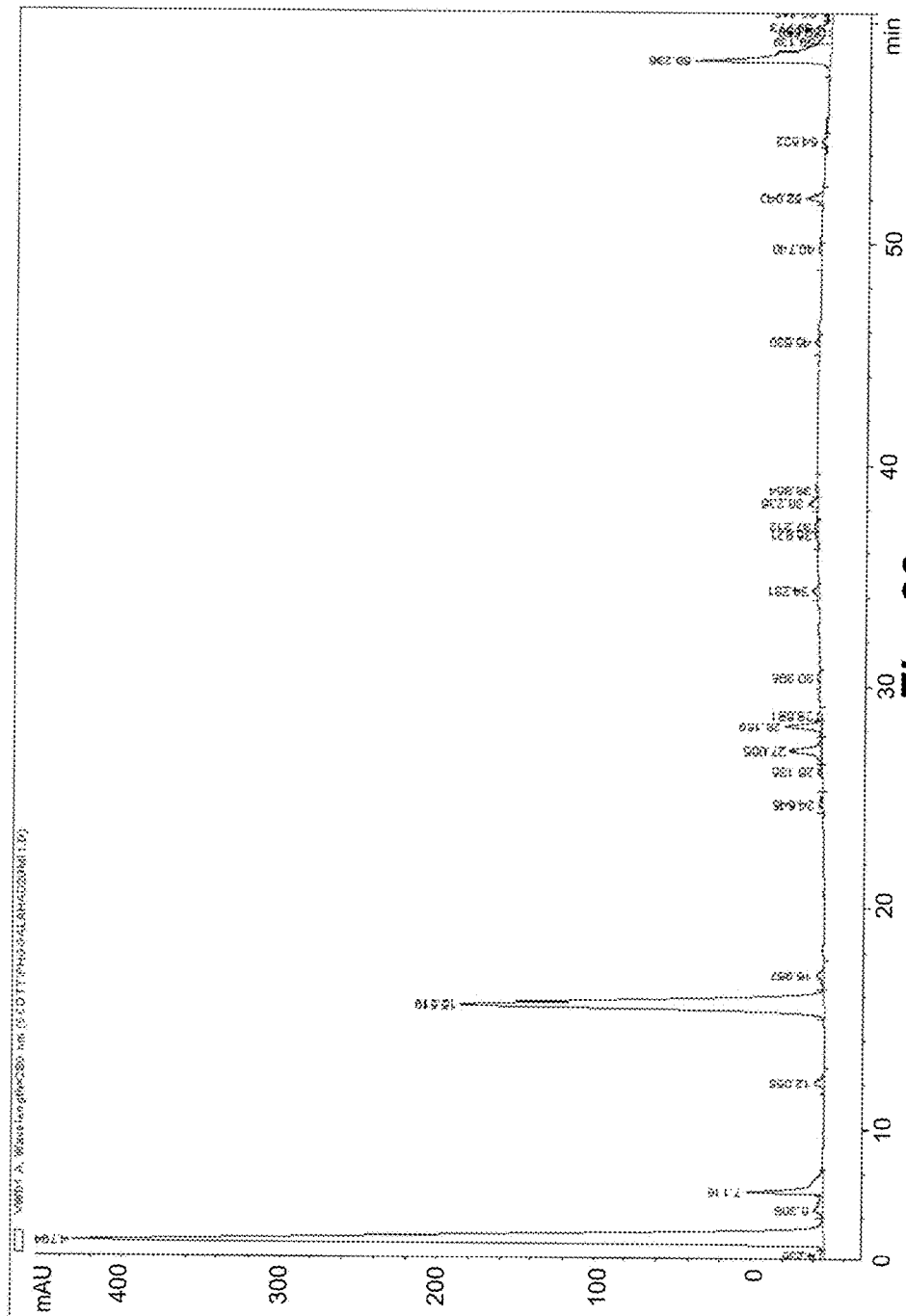
FIG. 29 shows the HPLC results of Example 14: Galahad 20 min reaction.
Figure 30:
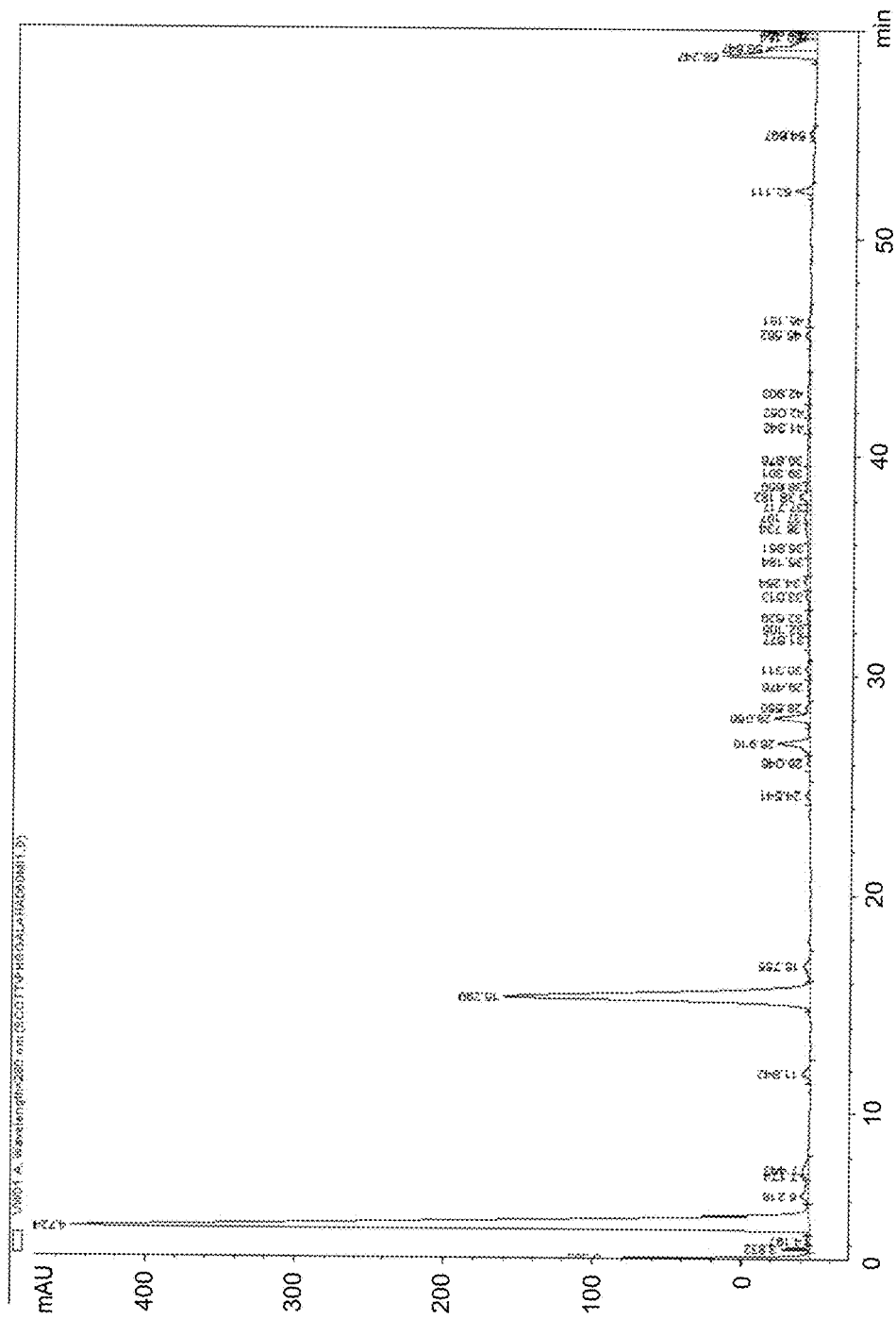
FIG. 30 shows the HPLC results of Example 14: Galahad 60 Min Reaction.
Figure 31:
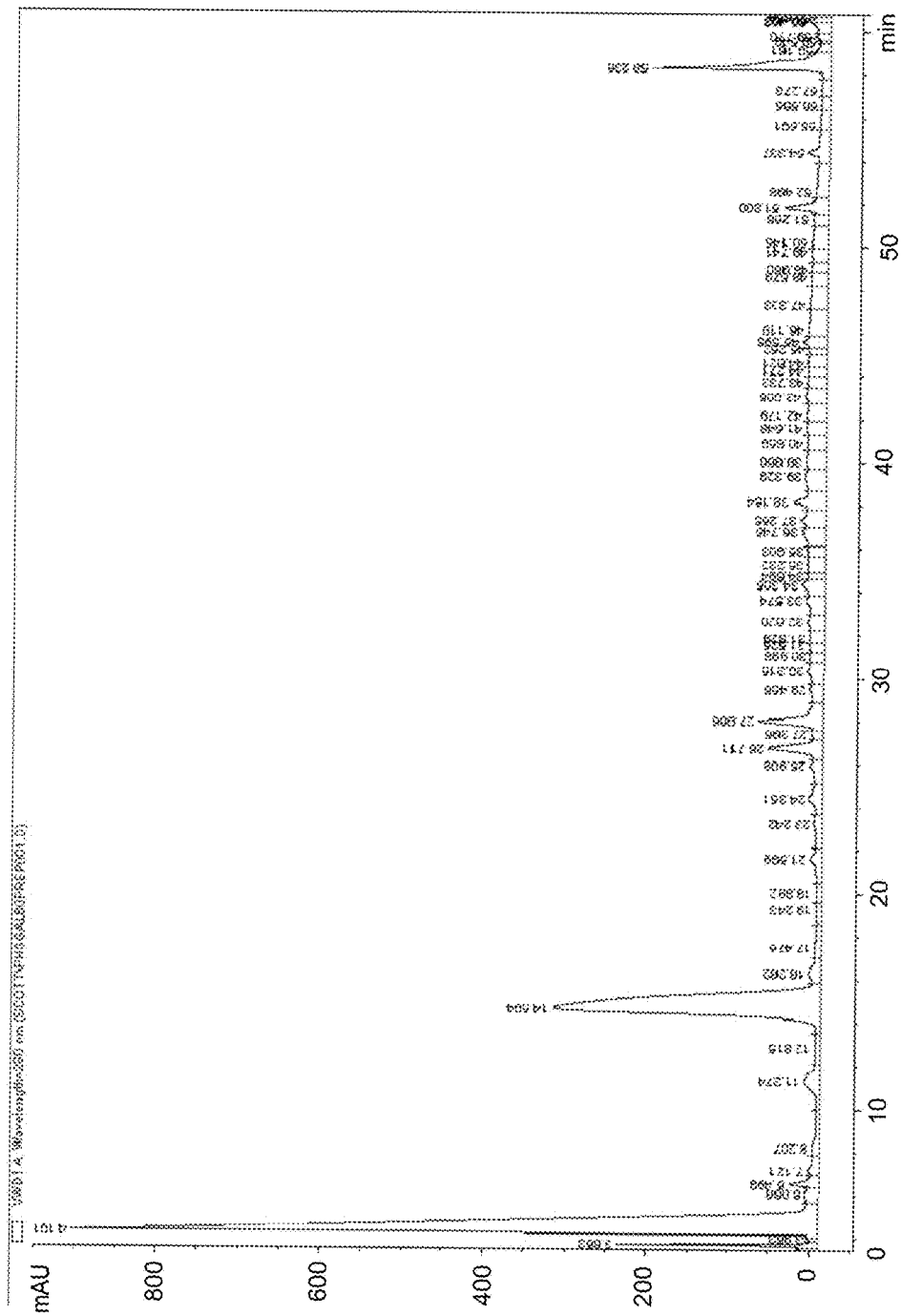
FIG. 31 shows the HPLC results of Example 14: 60 minute Reaction 200 ul injection for MS.
Figure 32:
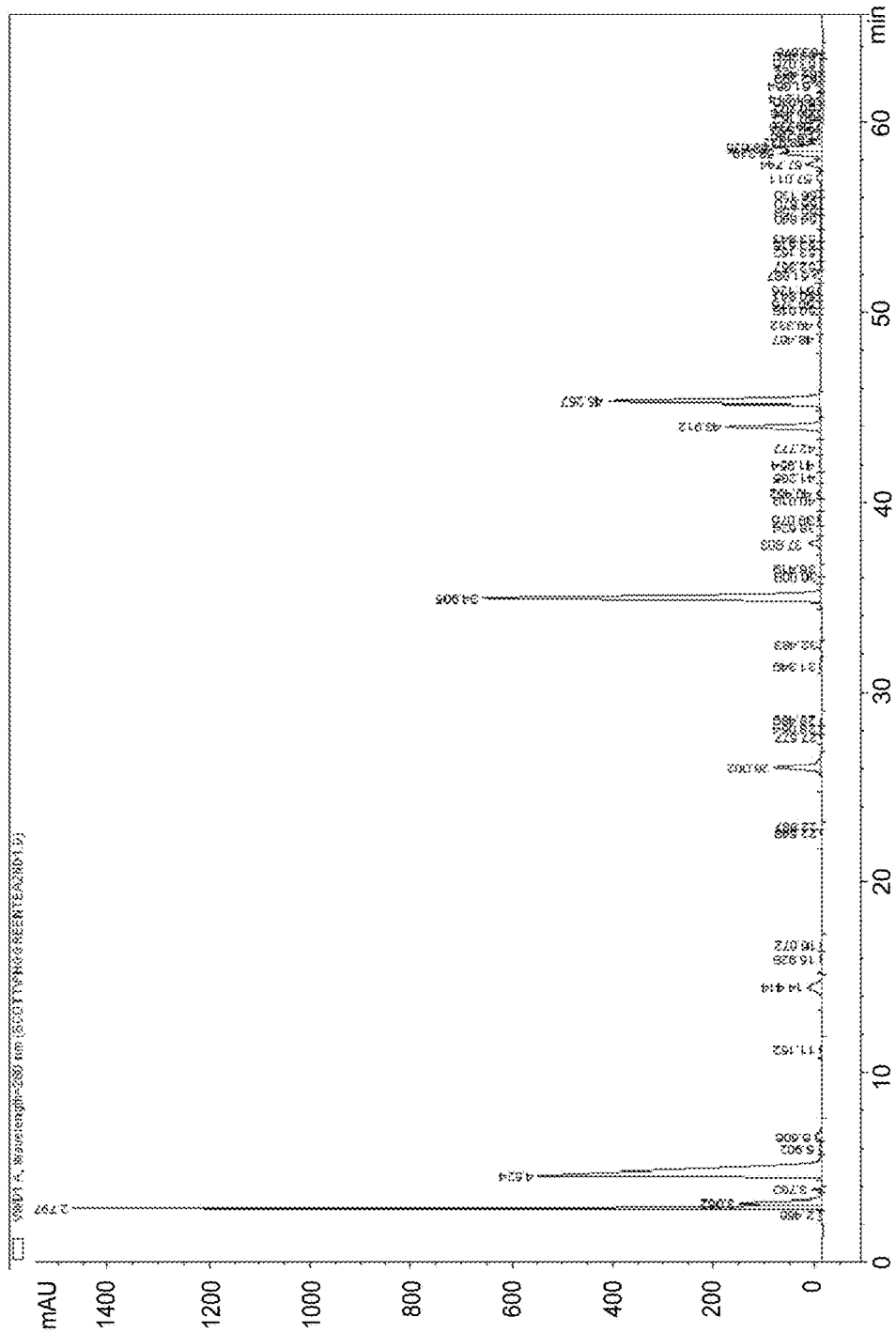
FIG. 32 shows the HPLC results of Example 14: Green Tea Pool 2.
Figure 33:
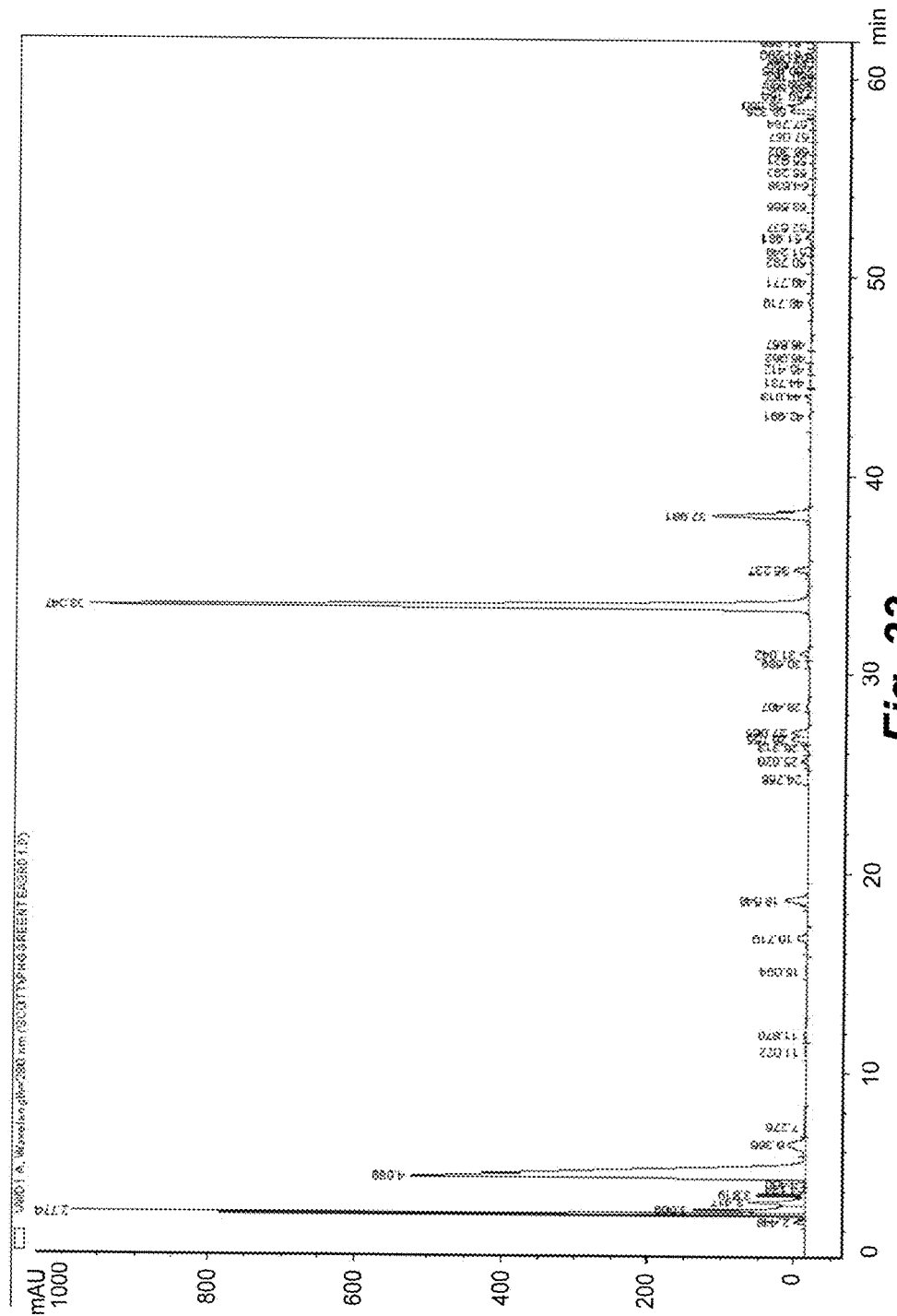
FIG. 33 shows the HPLC results of Example 14: Green Tea Pool 3.

The results of TLC of a silica gel purification of an acetonitrile wash from a C18 column are shown in Figure. 17.

MALDI MS

FIGS. 17-24 are representative spectra for most of the different silica gel chromatographic pools isolated above. No acceptable spectra were obtained for pool 1, while pool 5 was deemed too impure for testing. Negative ion MALDI has been performed on many of the pools but requires calibration before analysis.

TABLE D15

Proton NMR.

| Sample | Chemical Shifts |
|---|---|
| Silica Pool 3 | 7.07, 6.365, 5.716, 1.293 |
| Benzene isopropanol Eluate | 8.71, 6.65, 6.16, 6.08, 5.92, 5.87, 3.66(d), 3.37, 3.24, 1.80(m), 1.637(t), 1.435(m), 0.83(m), 0.54(m) |

TABLE D15-continued

Proton NMR.

| Sample | Chemical Shifts |
|---|---|
| Benzene Ispropanol | 6.56, 6.42, 6.07, 3.81, 3.73, 3.59, 3.53, |
| TFA Eluate | 2.27(t), 1.401, 1.14(m), 0.896(m) |

The test for tannin explains many things. The fact that the material precipitates at low pH explains why we could not analyze it by SEC—it precipitated in the pH 5 buffer which we use for these assays. This also explains why ammonium sulfate precipitates the material despite the fact that it is not a protein—the pH of ammonium sulfate is mildly acidic. This test also raises some questions: since Galahad Red does not precipitate with the addition of protein, it cannot be classed as a tannin. We also know that it is not a protein, nucleic acid, carbohydrate, or lipid.

We can get a better handle on this question by the use of a more highly pure preparation of Galahad Red than our previous purifications gave us. Washing the sample in TFA and resuspending in dilute ammonia gives us a preparation which shows much greater color in methanolic HCl than do the other preparations. Upon phloroglucinolysis, this material gives an array of compounds (we now have a total of 9 pools of material) which is similar to that of burgundy. The fact that Galahad Red responds to phloroglucinolysis suggests that the material is a non-tannin polyflavone.

The MALDI-MS spectra indicates a complex set of mixtures indicating that the break down products are extremely complex. Of interest, in the benzene iso-propanol eluate MS, the ion at m/z 556 is separated from the major ion at 268 by 288 mass units, the mass of catechin.

NMR of both the benzene isopropanol eluates shows several interesting points. Both have chemical shifts between 6.0 and 6.1 ppm, consistent with phloroglucinol but also have shifts at around 3.6 ppm, as expected for carbon 3 in the flavone skeleton. The benzene isopropanol eluate also has shifts at 5.92 and 5.87 ppm corresponding to the expected shifts of carbons 6 and 8 in the A ring of the flavone skeleton. Both eluates have shifts around 6.5 ppm, as expected for the B ring protons of a flavone. Where these spectra differ from a standard flavone is around 1 ppm where they have several multiplets which look almost like a fatty acid. Note that we do not believe a fatty acid could be a contaminant of the preparation as it should have eluted in the acetonitrile wash. Esterification to one of the hydroxyls on a flavone ring is ruled out by the harsh phloroglucinolysis conditions which would be expected to transesterify the fatty acid, causing it to elute in the acetonitrile wash. It is possible that a long chain aldehyde could add to the flavone ring through an electrophilic substitution mechanism, forming a flavone adduct which would be highly hydrophobic (explaining the extreme conditions required for elution from C18) and not susceptible to hydrolysis. This type of addition has been documented in wine (Frietas and Mateus Environ Chem Lett (2006) 4:175-183 and references therein).

Glycosyl Composition Analysis of Galahad Red

The monosaccharides are identified by their retention times in comparison to standards, and the carbohydrate character of these are authenticated by their mass spectra. For interpreting the mass spectral data, fragment ion 73 is the characteristic base fragment for all TMS methyl glycosides, 204 and 217 are characteristic of neutral sugars, and 173 is characteristic of amino sugars. Fragment 217 is also characteristic of uronic acids, and fragment ion 298 is characteristic of the sialic acids.

TABLE D16

Monosaccharides in Galahad Red

| Sample Glycosyl residue<br>Galahad DEAE NaOH | Mass (μg) | Mole %[1] |
|---|---|---|
| Arabinose(Ara) | trace | trace |
| Ribose(Rib) | n.d. | n.d. |
| Rhamnose (Rha) | trace | trace |
| Fucose (Fuc) | n.d. | n.d. |
| Xylose (Xyl) | trace | trace |
| Glucuronic Acid(GlcUA) | n.d. | n.d. |
| Galacturonic acid (GalUA) | trace | trace |
| Mannose (Man) | trace | trace |
| Galactose (Gal) | n.d. | n.d. |
| Glucose (Glc) | trace | trace |
| N Acetyl Galactosamine (GalNAc) | n.d. | n.d. |
| N Acetyl Glucosamine (GlcNAc) | n.d. | n.d. |
| Heptose(Hep) | n.d. | n.d. |
| 3 Deoxy-2-manno-2 Octulsonic acid (KDO) | n.d. | n.d. |
| Sum | trace | 100 |

All sugars in this assay were detected at less than 1 μg. This is outside the linear range for our assay so we can only label them as "trace". As 300 μg of material was loaded, the percentage of total carbohydrate in this sample is calculated to be less than 1%.

As proanthocyanidins are frequently glycosylated, we have analyzed the Galahad Red sample for carbohydrate. Carbohydrate analysis shows trace levels of most of the sugars originally found in the sample. The fact that a variety of sugars are found but only in minute levels is consistent with a low level of the previously characterized polysaccharides remaining in the current preparation. If any of these residues were utilized in glycosylation of the red material, we would expect them to be present at much higher levels.

Phloroglucinolysis

Since anything more than such rudimentary analysis of the intact material was not possible, we turned our efforts to degradation studies. Initially, we tried 3 different approaches; thiolysis, degradation using butanol/iron/acid and phloroglucinolysis. Phloroglucinolysis proved to be the most informative assay. Initial conditions of hydrolysis were comparatively harsh as we wanted to effect complete degradation of the polymer. The results of TLC of the phloroglucinolysis reaction mix and fractions from a C18 column are shown in FIG. 16. When we went to a more mild phloroglucinolysis in the presence of ascorbic acid, we were able to analyze the resulting compounds by HPLC, as shown in FIGS. 26-33.

Interestingly, the main peak observed is a catechin phloroglucinol adduct which is consistent with a polymer consisting of catechin subunits. A small amount of nonconjugated catechin, which comes from the termini of catechin chain, was also observed. No significant levels of compounds found in green tea (which is known to contain the antiviral compound prodelphinidin gallate) were observed. While we can clearly see a catechin polymer in Galahad Red, we cannot prove that the polymer is exclusively catechin.

Figure 34:
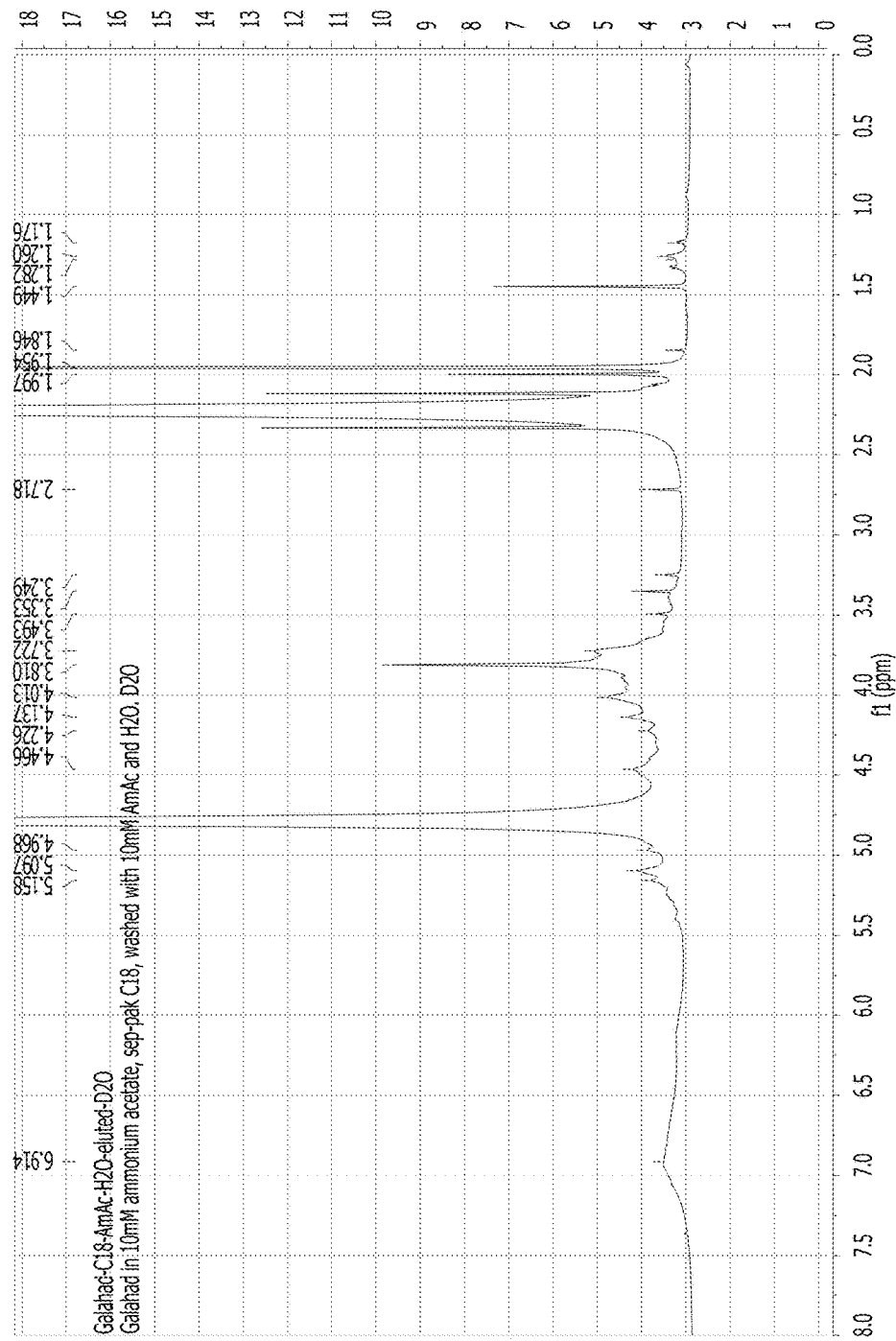
FIG. 34 shows the NMR spectroscopy results of Example 14: 1D proton NMR spectrum of GH-C18-1, a fraction from Sep-Pak C18 eluted with 10 mM ammonium acetate and water. Aromatic compound content is low in this fraction. The carbohydrates are O-methylated as indicated by the signals at 3.82 ppm.
Figure 35:
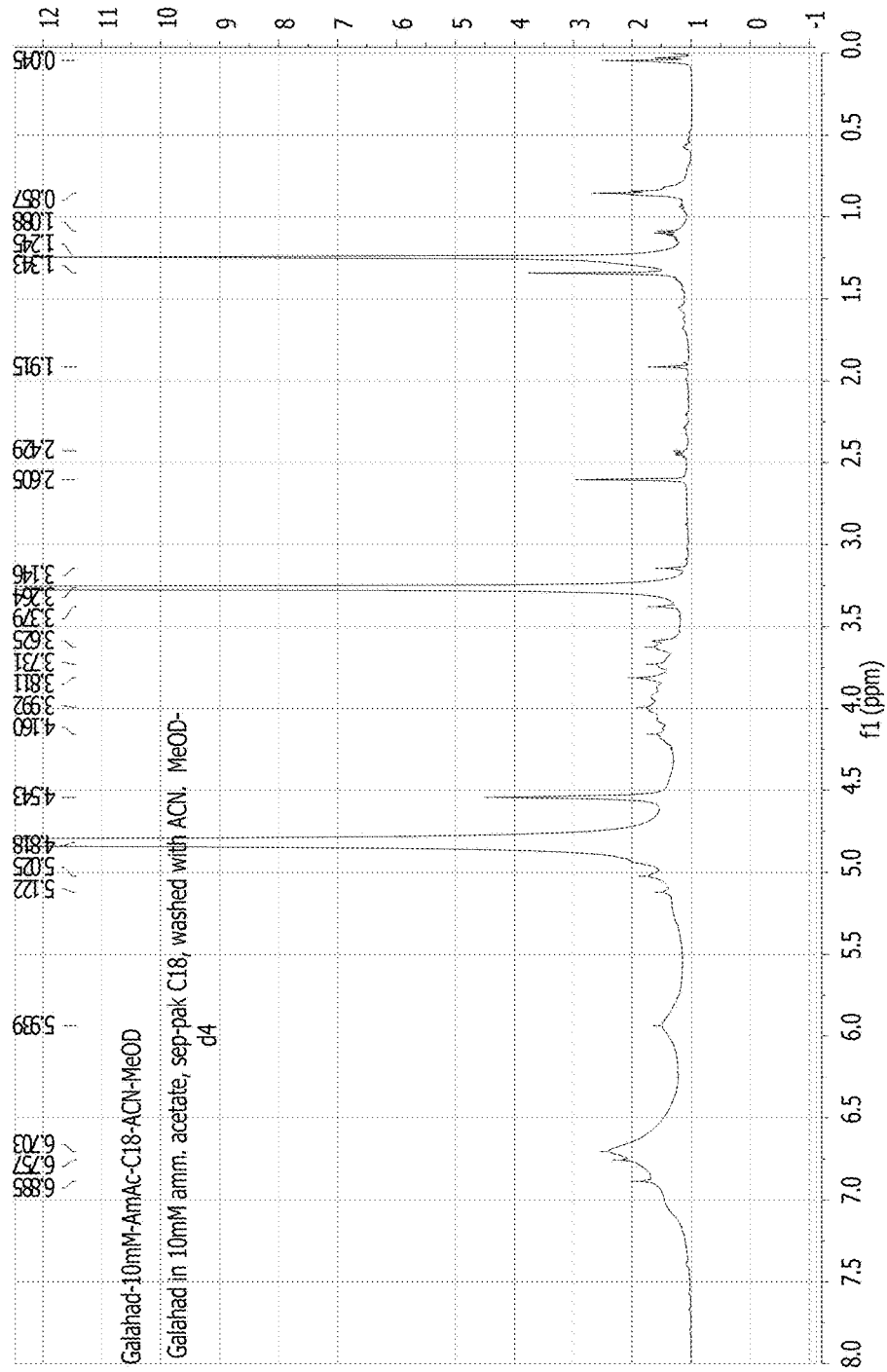
FIG. 35 shows the NMR spectroscopy results of Example 14: 1D proton NMR spectrum of GH-C18-2, a fraction from Sep-Pak C18 eluted with acetonitrile and dissolved in methanol-d4. Aromatic compound content is much higher in this fraction than in GH-C18-1, and carbohydrate content is significantly lower.
Figure 36:
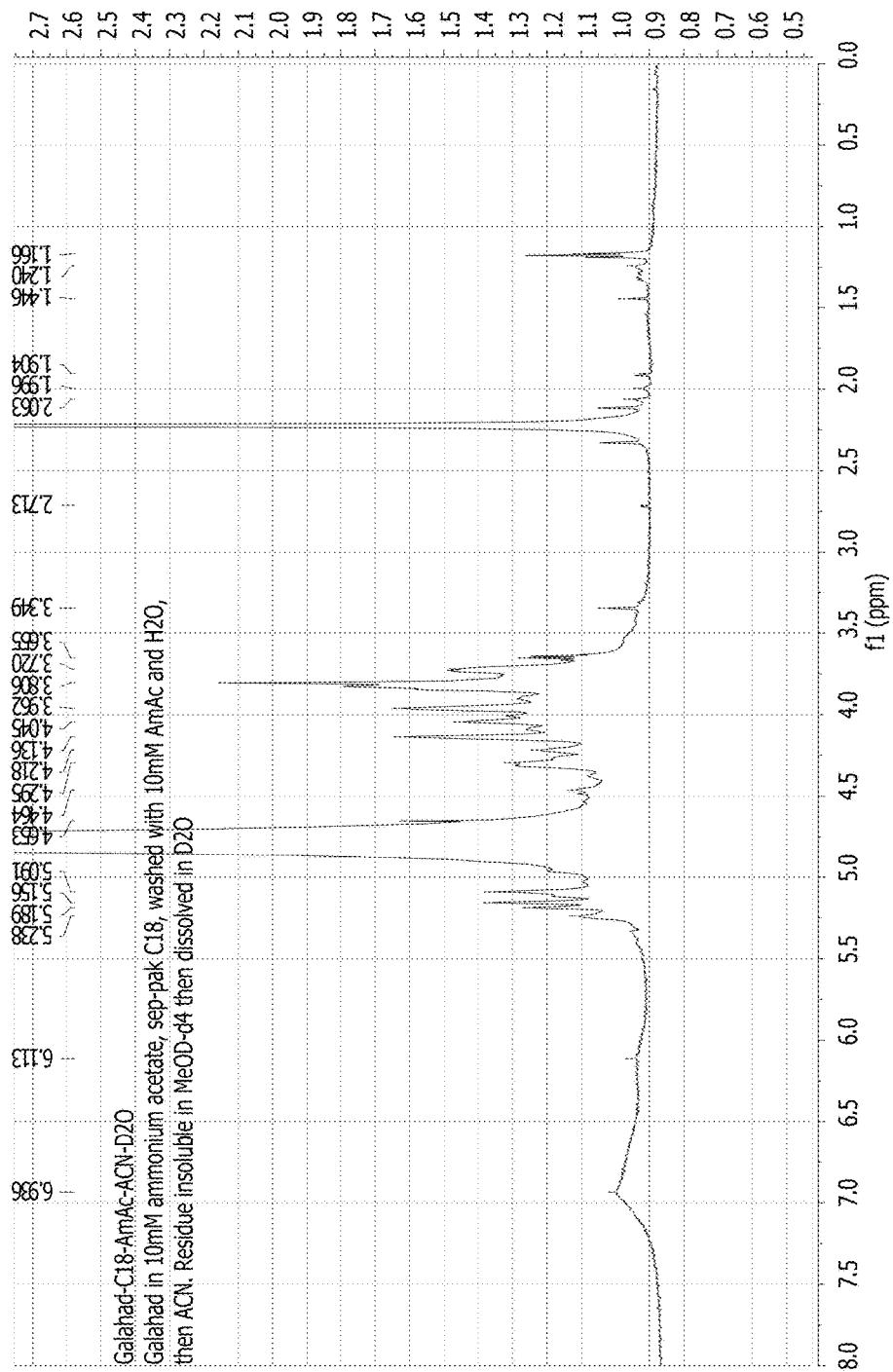
FIG. 36 shows the NMR spectroscopy results of Example 14: 1D proton NMR spectrum of GH-C18-3, a fraction from Sep-Pak C18 eluted with acetonitrile and dissolved in D2O. The molecular weight of the carbohydrate in this fraction is lower as compared with the other two, GH-C18-1 and GH-C18-2. The carbohydrate is most likely arabinan with different linkages.
Figure 37:
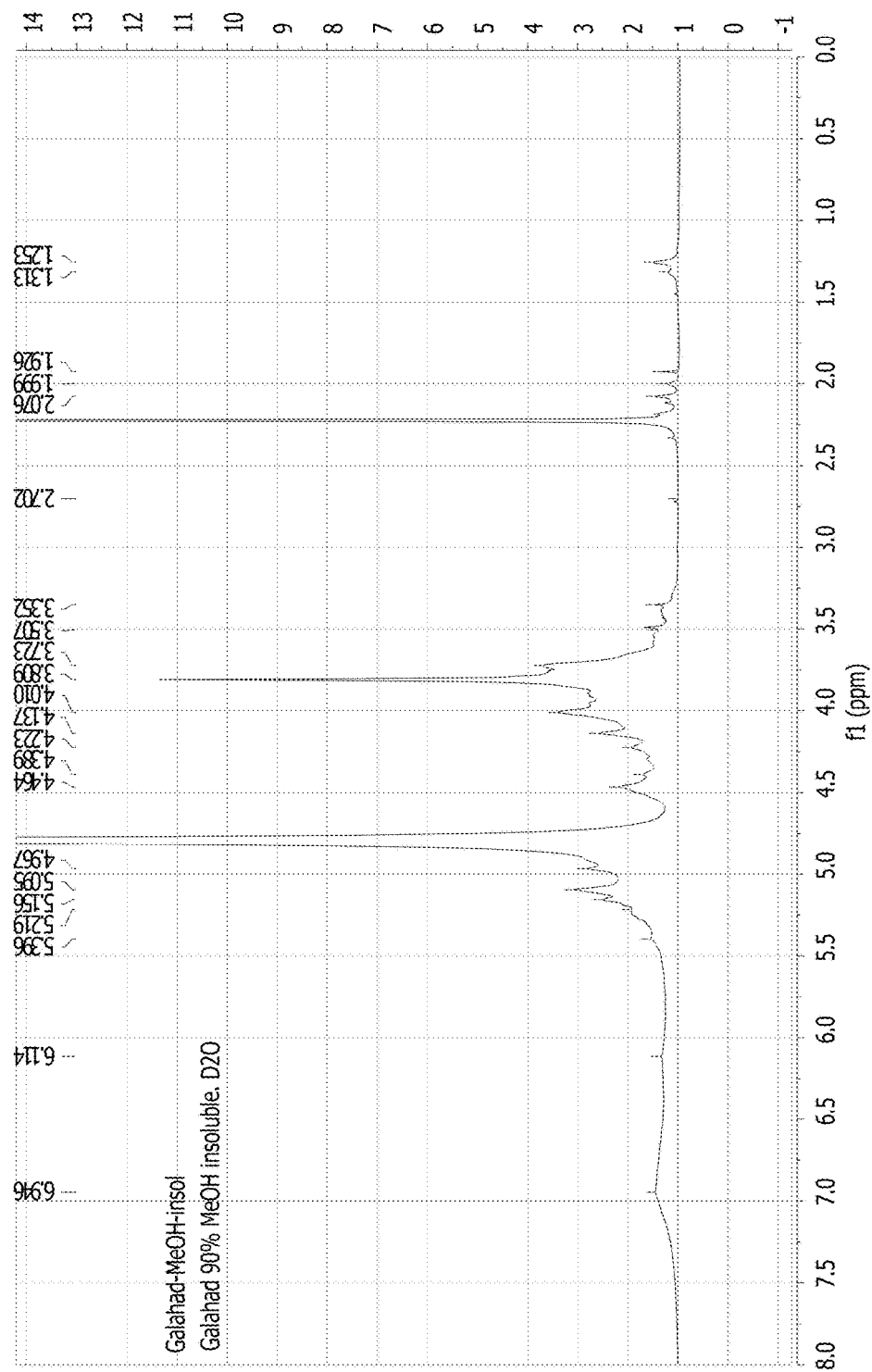
FIG. 37 shows the NMR spectroscopy results of Example 14: 1D proton NMR spectrum of GH-alcohol-1, a fraction precipitated in 90% MeOH and dissolved in D2O. Aromatic compound content is low in this fraction. The carbohydrates are O-methylated as indicated by the signals at 3.81 ppm. This fraction is very similar to GH-C18-1 in composition.
Figure 38:
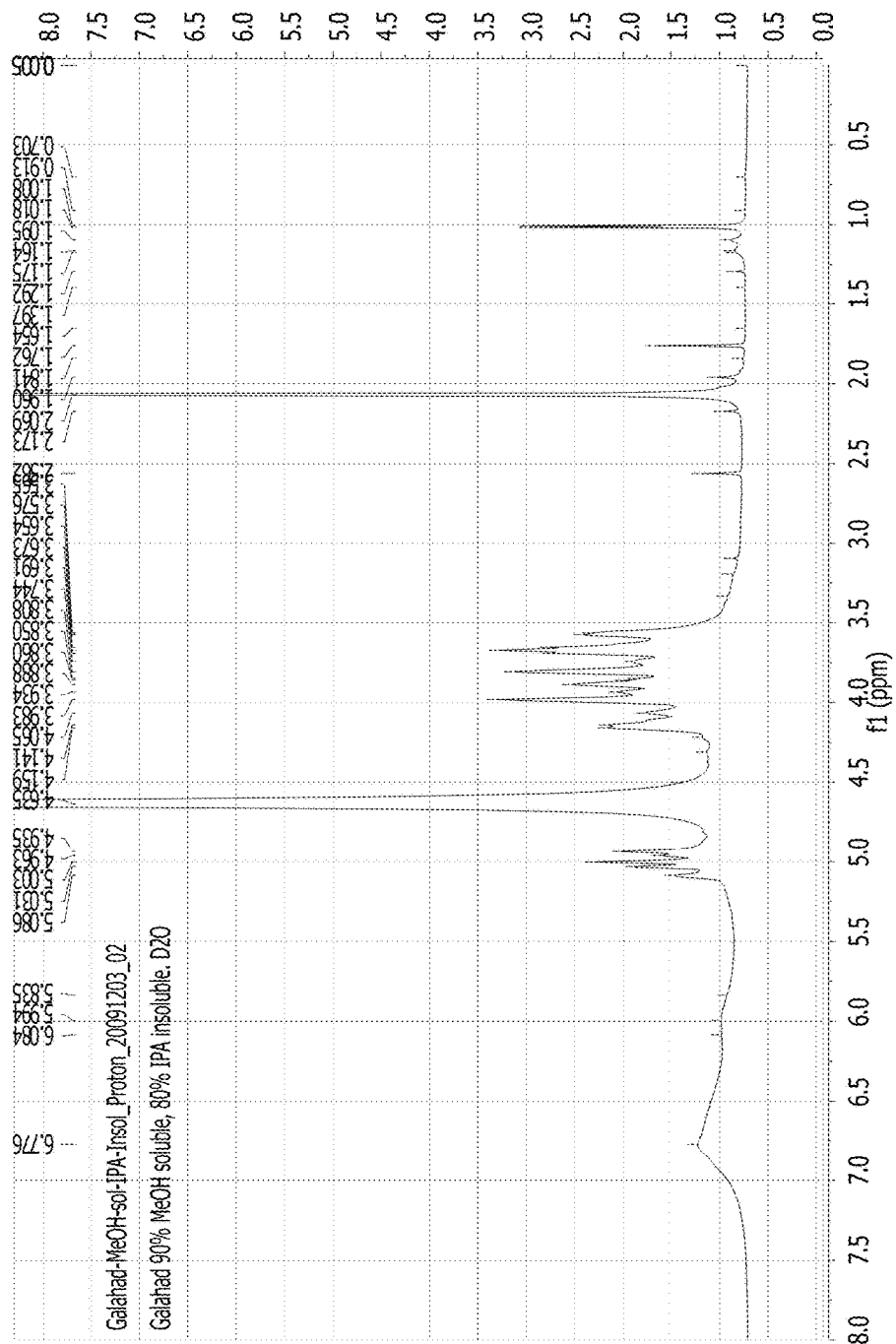
FIG. 38 shows the NMR spectroscopy results of Example 14: 1D proton NMR spectrum of GH-alcohol-2, a fraction precipitated in 80% iso-propanol and dissolved in D2O. The molecular weight of the carbohydrate in this fraction is lower as indicated by the sharp peaks. Again, the carbohydrate is most likely arabinan with different linkages. This fraction is very similar to GH-C18-3 in composition.
Figure 39:
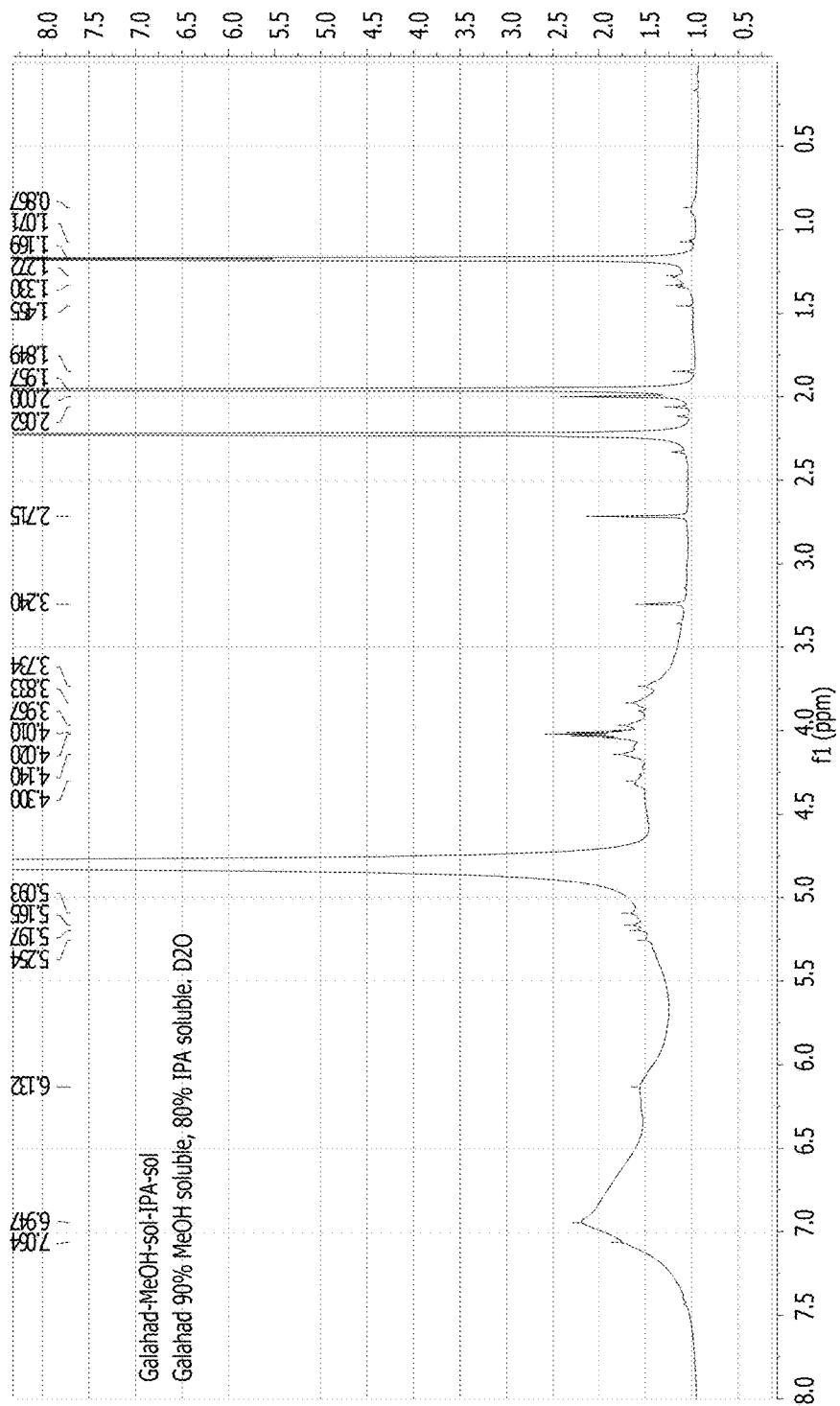
FIG. 39 shows the NMR spectroscopy results of Example 14: 1D proton NMR spectrum of GH-alcohol-3, a fraction soluble in 80% iso-propanol and dissolved in D2O. Very similar to GH-C18-2, aromatic compound content is much higher in this fraction than in GH-alcohol-1 or GH-alcohol-2, and carbohydrate content is significantly lower, which is consistent with the results from GC analysis.

NMR Spectroscopy of Monosaccharide Methyl Glycosides 1D proton NMR spectra for fractions of Galahad, including GH-C18-1, GH-C18-2, GH-C18-3, GH-alcohol-1-MeOH insoluble, GH-alcohol-2-IPA insoluble and GH-alcohol-3-IPA soluble, are shown and explained in FIGS. 34-36.

The aromatic compounds are very likely glycosylated, which is why these aromatic components have relatively high solubility in water. The glycans attached (as in GH-alcohol-2 and GH-alcohol-3 or GH-C18-3) are arabinan with different linkages based on the 1D proton NMR spectra.

It is well known that both polyphenols (or other compounds with similar structures) and arabinans have a variety of biological activities. So far more than 200 polyphenols have been identified in red wine. This is probably why we always see broad peaks for the aromatic proton signals in NMR spectra of original Galahad and all the fractions.

CONCLUSION

Figure 40:
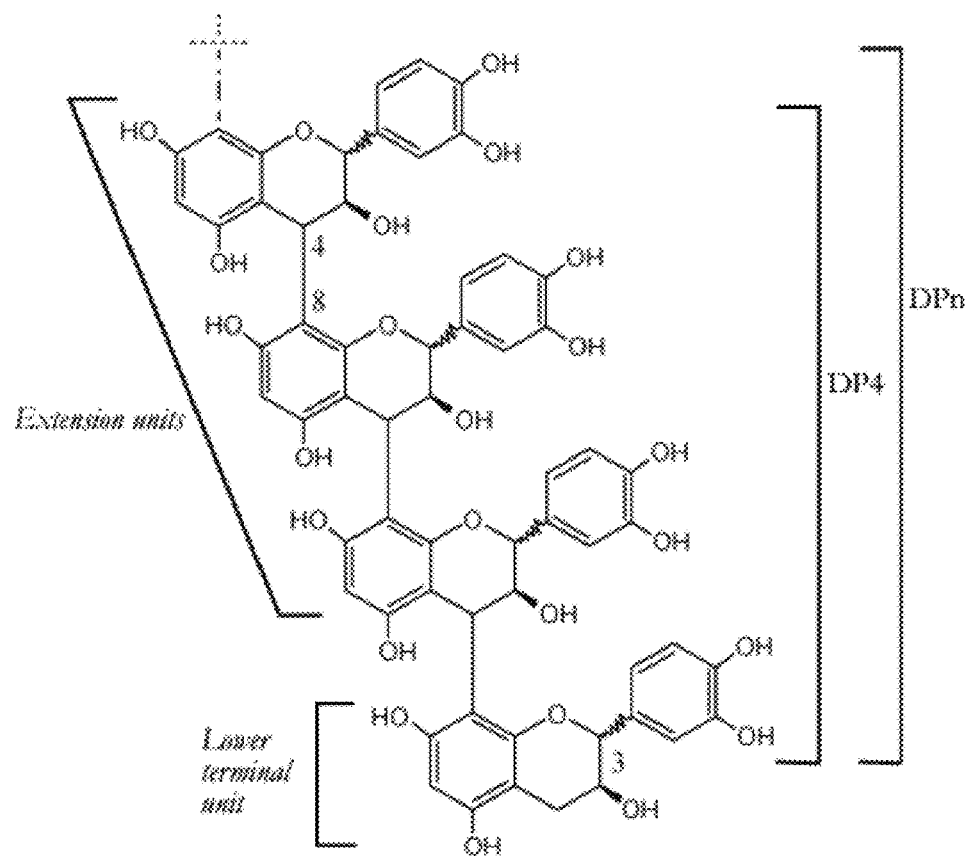
FIG. 40 shows the structure of an illustrative procyadin polymer.

Galahad is made of two main polymers, which, in certain embodiments, are both needed for full biological activity. Through various analytical techniques listed above we have concluded that Galahad is made of a polysaccharide portion and a non-carbohydrate polymer. The glycosyl composition, linkage, and NMR analysis indicates that the main carbohydrate component in the sample is an arabinan. The non-carbohydrate portion was indicated to be a catechin polymer. An example of a procyadin polymer is shown in FIG. 40. While we can clearly see a catechin polymer in Galahad Red, we cannot prove that the polymer is exclusively all catechin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An inactivated anti-viral vaccine, the vaccine comprising:
   (a) a composition that binds to a virus and inhibits said virus, said composition comprising:
      an isolated polysaccharide comprising an arabinofuranosyl residue, a galactopyranosyl residue, and a galactouronic acid; and
      a catechin polymer;
      wherein said composition is soluble in water; and
      wherein said composition is obtainable by a method comprising:
         preparing a substantially homogeneous aqueous mixture or solution of plant material from one or more plants of the Vitaceae family;
         contacting said mixture or solution with an ion exchange resin and recovering the colored product; and
         further purifying the colored product by removing components that can pass through a dialysis filter that generally passes molecules having a molecular weight of a $5 \times 10^5$ Daltons or less to produce said composition; and
   (b) the virus, wherein said composition binds to the virus and inactivates the virus, and wherein the vaccine is formulated as a unit dosage formulation.

2. An inactivated anti-viral vaccine, the vaccine comprising:
   (a) a composition that binds to a virus and inhibits said virus, said composition comprising:
      an isolated polysaccharide comprising an arabinofuranosyl residue, a rhamnopyranosyl residue, a galactopyranosyl residue, a glucopyranosyl residue, a mannopyranosyl residue, and a galactouronic acid; and
      a non-carbohydrate aromatic polymer;
      wherein said composition comprises about 40 to about 44 percent oxygen, about 44 to about 48 percent carbon, about 3 to about 6 percent hydrogen; and about 0.1 to about 1 percent nitrogen;
      wherein said composition is soluble in water; and
      wherein said composition is obtainable by a method comprising:
         preparing a substantially homogeneous aqueous mixture or solution of plant material from one or more plants of the Vitaceae family;
         contacting said mixture or solution with an ion exchange resin and recovering the colored product; and
         further purifying the colored product by removing components that can pass through a dialysis filter that generally passes molecules having a molecular weight of a $5 \times 10^5$ Daltons or less to produce said composition; and
   (b) the virus, wherein said composition binds to the virus and inactivates the virus, and wherein the vaccine is formulated as a unit dosage formulation.

3. The vaccine of claim 1, wherein the composition comprises about 10 to about 30 weight percent polysaccharide and about 70 to about 90 weight percent catechin polymer.

4. The vaccine of claim 1, wherein the composition comprises a component having a molecular weight greater than about 1 million Daltons.

5. The vaccine of claim 1, wherein the composition comprises a component having a molecular weight in the range of about 60,000 to about 100,000 Daltons.

6. The vaccine of claim 4, wherein the composition comprises an additional component having a molecular weight in the range of about 60,000 to about 100,000 Daltons.

7. The vaccine of claim 6, wherein the ratio of the amount of the component having a molecular weight greater than about 1 million Daltons to the amount of the component having a molecular weight in the range of about 60,000 to about 100,000 Daltons is about 95:5.

8. The vaccine of claim 1, wherein said composition does not comprise protein.

9. The vaccine of claim 1, wherein said polysaccharide comprises:
   about 30 to about 75 mole percent arabinose;
   about 0 to about 10 mole percent rhamnose;
   about 0 to about 5 mole percent xylose;
   about 0 to about 8 mole percent glucuronic acid;
   about 3 to about 36 mole percent galactouronic acid;
   about 0 to about 6 mole percent mannose;
   about 1 to about 20 mole percent galactose; and
   about 0 to about 13 mole percent glucose.

10. The vaccine of claim 2, wherein said polysaccharide comprises:
    about 60 to about 66 mole percent arabinose;
    about 4.1 to about 4.5 mole percent rhamnose;
    about 2.2 to about 2.4 mole percent xylose;
    about 8.7 to about 9.7 mole percent galactouronic acid;
    about 2.3 to about 2.5 mole percent mannose;
    about 13.7 to about 15.1 mole percent galactose; and
    about 4.2 to about 4.6 mole percent glucose.

11. The vaccine of claim 1, wherein said polysaccharide comprises:

a terminally linked arabinofuranosyl residue (t-Araf);
a 2-linked arabinofuranosyl residue (2-Araf);
a 2-linked rhamnopyranosyl residue (2-Rhap);
a 3-linked arabinofuranosyl residue (3-Araf);
a terminally linked galactopyranosyl residue (t-Gal);
a 5-linked arabinofuranosyl residue (5-Araf);
a 3-linked glucopyranosyl residue (3-Glc) and/or a 2,4-linked rhamnopyranosyl residue (2,4-Rhap);
a 2-linked glucopyranosyl residue (2-Glc);
a 4-linked mannopyranosyl residue (4-Man);
a 3,5-linked arabinofuranosyl residue (3,5-Araf);
a 2,5-linked arabinofuranosyl residue (2,5-Araf);
a 4-linked glucopyranosyl residue (4-Glc);
a 2,3,5-linked arabinofuranosyl residue (3,5-Araf) and/or a 2,3,4-linked arabinopyranosyl residue (2,3,4-Arap);
a 4-linked galactouronic acid (4-gal A);
a 3,6-linked galactopyranosyl residue (3,6-Gal);
a 2,3,4,6-linked mannopyranosyl residue (2,3,4,6-Man);
a 2,3,4,6-linked galactopyranosyl residue (2,3,4,6-Gal) &2,3,4-linked galactouronic acid; and
a 2,3,4,6-linked glucopyranosyl residue (2,3,4,6-Glc).

12. The vaccine of claim 11, wherein said polysaccharide comprises:
said terminally linked arabinofuranosyl residue (t-Araf) comprises about 14.2 to about 15.7 wt percent of said polysaccharide;
said 2-linked arabinofuranosyl residue (2-Araf) comprises about 9.1 to about 10.08 wt percent of said polysaccharide;
said 2-linked rhamnopyranosyl residue (2-Rhap) comprises about 0.3 wt percent of said polysaccharide;
said 3-linked arabinofuranosyl residue (3-Araf) comprises about 3.0 to about 3.4 wt percent of said polysaccharide;
said terminally linked galactopyranosyl residue (t-Gal) comprises about 2.0 to about 2.2 wt percent of said polysaccharide;
said 5-linked arabinofuranosyl residue (5-Araf) comprises about 15.0 to about 16.6 wt percent of said polysaccharide;
said 3-linked glucopyranosyl residue (3-Glc) and/or 2,4-linked rhamnopyranosyl residue (2,4-Rhap) comprises about 0.7 wt percent of said polysaccharide;
said 2-linked glucopyranosyl residue (2-Glc) comprises about 1.1 to about 1.3 wt percent of said polysaccharide;
said 4-linked mannopyranosyl residue (4-Man) comprises about 1.3 to about 1.5 wt percent of said polysaccharide;
said 3,5-linked arabinofuranosyl residue (3,5-Araf) comprises about 6.6 to about 7.3 wt percent of said polysaccharide;
said 2,5-linked arabinofuranosyl residue (2,5-Araf) comprises about 5.0 to about 5.6 wt percent of said polysaccharide;
said 4-linked glucopyranosyl residue (4-Glc) comprises about 4.6 to about 5.0 wt percent of said polysaccharide;
said 2,3,5-linked arabinofuranosyl residue (3,5-Araf) and/or 2,3,4-linked arabinopyranosyl residue (2,3,4-Arap) comprises about 25.7 to about 28.4 wt percent of said polysaccharide;
said 4-linked galactouronic acid (4-gal A) comprises about 1.4 to about 1.6 wt percent of said polysaccharide;
said 3,6-linked galactopyranosyl residue (3,6-Gal) comprises about 0.4 wt percent of said polysaccharide;
said 2,3,4,6-linked mannopyranosyl residue (2,3,4,6-Man) comprises about 0.7 wt percent of said polysaccharide;
said 2,3,4,6-linked galactopyranosyl residue (2,3,4,6-Gal) &2,3,4-linked galactouronic acid comprises about 2.0 to about 2.2 wt percent of said polysaccharide; and
said 2,3,4,6-linked glucopyranosyl residue (2,3,4,6-Glc) comprises about 2.1 to about 2.3 wt percent of said polysaccharide.

13. The vaccine of claim 1, wherein the virus is from a family selected from the group consisting of Adenoviridae, Picornaviridae, Reoviridae, Arenaviridae, Bunyaviridae, Coroanviridae, Herpesviridae, Orthomyxoviridae, Paramyxoviridae, Poxviridae Rhabdoviridae, Flaviviridae, and Retroviridae.

14. The vaccine of claim 2, wherein said composition provides a NMR spectrum as shown in FIG. 3A.

15. The vaccine of claim 1, wherein said composition is formulated in a delivery form selected from the group consisting of a nasal spray and an injectable.

16. The vaccine of claim 1, wherein the composition is obtained by said method comprising:
preparing a substantially homogeneous aqueous mixture or solution of plant material from one or more plants of the Vitaceae family;
contacting said mixture with an ion exchange resin and recovering the colored product; and
further purifying the colored product by removing components that can pass through a dialysis filter that generally passes molecules having a molecular weight of a $5 \times 10^5$ Daltons or less to produce a composition that binds a virus.

17. A method of preparing an inactivated anti-viral vaccine, said method comprising:
contacting a virus with a composition that binds to the virus and inhibits said virus, said composition comprising:
an isolated polysaccharide comprising an arabinofuranosyl residue, a galactopyranosyl residue, and a galactouronic acid; and
a catechin polymer;
wherein said composition is soluble in water; and
wherein said composition is obtainable by a method comprising:
preparing a substantially homogeneous aqueous mixture or solution of plant material from one or more plants of the Vitaceae family;
contacting said mixture or solution with an ion exchange resin and recovering the colored product;
wherein said contacting is carried out for a sufficient time to inactivate the virus.

18. A method of inducing an immune response in a mammal, said method comprising administering to said mammal a vaccine according to claim 1 in an amount sufficient to induce an immune response.

19. The vaccine of claim 1, wherein the vaccine additionally comprises an adjuvant.

20. The vaccine of claim 1, wherein the vaccine does not comprise any adjuvant.

21. The method of claim 18, wherein the method comprises administering the vaccine intranasally.

22. The method of claim 18, wherein the method comprises administering the vaccine by injection.

23. The method of claim 22, wherein the method comprises administering the vaccine by intradermal injection.

24. The method of claim 18, wherein the method comprises administering the vaccine in at least two, separate doses.

\* \* \* \* \*